(12) United States Patent
Blanckaert et al.

(10) Patent No.: US 11,576,735 B2
(45) Date of Patent: Feb. 14, 2023

(54) CONTROLLABLE STEERABLE INSTRUMENT

(71) Applicant: Steerable Instruments NV, Sint-Denijs-Westrem (BE)

(72) Inventors: Bart Blanckaert, Eeklo (BE); Frank Dewaele, De Pinte (BE); Cyriel Mabilde, Oudenaarde (BE); Lieven Maene, Knokke-Heist (BE); Alain Kalmar, Ghent (BE)

(73) Assignee: Steerable Instruments N.V., Sint-Denijs-Westrem (BE)

( * ) Notice: Subject to any disclaimer, the term of this patent is extended or adjusted under 35 U.S.C. 154(b) by 362 days.

(21) Appl. No.: 16/762,704

(22) PCT Filed: Nov. 15, 2018

(86) PCT No.: PCT/EP2018/081450
§ 371 (c)(1),
(2) Date: May 8, 2020

(87) PCT Pub. No.: WO2019/096939
PCT Pub. Date: May 23, 2019

(65) Prior Publication Data
US 2021/0369359 A1    Dec. 2, 2021

(30) Foreign Application Priority Data

Nov. 15, 2017 (EP) .................................... 17201791
Jun. 12, 2018 (EP) .................................... 18177332

(51) Int. Cl.
*A61B 34/30* (2016.01)
*A61B 34/00* (2016.01)
*B25J 9/16* (2006.01)

(52) U.S. Cl.
CPC .............. *A61B 34/30* (2016.02); *A61B 34/77* (2016.02); *B25J 9/1664* (2013.01); *A61B 2034/301* (2016.02); *A61B 2034/302* (2016.02)

(58) Field of Classification Search
CPC ... A61B 34/30; A61B 34/77; A61B 2034/302; A61B 2034/301; B25J 9/1664
(Continued)

(56) References Cited

U.S. PATENT DOCUMENTS 10,543,605 B2 * 1/2020 Piette ..................... B25J 9/0018
2007/0013336 A1   1/2007 Nowlin et al.
(Continued)

FOREIGN PATENT DOCUMENTS

DE    102013005982 A1    10/2014
WO    2006124390 A2    11/2006
WO    2016091858 A1    6/2016

OTHER PUBLICATIONS

International Search Report dated Feb. 19, 2019 from PCT International Application No. PCT/EP2018/081450.
(Continued)

*Primary Examiner* — Dalena Tran
(74) *Attorney, Agent, or Firm* — Amster, Rothstein & Ebenstein LLP

(57) ABSTRACT

A steerable instrument (100) controllable by a robotic arm (200), having a proximal end (20) and a distal (40) end comprising: a cylindrical shaft (130), a cylindrical bendable proximal part (120) and a cylindrical bendable distal part (140), a connector (110) configured for dismountable attachment to the robotic arm (200), attached in fixed rotational relation to the bendable proximal part (120), an end effector (150) attached in fixed rotational relation to the bendable distal part (140), the steerable instrument (100) configured such that: the bendable distal part (140) bends responsive to bending of the bendable proximal part (120), and the end effector (150) is rotatable when the bendable distal part (140) is in a bent position by a complementary rotation of the connector (110), the shaft (130) is pivotable around a fulcrum zone (134) on the shaft (130) and changes direction responsive to a complementary movement of the connector (110), thereby providing control of the shaft (130) direction, bending of the bendable distal part (140), and rotation of the end effector (150) through robotic movement of the connector (110).

16 Claims, 30 Drawing Sheets

(58) Field of Classification Search
USPC ............... 600/146, 114, 145, 129, 101, 229;
901/14, 901; 606/1, 46, 155
See application file for complete search history.

(56) References Cited

U.S. PATENT DOCUMENTS

| | | | |
|---|---|---|---|
| 2008/0154288 A1* | 6/2008 | Belson | A61B 1/0055 |
| | | | 606/150 |
| 2009/0216083 A1* | 8/2009 | Durant | A61B 1/0055 |
| | | | 600/130 |
| 2009/0299344 A1 | 12/2009 | Lee et al. | |
| 2011/0277775 A1 | 11/2011 | Holop et al. | |
| 2011/0295242 A1 | 12/2011 | Spivey et al. | |
| 2016/0120611 A1 | 5/2016 | Lohmeier | |
| 2017/0273702 A1 | 9/2017 | Dewaele et al. | |
| 2018/0099422 A1* | 4/2018 | Yoon | B25J 19/06 |
| 2019/0321976 A1* | 10/2019 | Takagi | A61B 34/71 |

OTHER PUBLICATIONS

Written Opinion dated Feb. 19, 2019 from PCT International Application No. PCT/EP2018/081450.
International Preliminary Report on Patentability dated Mar. 4, 2020 from PCT International Application No. PCT/EP2018/081450.

\* cited by examiner

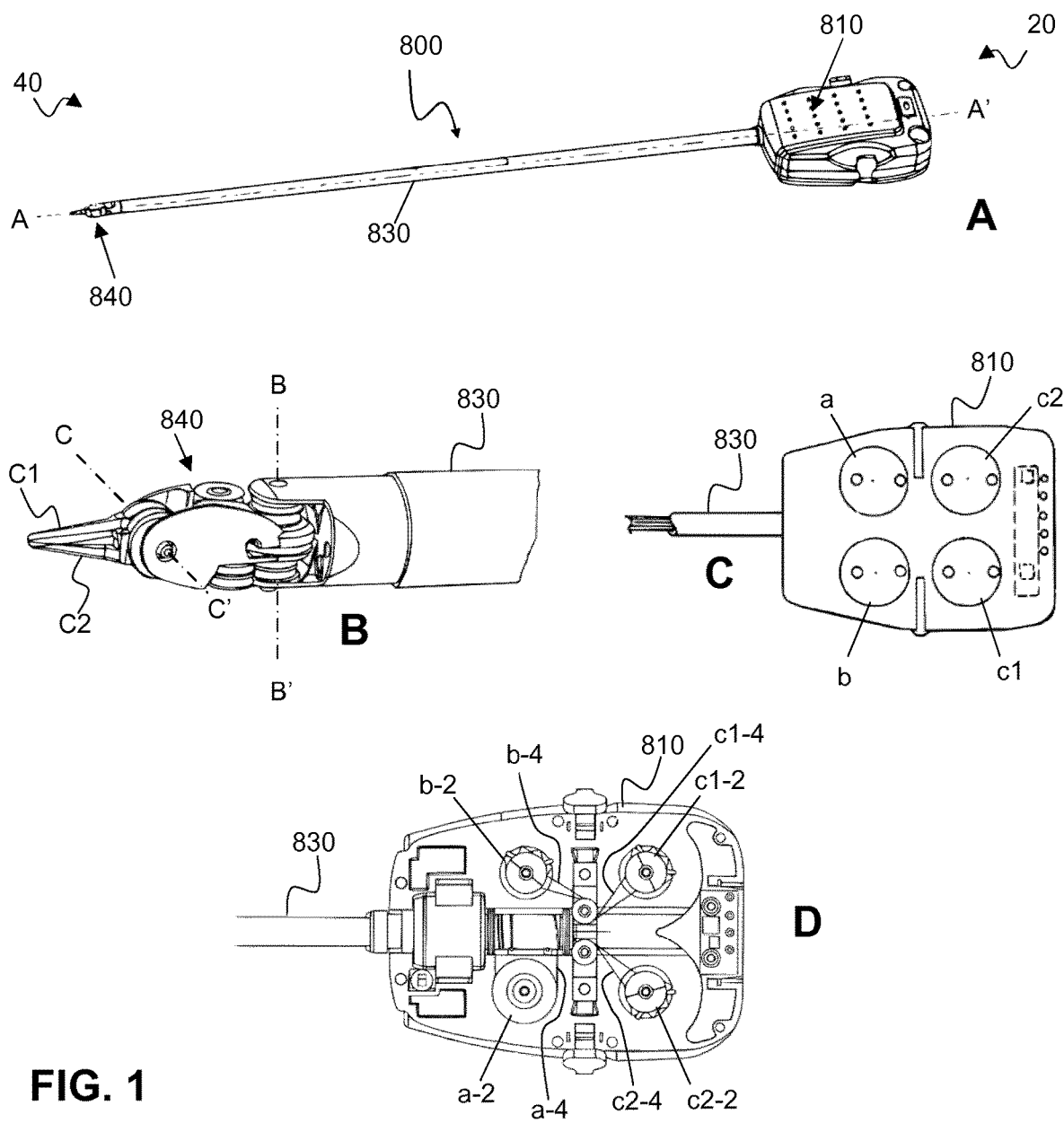
FIG. 1
PRIOR ART
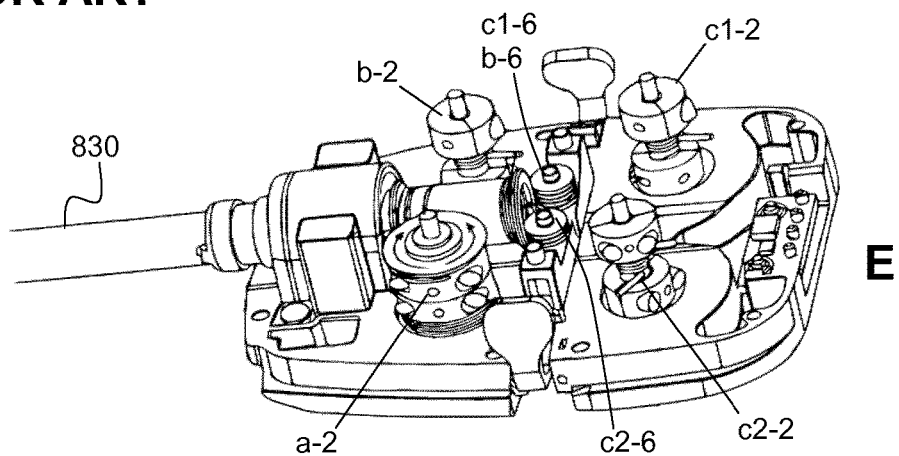

CONTROLLABLE STEERABLE INSTRUMENT

CROSS-REFERENCE TO RELATED APPLICATIONS

This application is a U.S. national stage entry under 35 U.S.C. § 371 of PCT International Patent Application No. PCT/EP2018/081450, filed Nov. 15, 2018, which claims priority to European Patent Application No. 18177332.6, filed Jun. 12, 2018, and European Patent Application No. 17201791.5, filed Nov. 15, 2017, the contents of each of which are incorporated herein by reference in their entirety.

FIELD OF THE INVENTION

The invention is in the field of robotic-controllable steerable instruments for industrial, engineering and medical uses, more in particular for minimally invasive surgery.

BACKGROUND TO THE INVENTION

There is an increased demand for robotic systems that allow remote manipulations in confined spaced having restricted access. The most common use is in the field of minimally invasive surgery, however, robots systems also find applications in mechanical engineering to look within and repair machines where disassembly is impractical or uneconomic for example in manufacturing installations, within building structures, submarine environments, in space, and the like. A steerable instrument can be introduced through a small aperture, and the steerable tip or end effector used to perform actions depending on the end effector including cutting, drilling, joining, cleaning, evacuation, observation (camera). Problems in the art with existing robotically controlled steerable instruments include complexity, expense, wear and tear, cleaning, sterilisation, movement reproducibility, tip stability and range of motions.

The da Vinci surgical system (Intuitive Surgical Inc, CA, USA) is currently a predominant robotic surgical system having a plurality of robotic arms each of which is attachable to a disposable laparoscopic instrument that is a steerable instrument. A typical disposable laparoscopic instrument of the system is shown in FIGS. 1A to 1E. The prior art laparoscopic instrument comprises a shaft having a proximal and distal end, a proximal-end housing that is repeatably attachable to one of the robotic arms of the system. The proximal-end housing is disposed with 4 rotary dials (a, b, c1, c2) to separately control rotation of an end effector (gripper), revolute movement of the shaft, and a separate rotation of the gripper arms to actuate them. A system of wires and pulleys within the disposable laparoscopic instrument transfers forces from the dials towards the end effector (gripper). The complexity of the mechanism is self-evident from prior art FIGS. 1D and 1E; the proximal-end housing and effector end contain a large number of components held under tension by the wires to transmit rotational forces through a rotatable shaft and across revolute joints to the distal wrist and end effector which also contains a complex arrangement. A known disadvantage is the high cost of the instrument because of the multitude of components that have high tolerances and reliability and are able to withstand forces during use and harsh chemical and temperature cleaning protocols, as well as the assembly time. Hence it is an aim to provide a lower cost instrument for robotic use.

The steerable tool disclosed in US 2011/0295242 is manually actuated by a proximal joystick (ball and socket) assembly.

Because the laparoscopic instrument of the art is complex and expensive it is operationally cost-effective (i.e. a necessity) to reuse it. The disposable laparoscopic instrument contains a large number of moving components and revolute joints under tension, each subject to wear and tear. A movement of the instrument must be reproducible; a returning movement must bring the instrument to the same place and in the same orientation. The mechanical joints in the proximal-end housing (e.g. FIGS. 1D and 1E) and distal wrist/end effector (e.g. FIG. 1B) are each a source of error and contribute to a mechanical play or backlash which reduces positional accuracy and reproducibility. As such reusability is limited to a fixed number times. Moreover, a use-counter must be implemented to limit the number of times of reuse.

With reusability is a problem of cleaning and sterilisation. Means must be provided to allow the instrument to be thoroughly cleaned, sterilised and dried, including the innards of the proximal-end housing. The cleaning requires supplementary strategies compared with standard instruments consuming a high number of manual hours; cleaning solution is pumped into the proximal-end housing and further thoroughly rinsed away. The cleaning solution is corrosive, reducing the lifespan of the components. Limited access to the innards impedes the rinsing and drying process; there is a risk that residue of cleaning solution remains.

For some procedures, a continuous rotation of the shaft or of the end effector is desirable, for instance, if the instrument is used for a remote drilling, abrasive action, tightening a thread, winding a cord, and the like. The prior art pulley and wire system has a limit on the number of revolution of the shaft currently to 1.5 rotations. An infinitely rotatable shaft and end effector would be desirable for many applications.

A limitation of minimally invasive surgery is the field of view offered by an endoscope does not allow the surgeon to view that is happening in the space behind the camera. The surgeon not being aware that an instrument has been inserted by an assistant because the instrument tip does not appear in his field of view. Forces provided by a robotic arm are high enough to cause severe damage to a subject, yet there is no safety provision; this can be source of risk since robotic solutions to not have a feedback mechanism to determine whether the surgical tool has been forced in error through tissue.

There is a need in the art for a robot controllable steerable instrument that connects to a robotic arm having a simpler mechanical coupling yet offers control of the instrument direction and of the end effector, that is cheaper to manufacture, has an infinitely rotatable end effector, is safer and overcomes the problems of the art.

SUMMARY

Provided is a steerable instrument (100) controllable by a robotic arm (200), having a proximal end (20) and a distal (40) end comprising:
- a cylindrical shaft (130), a cylindrical bendable proximal part (120) and a cylindrical bendable distal part (140),
- a connector (110) configured for dismountable attachment to the robotic arm (200), attached in fixed rotational relation to the bendable proximal part (120),
- an end effector (150) attached in fixed rotational relation to the bendable distal part (140),
- the steerable instrument (100) configured such that:
    - the bendable distal part (140) bends responsive to bending of the bendable proximal part (120), and the end effector (150) is rotatable when the bendable distal part (140) is in a bent position by a complementary rotation of the connector (110), the shaft (130) is pivotable around a fulcrum zone (134) on the shaft (130) and changes direction responsive to a complementary movement of the connector (110), thereby providing control of the shaft (130) direction, bending of the bendable distal part (140), and rotation of the end effector (150) through robotic movement of the connector (110).

Provided is also a steerable instrument (100) controllable by a robotic arm (200), having a proximal end (20) and a distal (40) end comprising:
- a shaft (130), a bendable proximal part (120) and a bendable distal part (140),
- a connector (110) configured for dismountable attachment to the robotic arm (200), attached in fixed rotational relation to the bendable proximal part (120),
- an end effector (150) attached in fixed rotational relation to the bendable distal part (140),
- the steerable instrument (100) configured such that:
  - the bendable distal part (140) bends responsive to bending of the bendable proximal part (120), and the end effector (150) is rotatable when the bendable distal part (140) is in a bent position by a complementary rotation of the connector (110),
  - the shaft (130) is pivotable around a fulcrum zone (134) on the shaft (130) and changes direction responsive to a complementary movement of the connector (110), thereby providing control of the shaft (130) direction, bending of the bendable distal part (140), and rotation of the end effector (150) through robotic movement of the connector (110).

The steerable instrument (100) may be further configured such that the direction of the end effector (150) is changeable while the shaft is in a fixed rotational position by a complementary movement of the connector (110).

The connector (110) may comprise a rigid member for dismountable attachment to a complementary fitting on the robotic arm (200). The bendable proximal part (120) and bendable distal part (140) may be configured to bend along a curve, and the shaft is rigid (130), and the shaft (130) may be rigid.

The steerable instrument may further comprise a motion amplifier region wherein consecutive plane sections therein gradually increase in size in the distal (40) to the proximal (20) direction, optionally disposed at least partially within the bendable proximal part (120), configured such that bending of the bendable distal part (140) responsive to bending of the bendable proximal part (120) is motion amplified.

The robotic arm (200) may comprise a base end (232), an effector end (262) and a plurality of intervening linkages (230a-h) connected by joints (220a-i), wherein the arrangement of links and joints provides at least 6 degrees of freedom of movement to the effector end (260), wherein the effector end (262) is attached to a fitting (260) for dismountable attachment to the connector (110).

A system is provided comprising a steerable instrument (100) as described herein, and a robotic arm (200) as described herein.

The last two joints (FIG. 13—$R_7$, $R_8$) or three joints (FIG. 10—$R_5$, $R_6$, $R_7$; FIG. 11 $R_7$, $R_8$, $R_9$; FIG. 12 $R_7$, $R_8$, $R_9$) from the effector end (262) of the robotic arm (200) may be arranged such that their axes of rotation intersect, and pass through a zone of motion (122) of the bendable proximal part (120) or through a geometric centre of the zone of motion (122), wherein the zone of motion (122) of the bendable proximal part (120) is a zone coinciding with a central axis (A-A') of the shaft where a central axis (152) of the connector (110), for different connector (110) directions, intersects.

The robotic arm (200) may comprises an adjustable or non-adjustable supporting arm (230f', 252) attachable at a first end to one of the robotic arm (200) linkages (230f) and attachable at a second end to:
- a trocar (264) or a clamp for a trocar (264) and/or
- an instrument guide (266) configured to support a shaft (130) of the steerable instrument (100) or a trocar, wherein the supporting arm (230f', 252) maintains the trocar (264) or an instrument guide (266) in non-adjustable or adjustable relation to the linkage, and the direction of the linkage controls the direction of the trocar (264) or an instrument guide (266).

The robotic arm (200) may comprise a dismountable adapter (250) configured for attachment to an effector end of the existing robotic arm and which adds two or three or more last joints and associated linkages of the robot arm and a new an effector end (262) for attachment to the steerable instrument (100), optionally wherein the adapter (250) comprises an adjustable or non-adjustable supporting arm (230f', 252) attachable at a proximal end to a first link of the adapter (250) and attachable at a distal end to:
- a trocar (264) or a clamp for a trocar (264) and/or
- an instrument guide (266) configured to support a shaft (130) of the steerable instrument (100) or a trocar (264), wherein the supporting arm (230f', 252) maintains the trocar (264) or an instrument guide (266) in non-adjustable or adjustable relation to the adapter (250) linkage, and the direction of the linkage controls the direction of the trocar (264) or an instrument guide (266).

The robotic arm (200) may comprise a supporting arm (230f') that is rigid attachable at a first end to one of the robotic arm (200) linkages (230f) and attachable at a second end to:
- a trocar (264) or a clamp for a trocar (264) and/or
- an instrument guide (266) configured to support a shaft (130) the steerable instrument (100), wherein the supporting arm (230f') maintains the trocar (264) or an instrument guide (266) in fixed relation to the linkage, and the direction of the linkage controls the direction of the trocar (264) or an instrument guide (266).

The robotic arm (200) may comprise a prismatic joint (220g') attached at a first end to one of the robotic arm (200) linkages (230f) and attachable at a second end to:
- a trocar (264) or a clamp for a trocar (264) or,
- an instrument guide (266) configured to slidably support the steerable instrument (100), wherein the trocar (264) or instrument guide (266) is maintained in 1DOF slidable relation to the linkage (230f), such that the direction of the linkage (220g') controls the direction of the trocar (264) or an instrument guide (266), and the prismatic joint (220g) controls an axial (A-A') position of the trocar (264) or instrument guide (266) relative to the steerable instrument (100) shaft (130).

The system may further comprising a control unit (300) configured to output control signals to the robotic arm (200) to effect movements of steerable instrument (100) that include:
- rotation of the shaft (130) around the fulcrum zone (134),
- rotation of the shaft (130) axially (A-A'),
- displacement of the shaft (130) axially (A-A'),
- bending of the bendable distal part (140), and
- rotation of the end effector (150) when the bendable distal part (140) is in a bent position.

The control unit (300) may be configured to determine the position of the fulcrum zone (134) in response to a change in an axial position of the shaft (130), and wherein the output control signals to the robotic arm (200) account for a new position of the fulcrum zone (134) to effect a directional movement of the steerable instrument around a new position of the fulcrum zone (134).

The system may further comprise a manual input unit (400), wherein the control unit (300) is further configured to:
receive a sensor signal from the manual input unit (400),
output a control signal for the robotic arm (200) to control movement thereof responsive to the signal from the manual input unit (400).

The control unit (300) may be further configured to:
transform manual movement sensed by the manual input unit (400) to a corresponding movement of the instrument (200),
optionally to scale a corresponding movement of the steerable instrument (200) compared with a manual movement sensed by the manual input unit (400),
optionally to scale up bending of the bendable distal part (140) of the steerable instrument (200) compared with a corresponding manual movement sensed by the manual input unit (400), and
optionally to dampen a corresponding movement of the instrument compared with the manual movement sensed by the manual input unit (400).

The system may further comprise a contactless measurement unit (450) configured to measure contactlessly features within an operating volume, wherein the control unit (300) is further configured to:
receive a sensor signal from the contactless measurement unit (450),
automatically control movements of the steerable instrument (100) responsive to the signal from the contactless measurement unit (450).

The control unit (300) may be configured to generate control signals for moving the robotic arm (200) using a model of the steerable instrument (100) and one or more (preferably all) parameters relating to: bendable proximal part length, bendable proximal part maximum diameter, bending curvature of the bendable proximal part, position of the BPP-ZOM, position of the BPP-CZOM, distance of BPP to connector, shaft length, shaft diameter, position of the fulcrum zone, bending movement amplification factor, dimension of the fulcrum zone, bendable distal part length, bendable distal part maximum diameter, bending curvature of the bendable distal part, position of the BDP-ZOM, position of the BDP-CZOM distance of BDP to distal tip. For a simplified model, the following parameters of the steerable instrument may be used: shaft length, distance of BPP to connector, distance of BDP to distal tip, position of the fulcrum zone, diameters of the BPP and BDP or the amplification factor; the following optional parameters may be added: the BPP length, the BDP length, the bending curvature of the BPP, and the bending curvature of the BDP.

The control unit (300) may be configured to generate control signals for moving the robotic arm (200) using a model of the steerable instrument (100) that treats bendable proximal part (120) as a joint that moves around a zone of motion (122) that is a zone coinciding with a central axis (A-A') of the shaft where a central axis (112) of the connector (110) intersects at a different connector (110) directions, and optionally that treats the bendable distal part (140) as a joint that moves around a zone of motion (142) that is a zone coinciding with a central axis (A-A') of the shaft where a central axis (152) of the end effector (150) intersects at a different end effector (150) directions.

The model may treat the bendable distal part (140) as a joint that moves around a geometric centre of the zone of motion (142), and wherein the model treats bendable proximal part (120) as a joint that moves around a geometric centre of the zone of motion (122).

The base end (232) of the robotic arm (200) may be attached to a moveable member, and wherein
the position of the moveable member is adjustable,
optionally the angle of the moveable member is adjustable, and
optionally the moveable member is comprised in a gantry, a trolley, or a further robotic arm.

The system may comprise one or more additional robotic arms (200) as defined herein.

A method is provided of controlling a robotic arm (200) in a system described herein to move an attached steerable instrument (100), which method effects movements of steerable instrument (100) that include:
rotation of the shaft (130) around the fulcrum zone (134),
rotation of the shaft (130) axially (A-A'),
displacement of the shaft (130) axially (A-A'),
bending of the bendable distal part (140), and
rotation of the end effector (150) when the bendable distal part (140) is in a bent position.

The movements of steerable instrument (100) may be responsive to a manual input unit (400)

The movements of the steerable instrument (100) may be responsive to a manual input unit (400) are determined using a model of the steerable instrument (100) and one or more (preferably all) parameters relating to:
bendable proximal part length, bendable proximal part maximum diameter, bending curvature of the bendable proximal part, position of the BPP-ZOM, position of the BPP-CZOM, distance of BPP to connector, shaft length, shaft diameter, position of the fulcrum zone, bending movement amplification factor, dimension of the fulcrum zone, bendable distal part length, bendable distal part maximum diameter, bending curvature of the bendable distal part, position of the BDP-ZOM, position of the BDP-CZOM distance of BDP to distal tip. For a simplified model, the following parameters of the steerable instrument may be used: shaft length, distance of BPP to connector, distance of BDP to distal tip, position of the fulcrum zone, diameters of the BPP and BDP or the amplification factor; the following optional parameters may be added: the BPP length, the BDP length, the bending curvature of the BPP, and the bending curvature of the BDP.

FIGURE LEGENDS

FIG. 1A to 1E Different view of a laparoscopic instrument of the prior art for attachment to a da Vinci surgical robotic system (Intuitive Surgical Inc.).

In FIG. 2A, the BPP and a BDP are straight; in FIG. 2B, the BDP is bent responsive to bending of the BPP.

Figure 35:
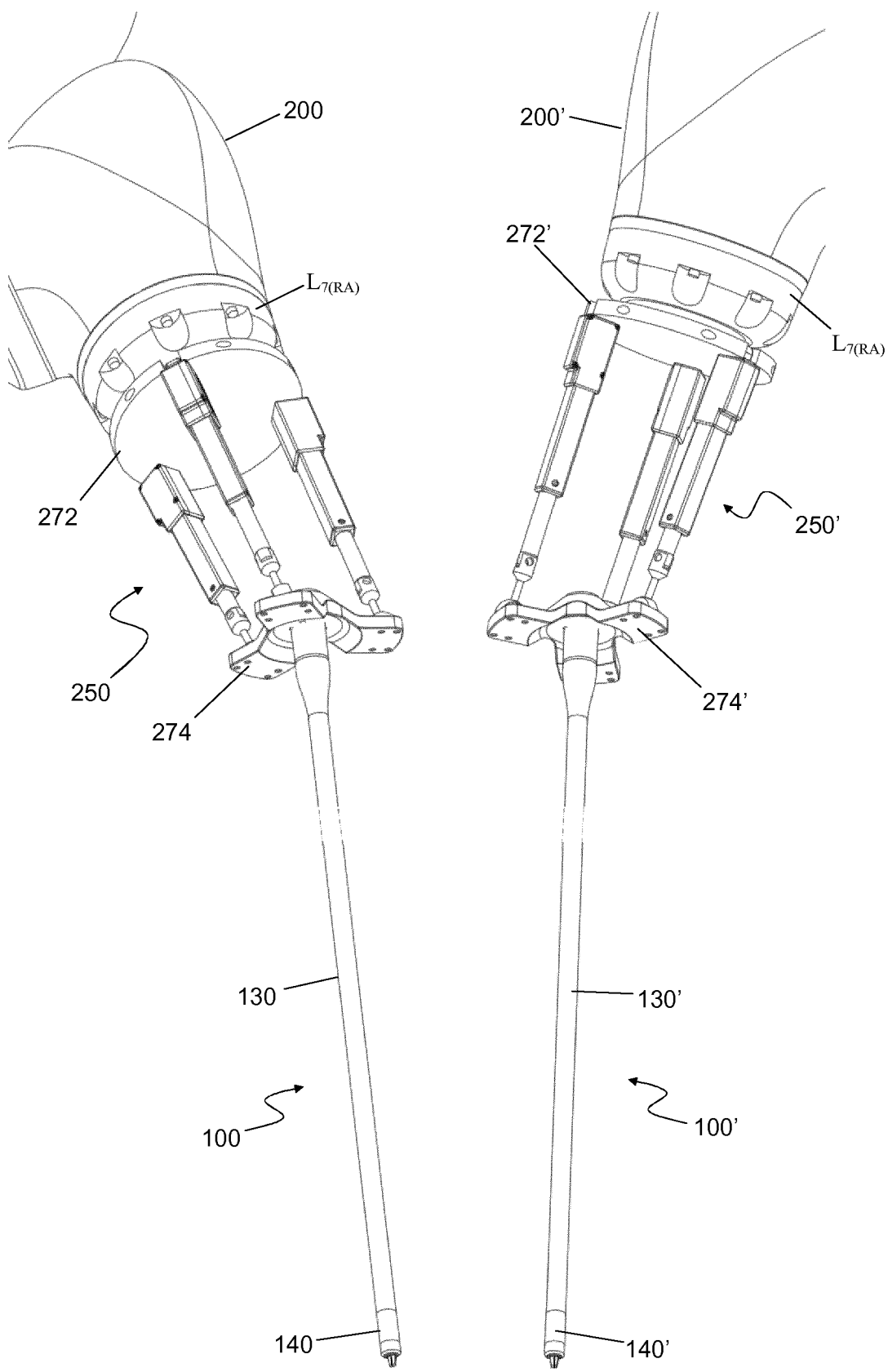
Figure 36:
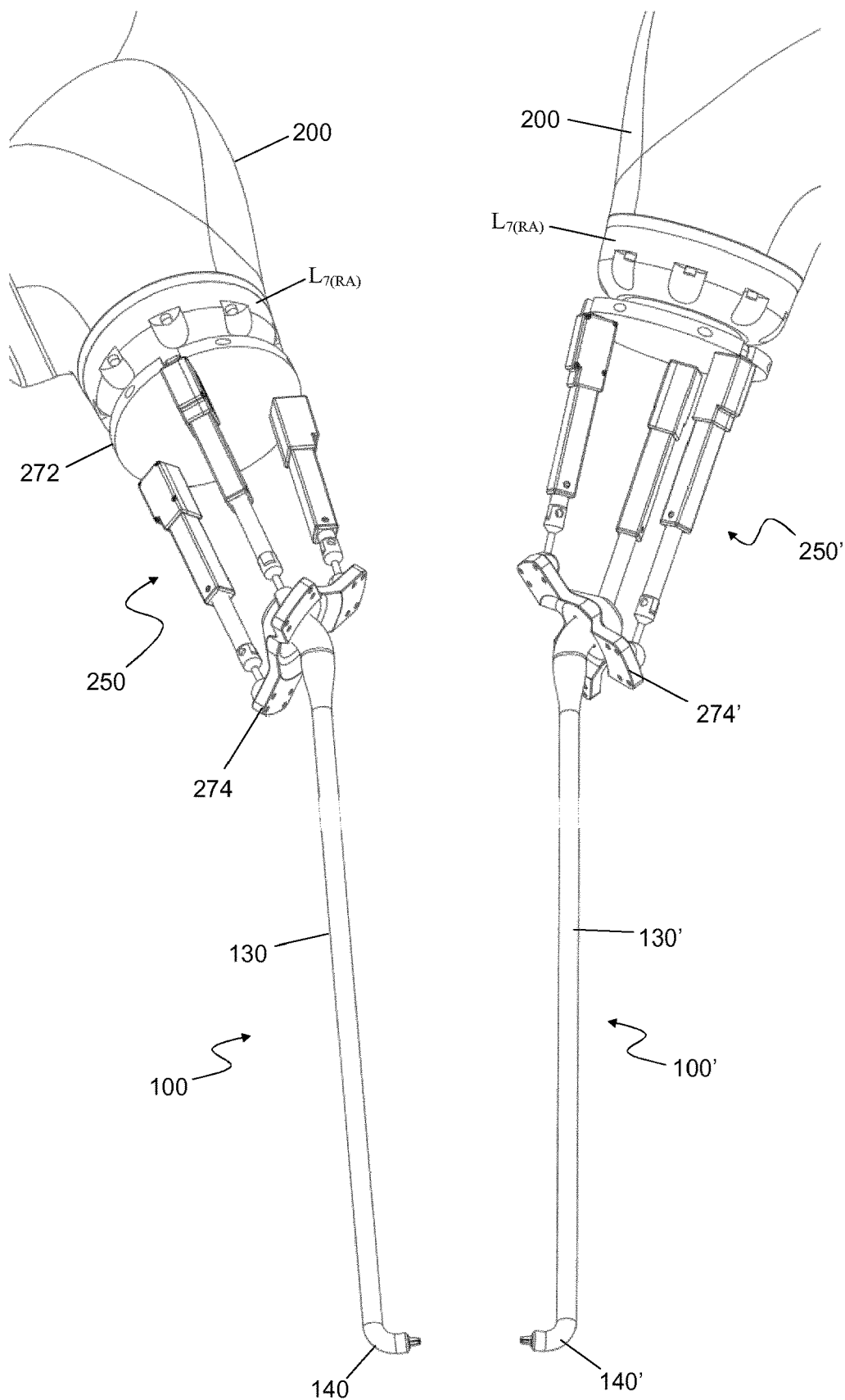
Figure 37:
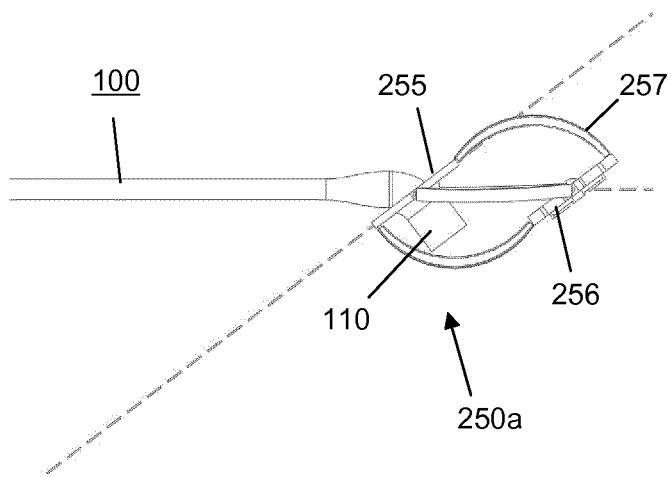
Figure 38:
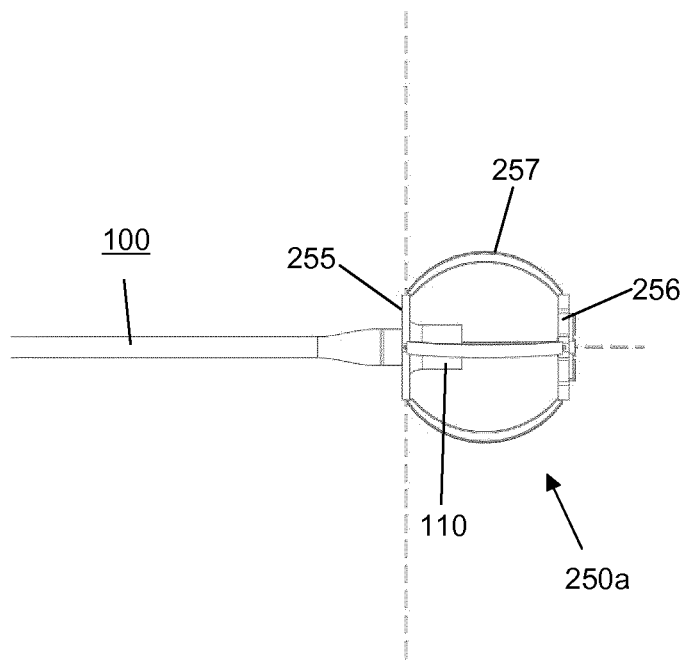
Figure 39:
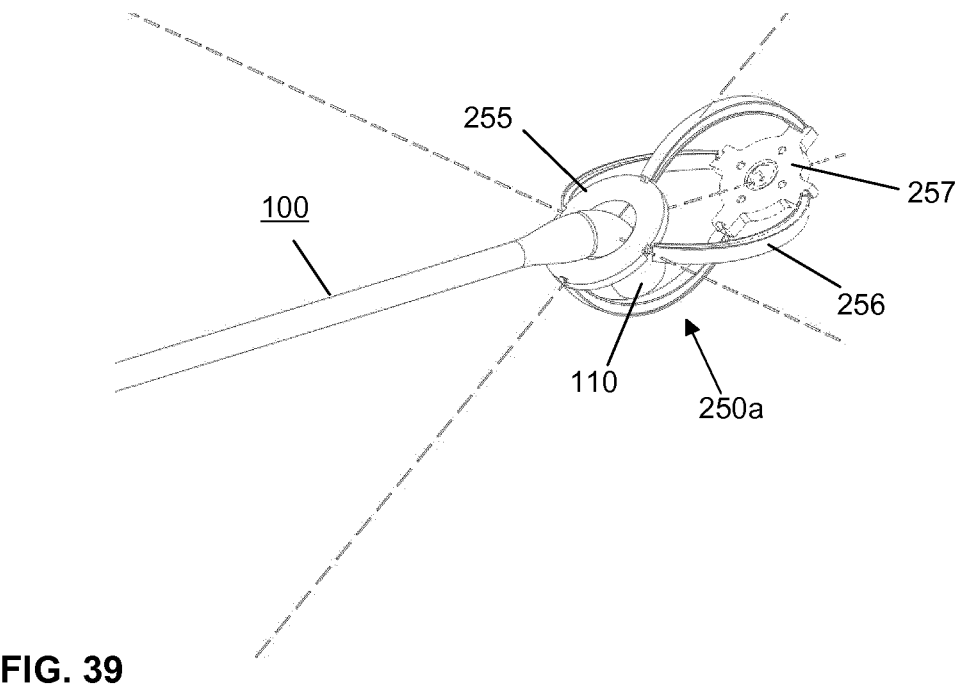
Figure 40:
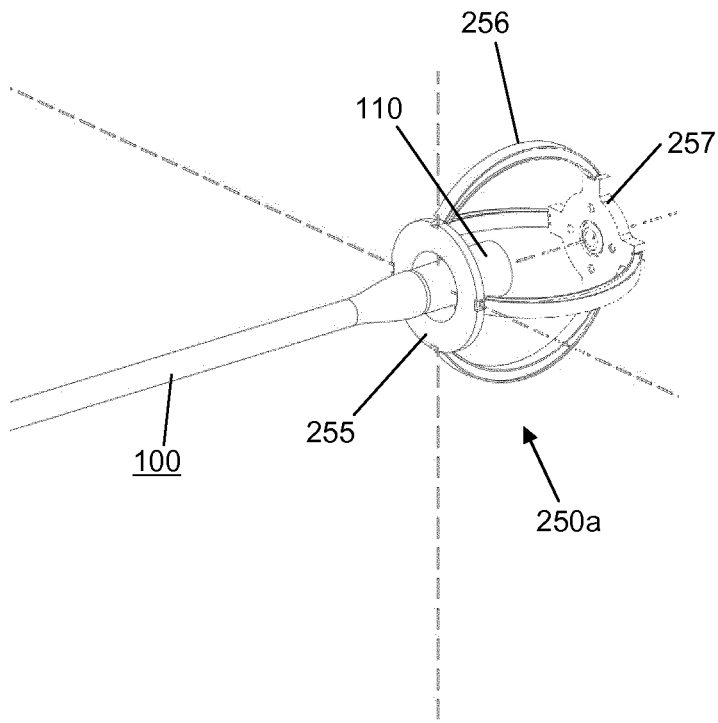

FIGS. 35 and 36 each show two robotic arms (200, 200') in close proximity each provided with an adapter (250, 250').

FIGS. 37 to 40 show different views of an adapter (250a) comprising a pair of plates (255, 256) separated by 4 links (257) each link (257) attached the plate by a revolute joint either side of the link.

Figure 14:
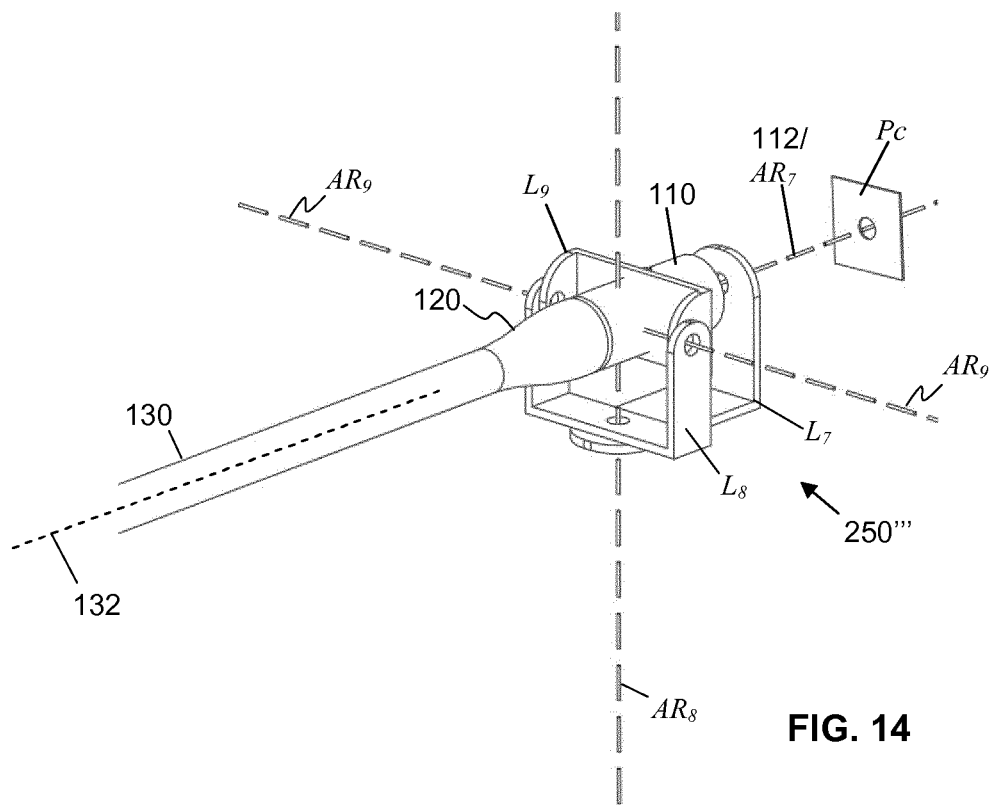
FIGS. 14 to 17 illustrate a configuration of the robotic arm wherein the last two joints ($R_8$, $R_9$) are provided by an adapter, and the distal-most joint ($R_9$) has an axis of rotation that is not parallel with a central axis of the connector.
Figure 15:
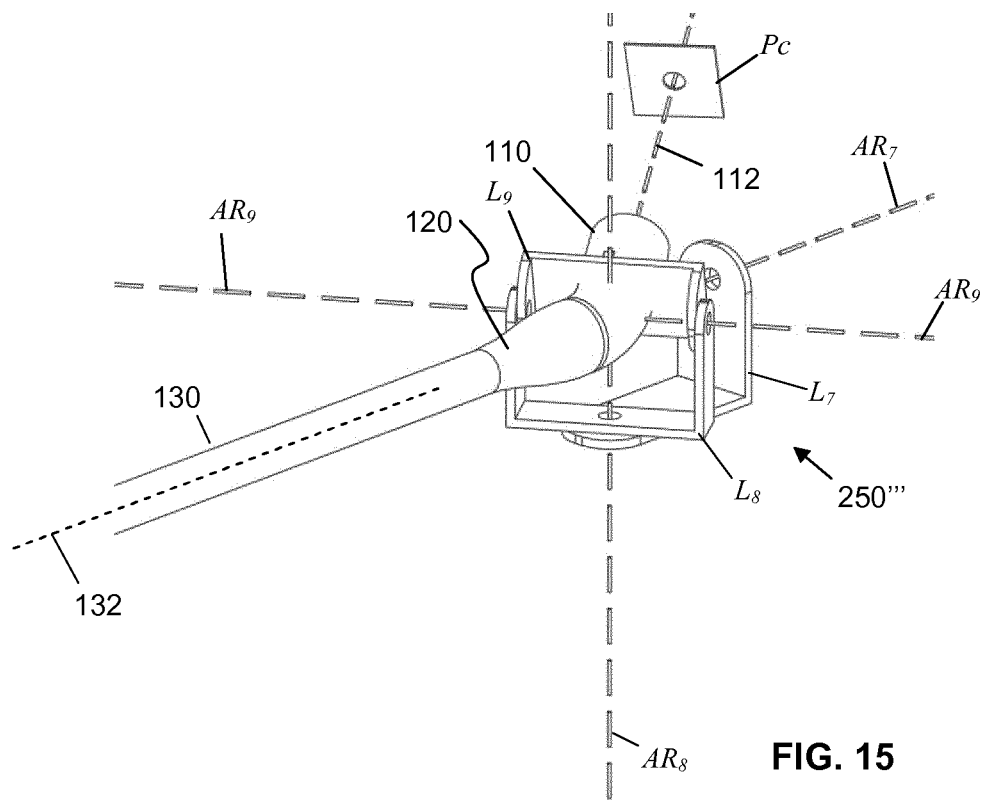
Figure 41:
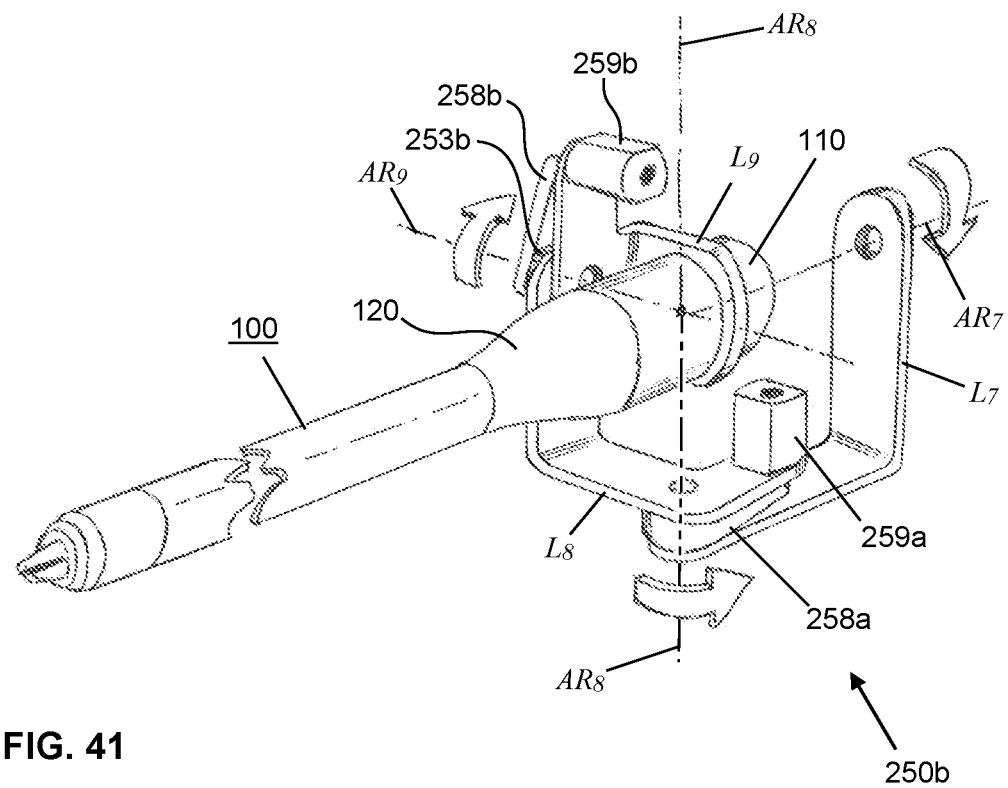
Figure 42:
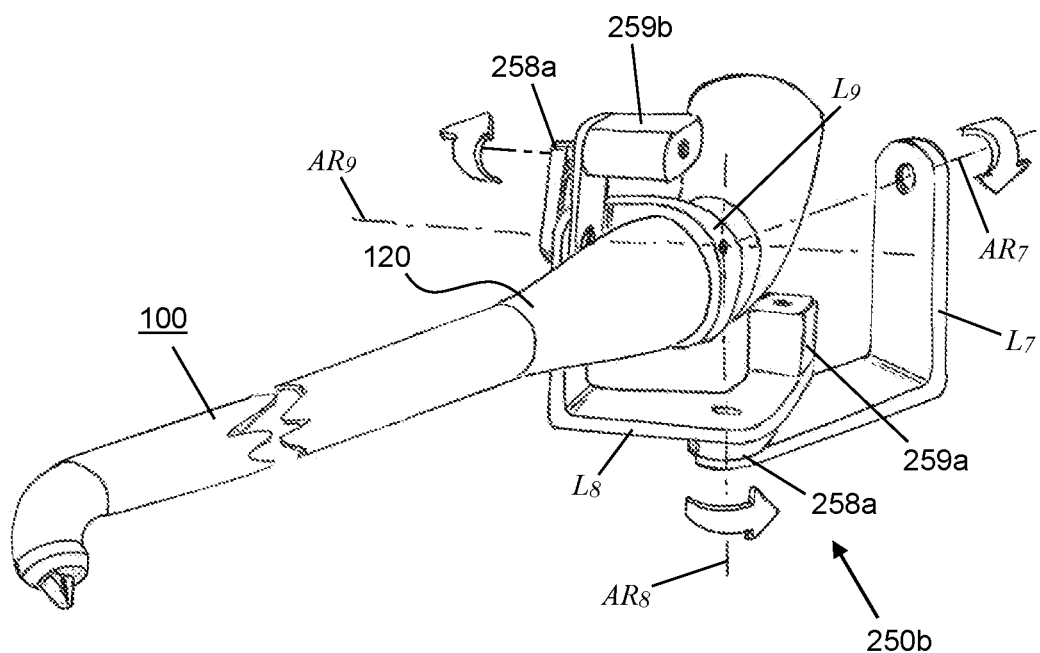

FIGS. 41 and 42 show an implementation of an adapter (250b) according to FIGS. 14 and 15 together with a drive system for each joint.

Figure 26:
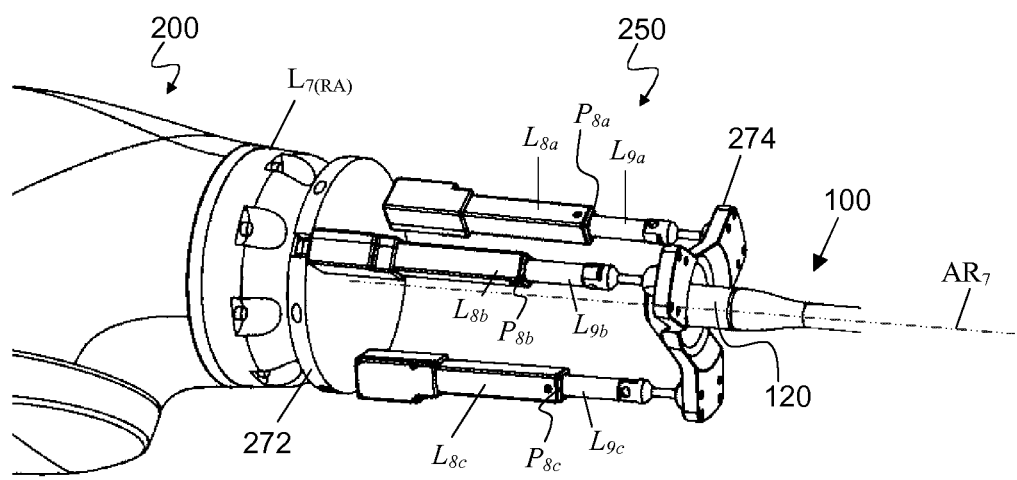
FIG. 26 depicts an adapter (250) comprising three prismatic joints attached at a proximal end to a common waist plate (272) and at a distal end to a common footplate (274) by revolute joints.

FIGS. 43A to D show different actuation positions of the adaptor shown in FIG. 26, wherein the linkage of the robotic arm is attached to a motorised adjustable supporting arm connected to a trocar.

DETAILED DESCRIPTION OF INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal" or "distal to" and "proximal" or "proximal to" are used throughout the specification, and are terms generally understood in the field to mean towards (proximal) or away (distal) from the practitioner's side of an apparatus. Thus, "proximal" or "proximal to" means towards the practitioner's side and, therefore, away from the patient's side. Conversely, "distal" or "distal to" means towards the patient's side and, therefore, away from the practitioner's side.

Provided herein is a steerable instrument controllable by a robotic arm. The steerable instrument has a proximal end and distal end and comprises a shaft, a bendable proximal part (BPP) and a bendable distal part (BDP). It further comprises a connector attached with the BPP configured for dismountable attachment to the robotic arm. It may further comprise an end effector attached to the bendable distal part. The steerable instrument configured such that the bendable distal part bends responsive to bending of the bendable proximal part by the connector, and the distal tip or end effector is rotatable when the bendable distal part is in a bent position by a complementary rotation of the connector. It is further configured such that shaft pivots around a fulcrum zone responsive to movements of the connector. Control of the shaft direction, displacement of the shaft along an axial (A-A') direction, bending of the bendable distal part, and rotation of the distal tip or end effector is realised through robotic movement of the single connector.

The direction of the shaft refers to its angular placement. Changing a direction of the shaft is achieved typically by a pivoted rotation around a fulcrum zone. The fulcrum zone coincides with a longitudinal axis (A-A') of the shaft, for instance, a central longitudinal axis of the shaft. Such movements have two degrees of freedom (2-DOF), and may be known as pitch and yaw. When referring to direction, two degrees of freedom is equivalent to a rotation about two axes. The fulcrum zone is where axes of rotation intersect. The fulcrum zone typically coincides with an entry point to the space being investigated, for instance with a hole made in a wall, membrane or port. The fulcrum is provided by the entry point. Where the steerable instrument is a laparoscopic medical instrument, the fulcrum zone is placed at a bodily incision where the laparoscopic medical instrument is introduced. The minimally invasive instrument is typically enters the body via a trocar—a tube-like port inserted into an incision—that supports the steerable instrument and is amendable to pivoted rotation around the fulcrum point of the incision. Examples of different shaft directions are shown in FIGS. 9A'-C'.

The axial position of the shaft refers to its axial (A-A') positional placement. Changing an axial position of the shaft is achieved typically by displacing the shaft axially in a A-A' direction. Such movement has one degree of freedom (1-DOF), and may be known as axial displacement. The entry point to the working space e.g. a bore hole, maintenance port, or a bodily incision supports the steerable instrument and allows the instrument shaft to slide relative to the entry point. Where the steerable instrument is a minimally invasive medical instrument, the medical instrument is introduced via a bodily incision. The medical instrument is typically enters the body via a trocar—a tube-like port inserted into an incision—that supports the steerable instrument and allows the instrument shaft to slide relative to the trocar.

The direction of the distal tip or end effector refers to its angular placement relative to the shaft. Changing a direction of the distal tip or end effector is achieved primarily by actuation of the BPP that changes the direction of BDP. A central axis (FIG. 2B, 152) of the distal tip or end effector (150) in different directions intersect at a BDP zone of motion, ZOM, (142) that is a zone coinciding with a central axis (A-A') of the shaft. Bending movements of the BDP has two effective degrees of freedom (2-DOF) around its zone of motion, and may be known as effective pitch and effective yaw of the distal tip or end effector that is different from the pitch and yaw of the instrument shaft. Examples of different distal tip or end effector directions are shown in FIGS. 8A'-C'. The inventors have found that a geometric centre of the BDP zone of motion (BDP-CZOM) can be used as an effective fulcrum point to robotically control the direction of the distal tip or end effector, even when the BDP bends along a curve. Advantageously, treating the direction of the distal tip or end effector as pivoting around BDP-CZOM allows the axes of rotation of the last 2 or 3 revolute joints of the robotic arm to intersect at the BPP-CZOM (see FIGS. 11-13), thereby reducing the volume in which the links towards the robotic base move and hence reducing a risk of collision with objects including adjacent equipment and additional robotic arms.

The direction of the connector refers to its angular placement relative to the shaft. Changing a direction of the connector is achieved primarily by the robotic arm. A central axis (FIG. 2B, 112) of the connector (110) in different directions intersect at a BPP zone of motion (122) that is a zone coinciding with a central axis (A-A') of the shaft. Bending movements of the BPP has two effective degrees of freedom (2-DOF) around its zone of motion, and may be known as effective pitch and effective yaw of the connector that is different from the pitch and yaw of the instrument shaft. The inventors have found that a geometric centre of the BPP zone of motion (BPP-CZOM) can be used as an effective fulcrum point to robotically control the direction of the direction of the connector, even when the BPP bends along a curve. Advantageously, treating bending of the connector as pivoting around BPP-CZOM allows the axes of rotation of the last 2 or 3 revolute joints of the robotic arm to intersect at the BPP-CZOM (see FIGS. 11-13), thereby reducing the volume in which the robotic links towards the base move and hence reducing a risk of collision with objects including adjacent equipment and additional robotic arms.

The BPP is disposed at a proximal end of the shaft. It is axially rotationally fixed to the proximal end of the shaft. The BPP may contact the shaft. The BPP may be adjacent to the shaft. Movement of the BPP induces a movement response in the BDP. Movement of BPP in different radial directions and to different bending degrees results in a corresponding change in radial direction and/or degree of bending of the BDP. The BPP may be configured to bend around one or more tandemly arranged joints (e.g. ball and socket joints) each having 2DOF. The BPP may be configured to bend around two or more tandemly arranged joints (e.g. revolute joints offset by 90 deg) each having 1DOF. The number of joints in the BPP may be two or three or more. The BPP may be an extension of the shaft. The BPP may be cylindrical. The BPP may be a cylindrical extension of the shaft. The BPP may be longitudinal. The BPP may be configured to bend along a moulded flexible member as disclosed, for instance, in US 2006/0095074. The BPP may be configured to bend along a curve.

The BDP is disposed at a distal end of the shaft. It is axially rotationally fixed to the distal end of the shaft. The BDP may contact the shaft. The BDP is adjacent to the shaft. The BDP moves in response to movement of the BPP. Movement of BPP in different radial directions and to different bending degrees results in a corresponding change in radial direction and/or degree of bending of the BDP. The BDP may be configured to bend around one or more tandemly arranged joints (e.g. ball and socket joints) each having 2DOF. The BDP may be configured to bend around two or more tandemly arranged joints (e.g. revolute joints offset by 90 deg) each having 1DOF. The number of joints in the BDP may be two or three or more. The BPP may be an extension of the shaft. The BDP may be cylindrical. The BDP may be a cylindrical extension of the shaft. The BDP may be longitudinal. The BDP may be configured to bend along a curve.

The steerable instrument may contain a motion amplifier region having a plane section larger than that of the BDP. In the motion amplifier region, consecutive plane sections gradually increase in size in the distal to the proximal direction. The motion amplifier region may be located within the shaft, or at least partially within the BPP. With the amplifier, movement of the connection and hence of the BPP results in a correspondingly larger movement of the BDP. Bending degree of the bendable distal part responsive to bending degree of the bendable proximal part is amplified by the motion amplifier region. The amplification may result in a distal bending of for instance 90° actuated by a proximal bending of 45°. By increasing the amplification, a bending of 30° could already provide a sufficient distal bending. With 30° of proximal bending, there is less movement required of the joints and as such less space required. An example of a motion amplifier region is set out in WO 2016/091858 A1 which is incorporated herein by reference. Advantageously, the presence of a motion amplifier region reduces the movement volume of the robotic arm and hence reduces a risk of collision with objects including adjacent equipment and additional robotic arms.

The shaft may be rigid or semi-rigid, or may be flexible and become rigid or semi-rigid when co-operating with a rigid or semi-rigid exotube or outer tube, endotube or inner tube. The distal end of the shaft is disposed with the BDP. The proximal end of the shaft is disposed with the BPP. The shaft part is longitudinal, meaning it is longer in one direction. It does necessarily not imply the shaft part is straight. The shaft part may be straight or curved, for instance, having a C- or S-shape. The shaft may be straight. The shaft preferably has a circular transverse (perpendicular to a central axis) profile. The shaft may be cylindrical. The shaft may be non-adjustably rigid.

The steerable instrument is configured for rotation of the distal tip of the BDP or the end effector about its own axis when the BDP is in a bent position, by a complementary rotation of the BPP. It is appreciated that the distal tip of the BDP refers in this context to the distal terminal end of the BDP.

The distal tip of the BDP may be provided with an end effector. The end effector may be rotationally fixed in relation to the BDP, and the end effector is rotatable when the BDP is in a bent position, by a complementary rotation of the BPP. The end effector may be directly attached to the distal end of the BDP (without a coupling).

The steerable instrument end effector may comprise any suitable tool for a remotely controlled application, such as a screw driver, abrasive pad, drill bit, gripper, pliers, cutting scissors, camera and the like. The steerable instrument end effector may be any tool useful in a surgical procedure, tasks as gripper, pliers, cutting scissors, needle holder, retractor, camera needle, (aspiration) catheter, electrical catheter, optical (laser) fiber, ultrasound therapy, measurement probe (temperature, pH, pressure, electrophysiology), stapler, drill, electro-coagulator, HF, clip applier, fluid port and the like.

The term end effector also includes a coupling for attachment to a tool such as mentioned above. The coupling may be rotationally fixed in relation to the BDP, and the coupling is rotatable when the BDP is in a bent position, by a complementary rotation of the BPP. A tool mounted to the coupling is rotationally fixed in relation to the BDP.

Rotationally fixing the coupling or end effector relative to the BDP may be achieved using a permanent (non-adjustable) connection or joint, or by means of a lockable element configured to allow rotational adjustment of and to rotationally fix the coupling or end effector in rotational relation to the BDP.

The end effector may be actuatable by means of a cable attached at a distal end to the end effector (e.g. gripper, pliers, cutting scissors). At the proximal end, the cable may be attached to an actuating element, such as a lever or slider. At the proximal end, the cable may be provided with an attachment element such as a loop or sphere for coupling with an actuating element. The cable may be disposed within a lumen of the steerable instrument. The actuating element may comprise an annular collar provided at a proximal end of the instrument, for instance, around a cylindrical portion disposed between the BPP and the connector. Displacement of the annular collar actuates the end effector. The end effector may be actuated using an electrical conductor when the end effector is an electrically powered device or provides electrical signals such as a motor, camera, electro-coagulator, HF, measurement probe.

The steerable instrument further comprises a connector configured for dismountable attachment to the robotic arm, more in particular to a fitting on the robotic arm. The connector is rotationally fixed in relation to the BPP. The connector is rotationally fixed in relation to the proximal terminal end or tip of BPP. The connector is attached fixed in relation to the proximal terminal end or tip of BPP. The connector may be provided attached to the proximal terminal end or tip of BPP. The connector may be provided attached to the aforementioned cylindrical portion. Rotationally fixing the connector relative to the BPP proximal terminal end or tip may be achieved using a permanent (non-adjustable) connection or joint, or by means of a lockable element configured to allow rotational adjustment of and to rotationally fix the connector in rotational relation to the BPP.

The connector may comprise a rigid member. The rigid member is configured for dismountable attachment to a complementary fitting on the robotic arm. The rigid member is configured for non-rotational dismountable attachment to a complementary fitting on the robotic arm. The rigid member is configured for displaceable dismountable attachment to a complementary fitting on the robotic arm. The rigid member is configured for non-rotational dismountable attachment to a complementary fitting on the robotic arm. The connector may comprise a cylindrical form, as shown, for instance, in FIGS. 2A and 2B.

Figure 2A:
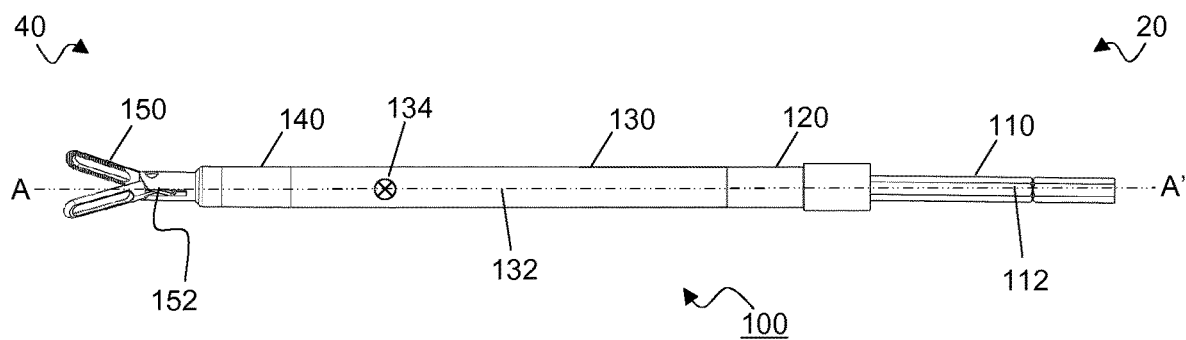
FIGS. 2A and 2B are illustrations of a robotic controllable steerable instrument as described herein.
Figure 2B:
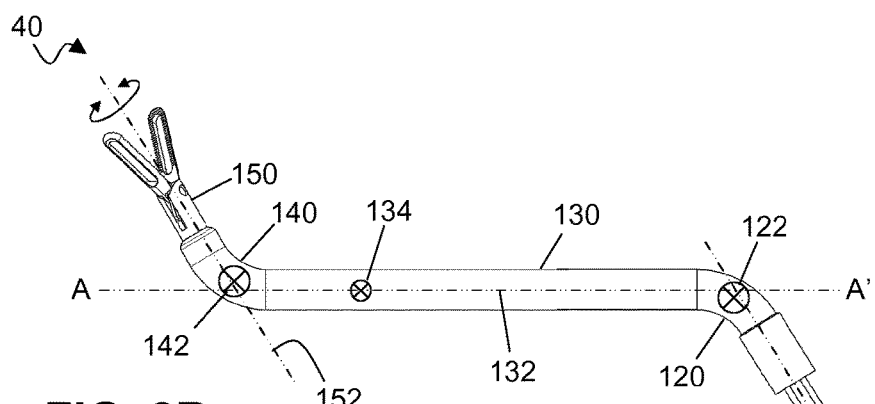

The connector that is a rigid member may have a straight cylindrical form, as shown, for instance, in FIGS. 2A and 2B. The connector that is a rigid member may have another shape, such as L-shape, C-shape, F-shape.

It is understood that the complementary fitting on the robotic arm is disposed in fixed rotational and positional relation to the last (distal-most) linkage in connection with the distal most joint (e.g. $R_7$ in FIGS. 5, 7, 8A-C, 9A-C, 10 to 13) of the robotic arm (including any optional adapter as shown, for instance in FIGS. 10 to 27). The connector of the steerable instrument is configured such when it engages with the complementary fitting of the robotic arm, it is maintained in fixed rotational and positional relation with the complementary fitting; thus rotational and positional movements of the complementary fitting are directly transmitted to the connector.

It is appreciable that the attachment to the robotic arm is to the effector end of the robotic arm, typically in connection—in a straight line or at an angle—with the end joint. It is appreciated that the complementary fitting on the robotic arm may be realised by an adapter described elsewhere herein.

The BDP is configured to move omni-directionally i.e. in any radial direction while the shaft is rotationally fixed. BDP is preferably configured to move in any radial direction (about 360° with respect to central longitudinal axis (A-A) of the shaft part) while the shaft is axially-rotationally fixed. The BDP may be configured to bend along a curve. It might be distinguished from classical minimally invasive tools in that it may be absent of revolute joints. The movement response of the BDP may be:
  a change in degree of bending within a "bending plane" that is a plane parallel to and contacting a central longitudinal axis (A-A') of and extending from the shaft,
  a change direction of the bend; it amounts to a change in direction of the bending plane around the shaft central longitudinal axis (A-A') when the BDP lies along said bending plane.

Similarly, the BPP, is configured to move omni-directionally i.e. in any radial direction while the shaft is rotationally fixed. BPP is preferably configured to move in any radial direction (about 360° with respect to central longitudinal axis (A'-A) of the shaft part) while the shaft is axially-rotationally fixed. The BPP may configured to bend along a curve. It might be distinguished from classical minimally invasive tools in that may be absent of revolute joints.
  The movement response of the BPP may be:
  a change in degree of bending within a "bending plane" that is a plane parallel to and contacting a central longitudinal axis of and extending from the shaft,
  a change direction of the bend i.e. of the distal tip or end effector; it amounts to a change in direction of the bending plane around the shaft central longitudinal axis (A-A') when the BPP lies along said bending plane.

The combination of movements of the steerable instrument facilitates a rotation of BPP at its tip or of the end effector while the BPP is in a bent position that is transmitted via a rotation of the shaft to the BDP that causes rotation of the BDP tip or end effector while the BDP is in a bent position. With such rotation of the tip or of the end effector, the direction of the bending plane can be maintained constant.

The combination of the movement of steerable instrument further facilitates a change in direction of the BDP tip or end effector while the shaft is in a fixed rotational position. With such movement, the bending plane rotates around the shaft central longitudinal axis (A-A') while the shaft itself does not rotate.

To control the BDP responsive to movements of the BPP, steering wires which are known as longitudinal members (LMs) are provided. The LMs pass through the shaft, BDP and BPP. The LM controls the BDP by pulling or pushing. The steerable instrument comprises a set of longitudinal members (LM) each having a proximal end and a distal end, arranged in a longitudinal direction around a fictive tube. A plane section of at least one LM may demonstrate an anisotropic area moment of inertia; the plane section of the LM may have a square, rectangular, serif letter "I", or circular segment profile, optionally wherein one or more of the profile corners are pointed or rounded-off. The LMs may be cut from a tube or provided as separate strands. With this arrangement, the tip (distal terminal end) of the BDP moves with equal ease in any direction i.e. there is no singularity. The movement response is proportion to the degree of actuation. An example of a transmission mechanism has been described in WO 2009/098244.

The BPP and BDP may each be provided with one or a plurality of tandemly arranged pivoting joints. The pivoting joints may be formed by a set of longitudinal member (LM) guides present in each of the BPP and BDP. An LM guide comprises a body having a proximal side, a distal side and an outside edge, wherein the body of the LM guide comprises a set of channels arranged around a fictive tube. Each channel passes from the proximal side to the distal side of the body. Each channel is configured to retain an LM of a set of LMs in a fixed radial position around the fictive tube. Each channel may further by configured to provide a discrete constraining point to axially rotationally constrain an LM. At least one or two of the LM guides in the set may be articulated LM guides tandemly arranged and are mutually articulated, thereby supporting bending of the LMs in the BPP and BDP. The number of articulated LM guides in the BPP may be at least 1 or 2 (e.g. 2, 3, 4, 5, 6, 7, 8 or more), preferably at least 5; where there is at least 2, the BPP may bend along a curve. The number of articulated LM guides in the BDP may be at least 1 or 2 (e.g. 2, 3, 4, 5, 6, 7, 8 or more), preferably at least 5; where there are at least 2 LM guides, the BDP may bend along a curve. The articulated LM guides are in pairwise mutual contact through a pivot joint. The pivot joint may comprise a ball and socket joint, a flexible part, such as a rubber or silicone element, or a stack of spherical bodies. An arrangement of LMs and LM guides, and of a transmission mechanism for a steerable instrument have been described in WO 2016/030457 and WO 2016/091856, and are incorporated by reference herein.

In an alternative arrangement, the BPP and BDP may each be provided with a sleeve containing a plurality of arc shaped discrete slits each provided essentially perpendicular to a longitudinal axis of the BPP or BDP. Each slit may span an angle of around 150 to 210 deg. Advancing along the BPP or BDP, an orientation of a slit may change with respect to a previous slit. Preferably, each slit spans an angle of around 180 deg, and the orientation alternates between 0 and 180 deg advancing along the BPP or BDP. The sleeve supports to the LMs, while the slits allow bending of the BPP or BDP in any direction.

The steerable instrument may be that described in, for instance, WO 2009/098244, WO 2016/030457, WO 2016/091857, WO 2016/091858.

The minimally invasive instrument typically, but not necessarily enters the body via a trocar—a tube-like port inserted into an incision. The trocar is configured to receive the shaft of the steerable instrument; it is provided with a trocar passage into which the steerable instrument can axially slide and rotate, to support the steerable instrument allowing axial (A-A') displacements and also to provide a fulcrum point to change direction of the steerable instrument. A trocar is known in the art. Where the trocar can pivot freely around the incision, so the steerable instrument can pivot around the fulcrum zone in concert with the trocar.

Where direction of the trocar is robotically controlled, the trocar may fix the direction of the steerable instrument, and pivoting control of the steerable instrument around the fulcrum zone is robotically controlled. The trocar may be attachable (e.g. via a clamp or coupling) in fixed relation to one of the linkages of the robotic arm i.e. held in non-rotational and non-displaceable relation thereto. The linkage may be any before the third revolute joint from the effector end (e.g. 230f in FIG. 3H). The trocar may be attachable via a 1DOF joint (e.g. a primastic joint) relation to one of the links of the robotic arm i.e. held in non-rotational and 1DOF displaceable relation thereto. The direction of the link can be adjusted so as to change the direction of the trocar. The 1DOF joint where present can change the position of the trocar along the instrument shaft. If the surgeon would wish to pivot the steerable instrument around the fulcrum zone, the, robotic arm changes the direction of the trocar to correspond with the required direction of the steerable instrument, while still controlling the direction of the shaft, end effector, rotation of the end effector and axial displacement of the shaft via the connector.

Figure 3:
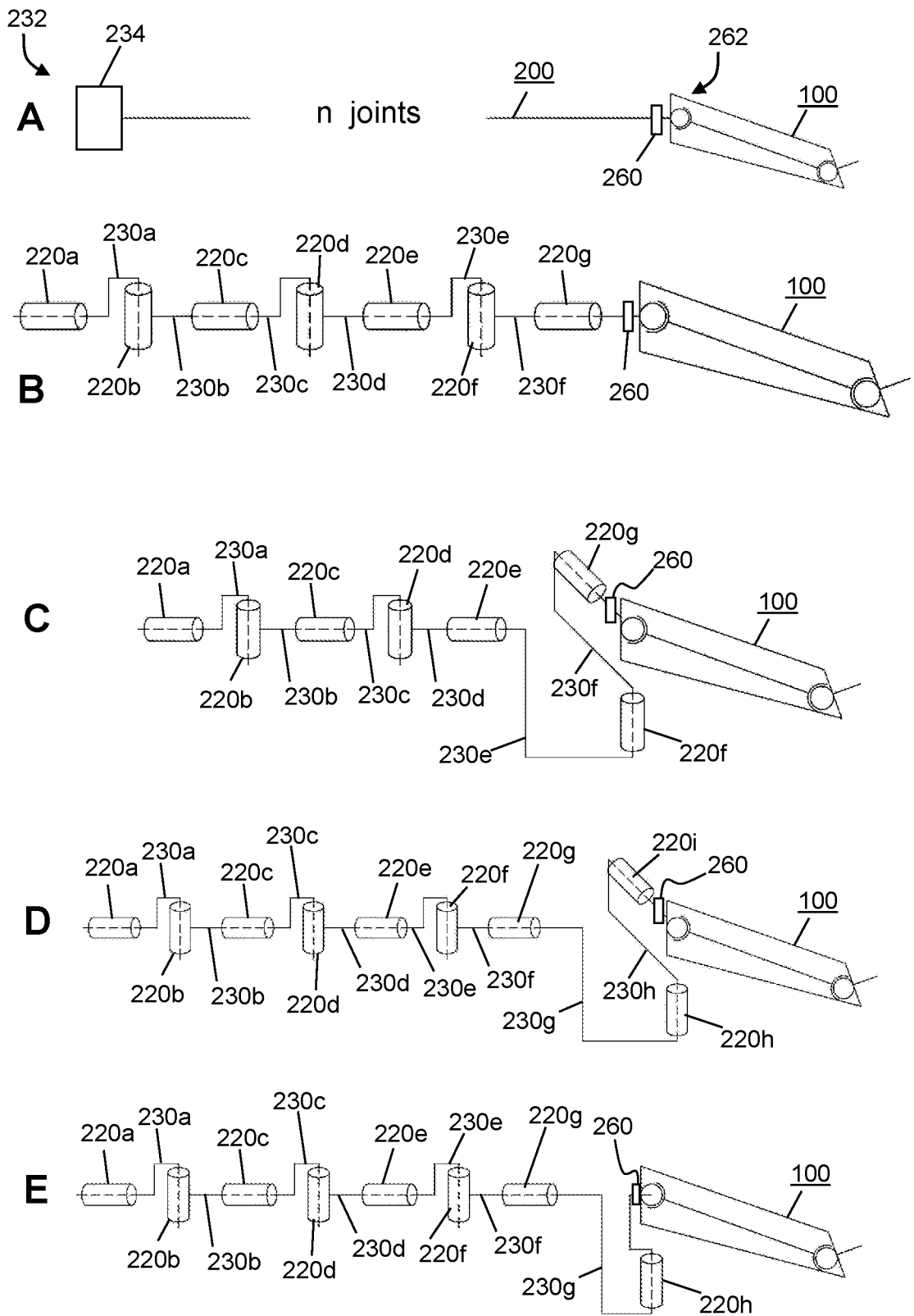
FIG. 3A is a schematic representation of a robotic arm having n joints which may be revolute and/or prismatic joints.
FIGS. 3B to 3R depict schematically different configurations of a robotic arm attached to a steerable instrument.
Figure 3:
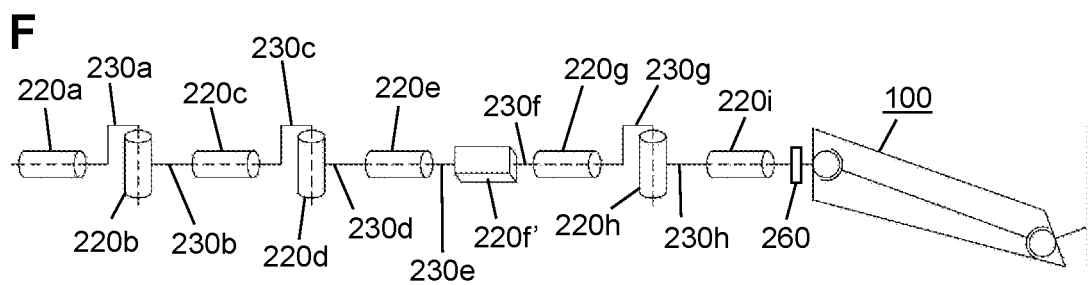
Figure 3:
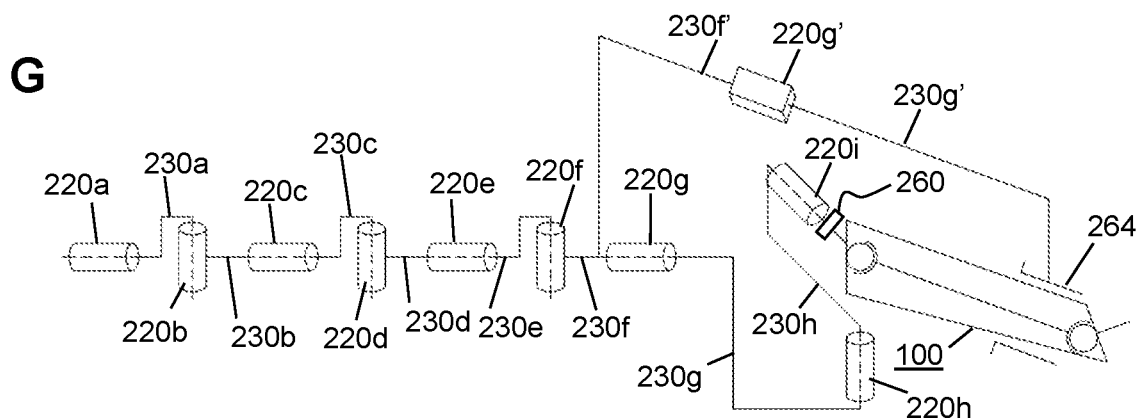
Figure 3:
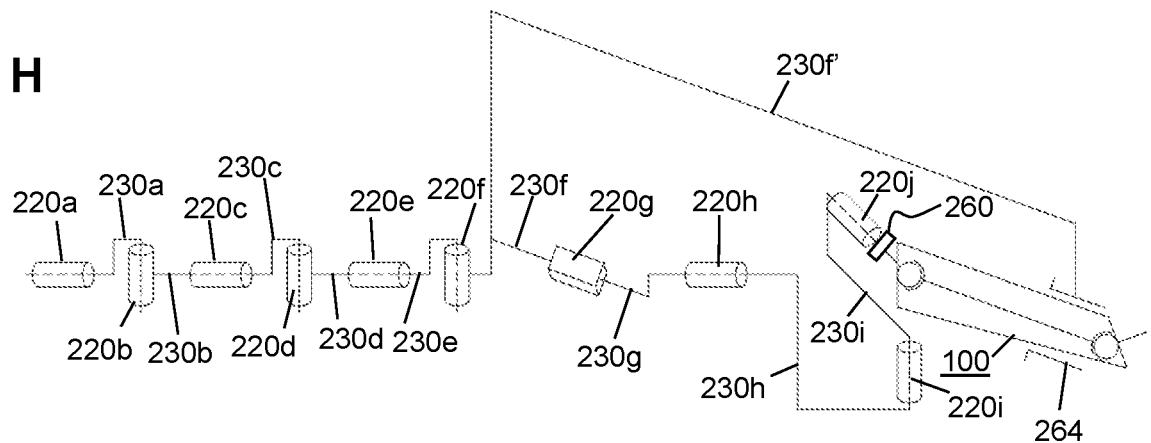
Figure 3:
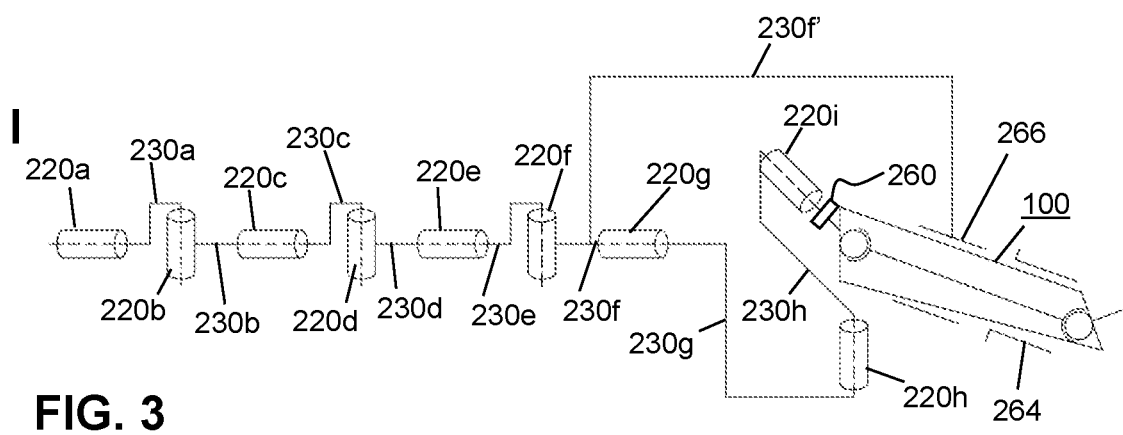
Figure 3:
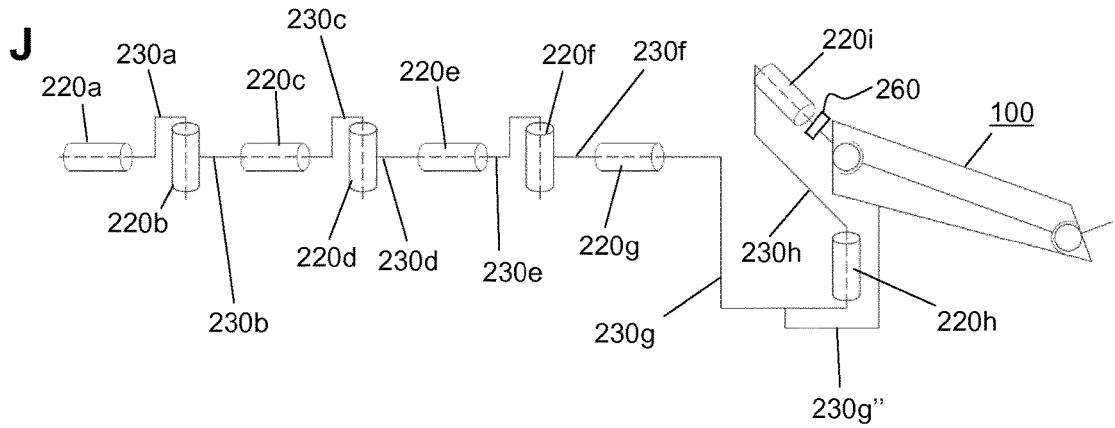
Figure 3:
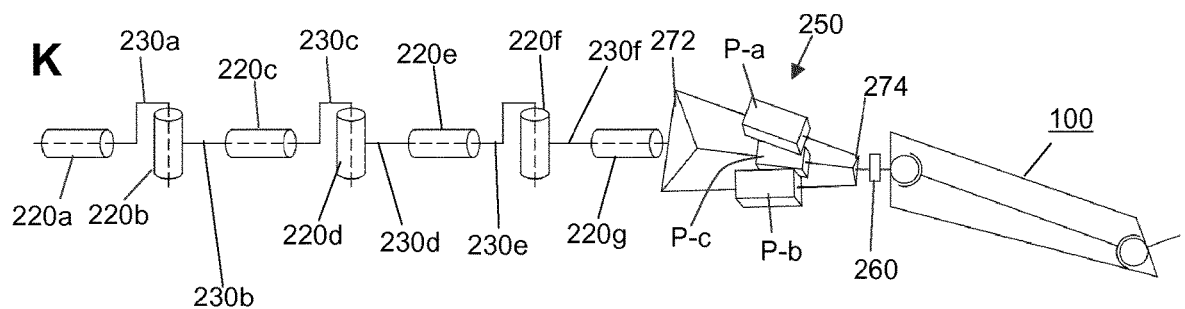
Figure 3:
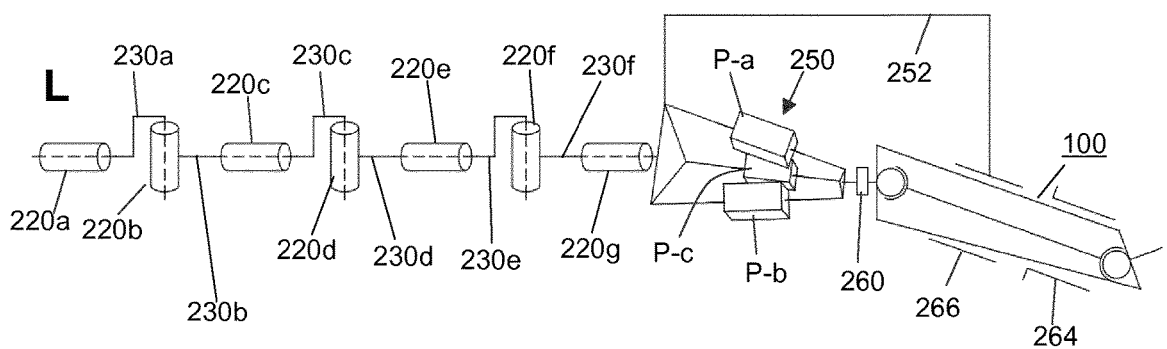
Figure 3:
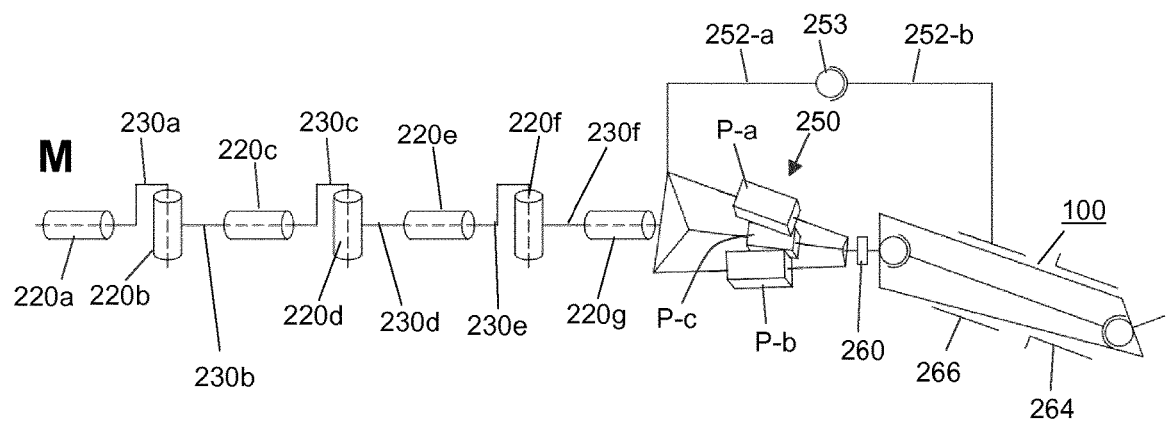
Figure 3:
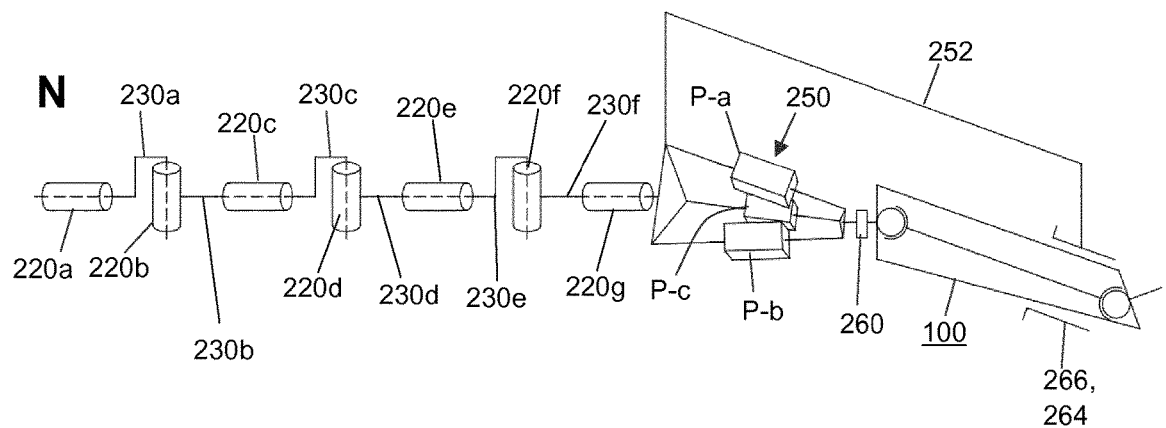
Figure 3:
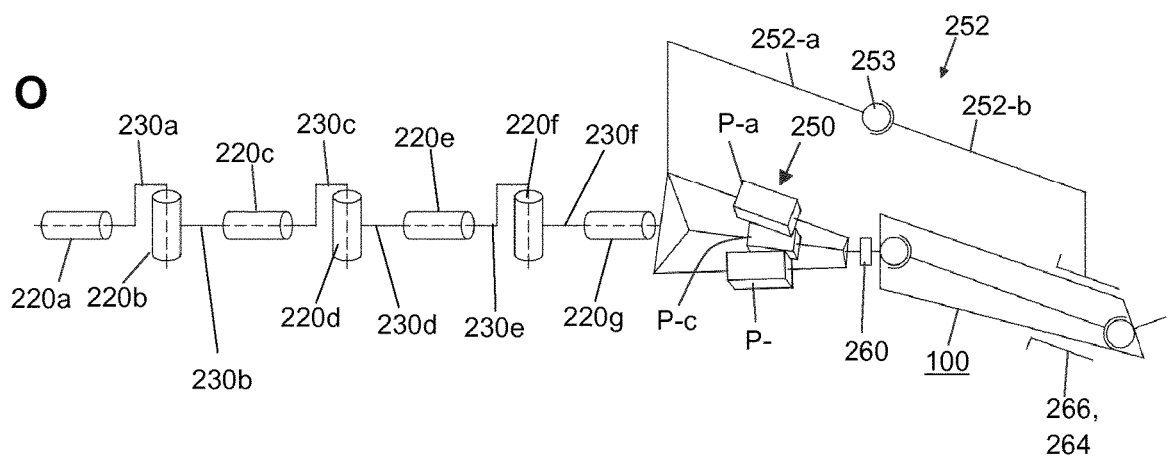
Figure 3:
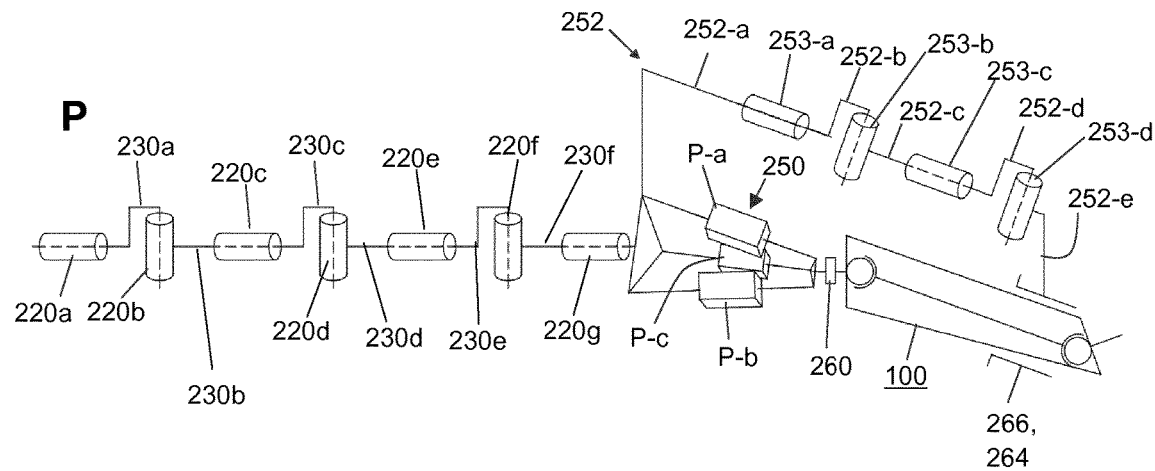
Figure 3:
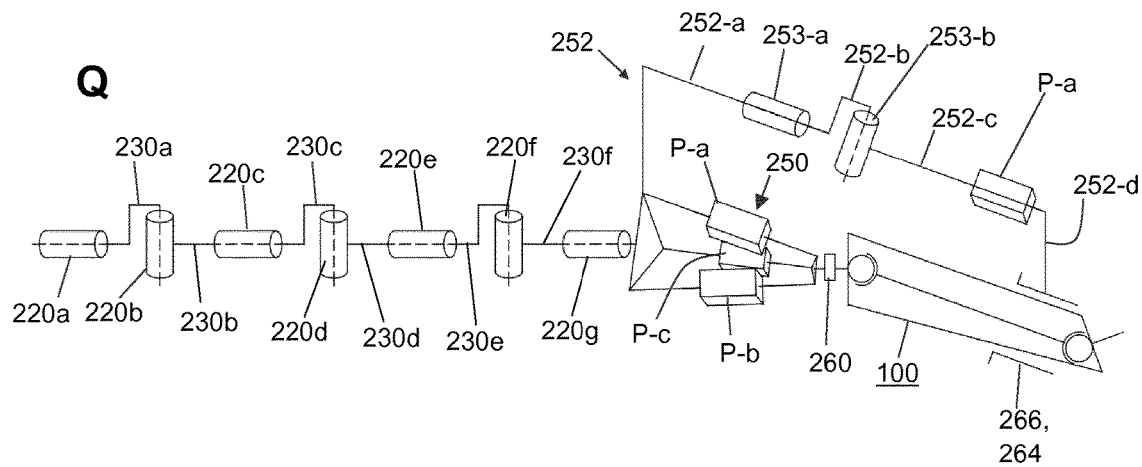
Figure 3:
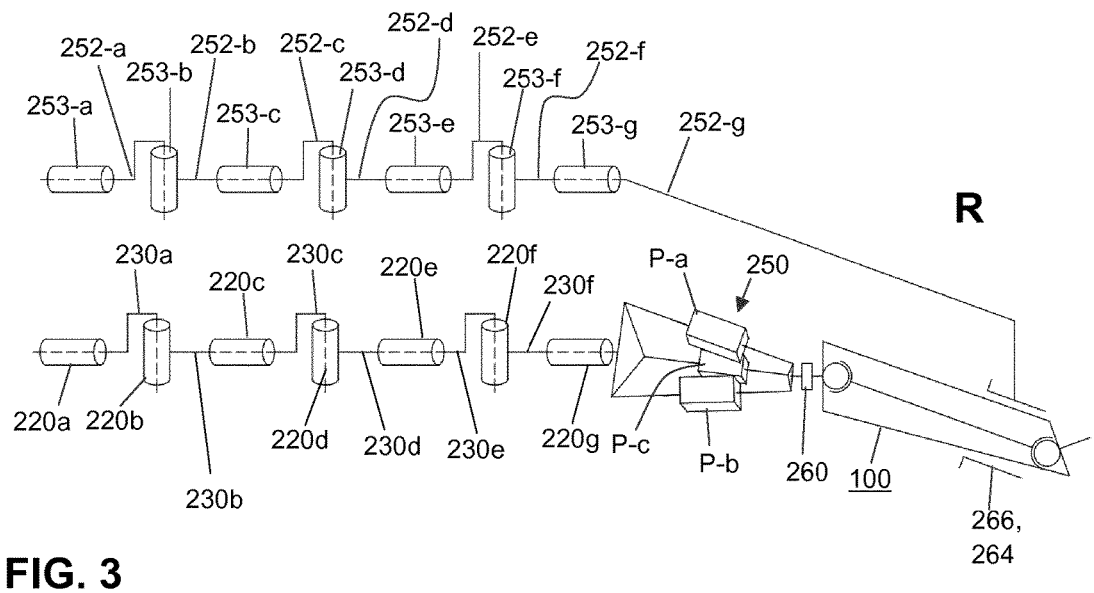

The trocar may be attachable in fixed relation to one of the linkages of the robotic arm via a supporting arm; it may be rigid, non-adjustable or adjustable. One end of the supporting arm is attached or attachable to robotic arm linkage. The linkage may be any before the third revolute joint from the effector end (e.g. 230f in FIG. 3H The other end of the supporting arm is attached or attachable (e.g. via a clamp or coupling) to the trocar into which the steerable instrument is slidably mountable. Via the supporting arm, the trocar when attached is in fixed positional and rotational relation to the robotic arm linkage. The trocar may be attached to the supporting arm using a clamp or coupling or instrument guide. An example of a robotic arm configuration provided with a steerable trocar (264) in fixed positional and rotation relation with the linkage is shown in FIG. 3H.

The trocar may be attachable in 1DOF or more relation to one of the linkages of the robotic arm. The trocar may be attachable in 1DOF slidable relation to one of the linkages of the robotic arm via two rigid arms that form an adjustable supporting arm. One end of a first rigid arm is attached or attachable to robotic arm linkage and the other end of the rigid arm is attached or attachable to the 1DOF slidable joint. The linkage may be any before the third revolute joint from the effector end (e.g. 230f in FIG. 3G or 3H). One end of the second rigid arm is attached or attachable to the 1DOF slidable joint. The other end of the second rigid arm is attached or attachable (e.g. via a clamp) to the trocar into which the steerable instrument is slidably mountable. Via the rigid arms, the trocar when attached is in fixed 2DOF positional and rotational relation to the robotic arm linkage, but is slidable in 1DOF. The trocar may be attached to the adjustable supporting arm using a clamp or coupling. An example of a robotic arm configuration provided with a steerable trocar (264) in fixed positional and rotation relation with the linkage and in 1DOF slidable relationship thereto is shown in FIG. 3G. An example of a robotic arm configuration provided with a steerable trocar (264) attached by an adjustable supporting arm that sets the trocar (264) in positional and rotation relation with a linkage ($L6_{(RA)}$) of the robotic arm (200) is shown in FIGS. 43A to D.

The shaft of the steerable instrument may be supported by an instrument guide in order to provide additional stability. The instrument guide is configured to receive the shaft of the steerable instrument or a trocar into which the steerable instrument can axially rotate and optionally slide, and to support instrument direction. The instrument guide may fix the direction of the steerable instrument and/or of the shaft. The instrument guide may or may not allow axial (A-A') rotations of the instrument shaft. The instrument guide may or may not allow axial (A-A') sliding of the instrument shaft relative to the instrument guide. The instrument guide may fix an axial (A-A') sliding of the instrument shaft relative to the instrument guide. The instrument guide may fix an axial (A-A') rotation of the instrument shaft relative to the instrument guide. Examples of instrument guides (266) are shown in FIGS. 3I, 3L, 3M, 16, 17, 22-25, 31-34.

The instrument guide may be rigidly attached to one of the linkages of the robotic arm i.e. held in non-rotational and non-displaceable relation thereto. The direction of the linkage can be adjusted by the robotic arm so as to change the direction of the instrument guide. If the surgeon would wish to pivot the steerable instrument around the fulcrum zone, the robotic arm would change the direction of the instrument guide to correspond with the required direction of the steerable instrument, while still controlling the direction of the shaft, end effector, rotation of the end effector and axial displacement of the shaft via the connector.

The instrument guide may be attachable in relation to one of the linkages of the robotic arm via a supporting arm; it may be held fixed, rigid, non-adjustable or adjustable relation. One end of the supporting arm is attached or attachable to robotic arm linkage, also known herein as an anchoring robotic arm linkage. The other end of the supporting arm is attached or attachable to the instrument guide into which the steerable instrument is mountable, optionally slidably. Via the supporting arm, the instrument guide when attached is in fixed or adjustable positional and rotational relation to the robotic arm linkage. An example of a robotic arm configuration provided with an instrument guide (266) is shown in FIG. 3I. Examples of supporting arms (252) are shown in FIGS. 3I, 3L to 3R, 16, 17, 22-25, 31-34.

The supporting arm (252) may be fixed i.e. non-adjustable; for instance, the orientation of the instrument guide (266) and/or instrument guide body with respect to the anchoring robotic arm linkage is fixed and non-adjustable.

The supporting arm (252) may be adjustable; for instance, to adjust orientation of the instrument guide (266) and/or instrument guide body with respect to the anchoring robotic arm linkage. The adjustable supporting arm may be configured to adjust an orientation of the instrument guide and/or instrument guide body with respect to the anchoring robotic arm linkage. Once the orientation has been set, the adjustable supporting arm is configured to lock the orientation. The adjustable supporting arm may comprise two or more rigid linkages mutually connected by lockable joint, that offers 1 or 2 degrees of freedom (DOF) of movement, such as a ball-and-socket joint.

Example of adjustable supporting arms (252-a, -b) are shown in FIGS. 3M, 3O to 3R, 22-25, 31-24 which depict an instrument guide (266) as part of an adapter (250) having an instrument guide (266) body provided with a guide slot that supports the shaft of the steerable instrument. The shaft (130) of the steerable instrument is maintained in fixed axial rotation with respect to the instrument guide (266) body. The instrument guide (266) body is attached to an adjustable supporting arm (252), having two rigid linkages (252-a, 252-b) mutually connected by lockable ball and socket joint (253), that offers 2 degrees of freedom (DOF) of movement between the rigid linkages.

The adjustable supporting arm (252-a, -b) may be adjustable using one or more powered actuators such as a motor (e.g. servo motor, linear actuator). A pair of rigid linkages (252-a, 252-b) may mutually connected by a joint each driven by a powered actuator. For instance, a plurality of rigid linkages may connected in series by three joints, two of which are revolute and driven by a servo motor and one of which is prismatic and driven by a linear actuator; this might be relevant when the instrument guide is attached to a trocar. In FIG. 3P, a powered adjustable supporting arm is depicted having 5 linkages and 4 revolute joints. In FIG. 3Q, a powered adjustable supporting arm is depicted having 4 linkages and 2 revolute joints and one prismatic joint. In FIG. 3R, a powered adjustable supporting arm is depicted having 7 linkages and 7 revolute joints.

In FIGS. 22 to 25 a proximal end of the adjustable supporting arm (252) is attached (251) to a linkage ($L_7$) of the adapter (250). It is attached (251) in fixed relation to the $1^{st}$ (proximal most) linkage ($L_7$) of the adapter (250). In FIGS. 31 to 34 a proximal end of the adjustable supporting arm (252) is attached to the waist plate (272). It is attached (251) in fixed relation to the waist plate (272).

In FIGS. 16, 17, 22 to 25 the last three axes intersect (e.g. $AR_7$, $AR_8$ and $AR_9$) at BPP (120) of the steerable instrument (100), in particular at the zone of motion (122), more precisely at the BPP-CZOM.

The instrument guide (266) may be provided as part of an adapter (250, FIGS. 16, 17, 22-25, 31-34) described later below, configured for attachment to an effector end of an existing robotic arm to create a new effector end for attachment to the steerable instrument (100). The adapter (250) may be provided at the proximal end with a $1^{st}$ fitting adapted for dismountable attachment in fixed revolute relation to the end effector of the robotic arm. The adapter (250) may be provided with at the distal end with a $2^{nd}$ fitting adapted for dismountable attachment in fixed revolute relation to the connector (110) of the steerable instrument (100). The instrument guide (266) may, via the supporting arm (252) be attached in fixed (orientation and positional) relation to the $1^{st}$ fitting. The instrument guide (266) may, via the supporting arm (252) be attached in fixed or adjustable (orientation and positional) relation to the proximal-most link (e.g. $L_7$ in FIGS. 16, 17, 22 to 25) of the proximal most joint (e.g. $AR_8$ in FIGS. 16, 17, 22 to 25) of the adapter (250) (which is the same as the distal-most link of the last joint (e.g. $AR_7$ in FIGS. 16, 17, 22 to 25) of the robotic arm). The instrument guide (266) may, via the supporting arm (252) be attached in fixed or adjustable (orientation and positional) the waist plate (272) (FIGS. 31 to 34) of the adapter (250) (which is the same as the distal-most link ($L7_{(RA)}$) of the last joint of the robotic arm). Advantageously, instrument guide (266) allows direct directional control of the instrument shaft (130) meaning the shaft does not need to be pivotable around the fulcrum zone (134) on the shaft (130).

The instrument guide may comprise an instrument guide body provided with an instrument guide slot or recess to receive the steerable instrument or trocar. Preferably, the recess allows loading of the steerable instrument or trocar by laterally (sideways) docking i.e. by displacement of the steerable instrument along a plane parallel or perpendicular to an axis of the steerable instrument. Lateral docking prevents contamination of the instrument tip or end effector that would otherwise arise if it was loaded by axial sliding of the instrument into a slot.

The instrument guide recess may be provided with an instrument guide locking assembly—comprising one or more elements to lock the steerable instrument, such as a threaded bolt, a spring release bolt, or a spring loaded brake—that repeatably and reversibly holds the steerable instrument or trocar in slidable relation to the instrument guide body. When the instrument guide locking assembly is open, the steerable instrument may be laterally docked into the recess. The instrument guide locking assembly is closed, the steerable instrument may be held within the recess allowing axial (A-A') rotations of the shaft and optionally axial (A-A') sliding of the shaft. The instrument guide recess may be provided with a lockable gate—such as a threaded bolt, a spring release bolt, or a spring flap—that repeatably and reversibly blocks the open end of the instrument guide recess. When the gate is open, the steerable instrument or trocar can be laterally docked. When the gate is closed, the steerable instrument or trocar can be held within the instrument guide recess so as to allow axial (A-A') rotations of the shaft and optionally axial (A-A') sliding of the shaft. The steerable instrument held within the recess is rotatable and optionally slidable relative to the instrument guide. The instrument guide and components thereof may be made from any suitable material, preferably suitable for a medical device such as stainless steel, titanium, or composite, or a combination of these. Where necessary one or more of them may be coated with a protective layer, for instance, antibacterial or corrosion resistant.

The steerable instrument may be an engineering tool, industrial tool, or surgical instrument, having use for any type of remote robotically-controlled manipulation, sensing, or activity. The steerable instrument may be a surgical instrument, such as, for instance, a minimally invasive surgical instrument, a laparoscopic instrument, and endoscopic instrument, or an endovascular catheter. The steerable instrument can be used in an articulated instrument such as but not limiting to endovascular, endoscopic, neurosurgical, ENT (ear, nose and throat), orthopaedic applications, surgical instruments, robotic tele-operated medical robotics or hand-held surgical tools and industrial applications.

The steerable instrument may comprise a first and second BPP tandemly arranged and that controls movement of a first and second BDP respectively tandemly arranged, as described for instance in WO 2009/098244 (see FIGS. 13A and 13B therein). In such case, the connector attached to the outer most (first) BPP controls movement of the outer most (first) BDP in the same way as described herein, and is attachable to a robotic arm. The second (inner most) BPP controls movement of the second (inner most) BDP; once the desired position of second (inner most) BDP is met, the position of the second (inner most) BPP is locked using an external clamp. Alternatively, the position of second (inner most) BPP may be controlled using an index mechanism that allows selection from a plurality of fixed discrete positions.

The robotic arm comprises a base end, an effector end and a plurality of intervening linkages connected by joints, wherein the arrangement of links and joints provides at least 6 degrees of freedom of movement to the effector end. The joints are actuatable, typically by motors, hydraulics, or pneumatics allowing control of the position and direction of the effector end by electronic signals. Each joint, also known as a kinematic pair, may offer 1 or 2 degrees of freedom (DOF) of movement, preferably 1 DOF. A joint may be a revolute or prismatic joint. A revolute joint has one degree of freedom of movement that is rotational. A prismatic joint has one degree of freedom of movement that is a linear displacement i.e. slidable. Typically a robotic arm comprises 6 joints each having 1 DOF to generate 6 DOF of movement to the effector end. Where a robot arm contains more than 6 joints, the position and direction of the effector can be attained using a plurality of different combinations of joint positions, offering redundancy that is useful for instance where the path of the robotic arm is restricted. Exemplary arrangement of joints and linkages are illustrated in FIGS. 3A to 3G.

When the last joint is mentioned herein, it refers to the joint that is a kinematic pair of the kinematic chain at the effector end that would attach to the fitting (260), for instance, FIG. 3B, joint 220*g*; FIG. 3C, joint 220*g*; FIG. 3D, joint 220*i*; FIG. 3G, joint 220*i*; FIG. 3H, joint 220*j*; and FIG. 3I, joint 220*i*. The last two joints refer to (1) the last joint and (2) the joint that is a kinematic pair of the kinematic chain attached to the last joint and disposed towards the base end of the robotic arm, for instance FIG. 3B, joints 220*g* and 220*f*; FIG. 3G, joints 220*i* and 220*h*; FIG. 3H, joints 220*j* and 220*i*; and FIG. 3I, joints 220*i* and 220*h*. The last three joints refer to (1) the last joint and (2) the joint that is a kinematic pair of the kinematic chain attached to the last joint and disposed towards the base end of the robotic arm, and (3) the joint that is a kinematic pair of the kinematic chain attached to joint (2) and disposed towards the base end of the robotic arm for instance FIG. 3B, joints 220*g*, 220*f*, 220*e*; FIG. 3G, joints 220*i*, 220*h*, 220*g*; FIG. 3H, joints 220*j*, 220*i*, 220*h*; and FIG. 3I, joints 220*i*, 220*h*, 220*g*. The joints include any integrated into a robotic arm, and any joints added by way of an adapter added to the effector end of the robotic arm.

One or more, preferably each and every joint may be provided with a force sensor, to detect an application of an external force to the joint. Where the joints are revolute joints, a joint torque sensor may be embedded in each joint so as to measure the joint torque. The external force may be applied to a link, or to the effector end. Detection of a force allows the detection of collision of a link against another object such as an adjacent robotic arm or an instrument. Detection of an external force allows the detection of force applied to the steerable tool. Joint torque sensor are already provided in some commercially available robotic arms, such as Kuka robotic arm. In addition to torque sensors in the robotic arm, the fitting in the robot arm may be provided with a force sensor (e.g. a 6-DOF force sensor).

The robotic arm may be commercially provided, for instance, as manufactured by Kuka, Fanuc, ABB or may be an adapted commercially available robotic arm. An adaptation to an existing robotic arm includes, for instance, a replacement of one or more joints or linkage, or an addition of one or more controllably degrees of freedom using an adapter attached to the effector end thereby creating a new effector end.

The effector end is provided with a fitting for dismountable attachment to the connector. The fitting may be a standard fitting such as already provided by the robotic arm, or may customised according to the parameters of the connector.

The last two or three joints and associate linkages of the robot arm may disposed such that their axes of rotation intersect for example as illustrated in FIGS. 10 to 25, 41, 42. The last two or three joints may be configured such that their axes of rotation intersect with the zone of motion of the BPP, preferably with the BPP-CZOM as described earlier. The arrangement of joints may be realised by setting the joint angles of the robot arm (e.g. FIG. 10, 19), or by using an adapter attached to the robot arm effector end (e.g. FIGS. 11 to 18, 20 to 25, 41, 42) that provides one or more additional rotational degrees of freedom. The last two or three joints are maintained in the aforementioned relation during control of the steerable instrument.

A moveable member may be provided, wherein the base end (230) of the robot arm (200) is attached to the moveable member, and wherein the position of the moveable member is adjustable (displaceable in 1 or more directions), and optionally the angle of the moveable member is adjustable (rotatable in 1 or more directions).

The moveable member is comprised in a (motorised) gantry, a (motorised) trolley, or a further robotic arm.

As mentioned elsewhere herein, the last two or three or more joints and associated linkages of the robot arm may added by way of an adapter (250, 250*a*, 250*b*), as illustrated, for instance, in FIGS. 11 to 18, 20 to 42. Each joint of the adaptor is driven e.g. by a servo motor or linear actuator. The adaptor is configured for attachment to an effector end of an existing robotic arm and creates a new effector end for attachment to the steerable instrument (100). The adapter (250) may be configured for dismountable attachment to an effector end of the robotic arm. Advantageously, an adapter increases the number of degrees of freedom of an existing robotic arm. Additional degrees of freedom improve the side-by-side working of multiple robotic arms each attached to a steerable instrument entering through the same point of entry e.g. into a bodily incision. Where different instrument poses would cause linkages of the robotic arms to collide, the additional degrees of freedom allow the robotic arms to maintain the same respective instrument poses but to alter the position and/or direction of at least the linkages that would collide of the respective robotic arms. Thus, a certain instrument pose can be achieved in a number of different robotic arm poses, the redundancy allowing selection of the robotic arm poses that minimises clashing in a confined working space.

A further advantage of an adapter is to upgrade a functionality of an existing robotic arm such as a surgical robotic arm that does not have the requisite number of degrees of freedom (e.g. 6DOF) to control a steerable instrument as described herein. Addition of two extra degrees of freedom by way of the adapter may bring an existing 3 or 4 DOF robot that already has service in a surgical theatre into compliance with the present steerable instrument.

Adapter Basics

The present application further provides an adapter. The adapter preferably comprises two joints (also known as a kinematic pair), optionally more or less joints (e.g. 1 joint or 3 joints or more joints) each offering 1DOF one degree of freedom of movement that is rotational or a linear displacement. Each joint is flanked and connected by intervening linkages. The joints may be rotational (revolute) joints, prismatic (sliding) joint, or a mixture of rotational and prismatic joints. The joints may be connected in series and/or in parallel. The adapter (250) may have a proximal

(20) and distal (40) end. The adapter (250) may be provided at the proximal end with a $1^{st}$ fitting adapted for dismountable attachment in fixed revolute relation to the end effector of the robotic arm. The adapter (250) may be provided with at the distal end with a $2^{nd}$ fitting (which is equivalent to the robotic arm fitting) adapted for dismountable attachment in fixed revolute relation to the connector (110) of the steerable instrument (100).

Adapter Serial Revolute Joints

The adapter joints may be rotational joints connected in series. The proximal link (e.g. $L_7$ in FIGS. 11 to 18, 20 to 25, 30, 31) of the proximal-most joint (e.g. rotating around $AR_8$ in FIGS. 11 to 18, 20 to 25) of the adapter is attachable in fixed revolute relation to the end effector (e.g. distal link of the last joint with axis of rotation $AR_7$ in FIGS. 11 to 18, 19 to 25, 30, 31) of the robotic arm. The distal link of the distal-most joint of the adapter is attachable in fixed revolute relation to the connector steerable instrument, via complementary ($1^{st}$) fitting. (e.g. the proximal link (e.g. $L_7$ in FIGS. 11 to 25) of the proximal-most joint (e.g. $R_8$ in FIGS. 11 to 18, 19 to 25), or an extension thereof) adapted for dismountable attachment in fixed revolute relation to the end effector of the robotic arm. The adapter (250) may be provided with at the distal end with a $2^{nd}$ fitting (e.g. distal link of the last joint with axis of rotation $R_9$ or $AR_9$ in FIGS. 11, 12, 14 to 18, 19 to 25, or extension thereof; distal link of the last joint with axis of rotation $AR_8$ in FIG. 13, or extension thereof) adapted for dismountable attachment in fixed revolute relation to the connector (110) of the steerable instrument (100).

Adapter Parallel Revolute Joints

The adapter joints may include rotational joints connected in parallel (FIGS. 37 to 40).

Adapter Multipod

Figure 27:
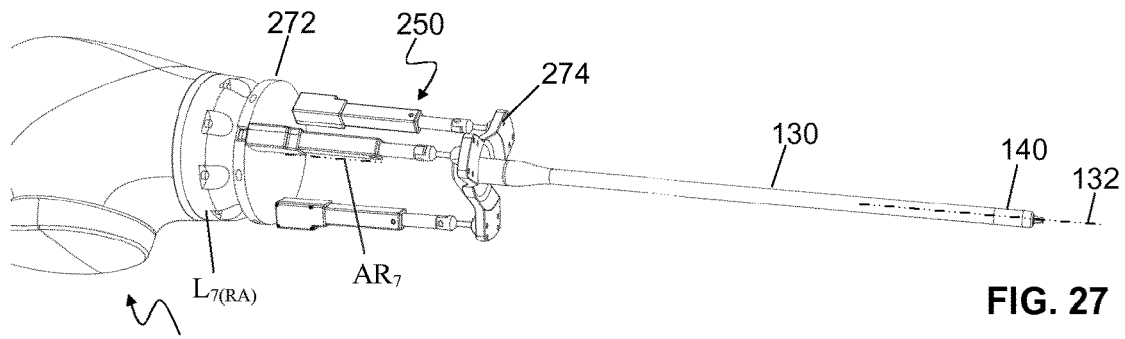
FIGS. 27 to 30 show different actuation positions of the adaptor (250) shown in FIG. 26.
Figure 28:
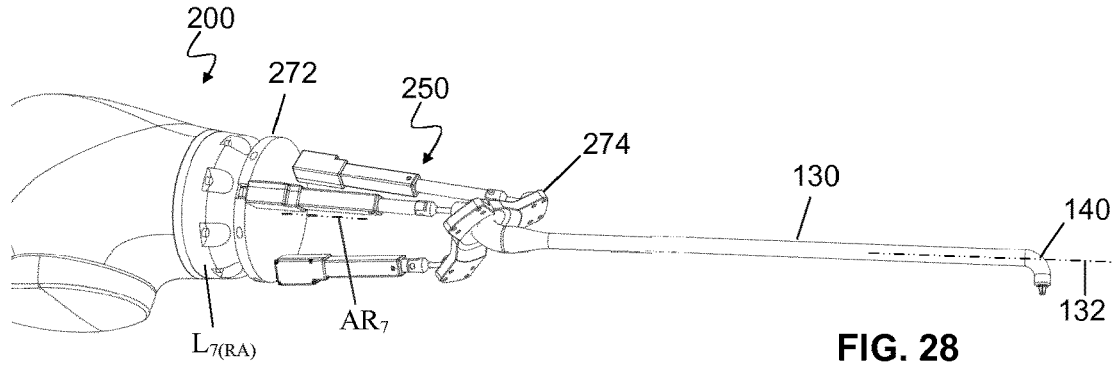

The adapter joints may include prismatic joints connected in parallel as shown for example in FIGS. 26 to 36. The adapter (250) may comprise at least three prismatic joints arranged in parallel, so forming a multipod mechanism. Such adaptor may be known herein as a multipod adapter. The multipod adapter containing three prismatic joints may be referred to as a tripod adapter; where it contains four prismatic joints it may be referred to as a tetrapod adapter. At a proximal end of the multipod adaptor is a waist plate (272) that is attachable to the robot arm, in particular attachable in fixed revolute relation to the end effector, in particular to the last link ($L_{7(RA)}$) of the robotic arm, via a complementary ($1^{st}$) fitting. At a distal end of the multipod adaptor is a footplate (274)) that moves responsive to movements of the prismatic joints. The footplate (274) is attachable in fixed relation to the connector of the steerable instrument, via a complementary ($2^{nd}$) fitting. Actuation of one or more of the prismatic joints ($L_{9a}$, $L_{9b}$, $L_{9c}$) allows the footplate (274) to tilt relative to the base plate (272)—compare for instance FIGS. 27 and 28 showing the footplate (274) in a neutral position (FIG. 27) and the bendable distal part (140) straight relative to the shaft (130), or showing the footplate (274) in a tilted position (FIG. 28) and the bendable distal part (140) bent relative to the shaft (130). The footplate (274) effectively has 2 degrees of freedom.

Each proximal link ($L_{8a}$, $L_{8b}$, $L_{8c}$) of each prismatic joint ($P_{8a}$, $P_{8b}$, $P_{8c}$) may be attached to the waist plate (272) (FIG. 26). Each proximal link ($L_{8a}$, $L_{8b}$, $L_{8c}$) of the each prismatic joint ($P_{8a}$, $P_{8b}$, $P_{8c}$) may be attached to the waist plate (272) via a joint having 1 or 2 DOF, preferably with a revolute (1DOF) joint. The proximal links ($L_{8a}$, $L_{8b}$, $L_{8c}$) may be distributed evenly around a circumference of a circle. The circle may be centred on a central axis of the $1^{st}$ fitting.

Each distal link ($L_{9a}$, $L_{9b}$, $L_{9c}$) of each prismatic joint ($P_{8a}$, $P_{8b}$, $P_{8c}$) may be attached to the footplate (274) (FIG. 26). Each distal link ($L_{9a}$, $L_{9b}$, $L_{9c}$) of the each prismatic joint ($P_{8a}$, $P_{8b}$, $P_{8c}$) may be attached to the footplate (274) via one or more joints having 1 or 2 DOF, preferably with a revolute (1DOF) joint. The distal links ($L_{9a}$, $L_{9b}$, $L_{9c}$) may be distributed evenly around a circumference of a circle. The circle may be centred on a central axis of the $2^{nd}$ fitting.

The additional degrees of freedom improve the side-by-side working of multiple robotic arms each attached to a steerable instrument entering through the same point of entry e.g. into a bodily incision; in FIG. 35 two robotic arm (200, 200') are shown in close proximity each provided with an adapter (250, 250'); the distal bendable part (140, 140') can be flexed (FIG. 36) by changing the orientation of the adapter footplate (274, 274') avoiding clashing movement of the last link of the robotic arm ($L7_{(RA)}$).

The adapter (250) may be provided with the instrument guide (266) guide as described elsewhere herein.

The adapter may be configured such that the axes of rotation of the two joints intersect (e.g. $AR_8$ and $AR_9$ in FIGS. 11, 12, 14 to 18, 20 to 25, 41, 42; AR, and $AR_8$ in FIG. 13). The adapter may be configured such that the axes of rotation of the two joints of the adapter (e.g. $AR_8$ and $AR_9$ in FIGS. 11, 12, 14 to 18, 19 to 25, 41, 42) and of proximal-most link ($L_7$) of the proximal most joint (e.g. AR, in FIGS. 11, 12, 14 to 25, 41, 42) of the adapter (which is the same as the axis of rotation of the distal-most link of the last joint (e.g. $L_{7(RA)}$ in FIGS. 11, 12, 18, 22 to 25) of the robotic arm) intersect. They intersect in the BPP (120) of the steerable instrument (100), in particular at the zone of motion (122), more precisely at the BPP-CZOM.

The adapter may be configured such that the axis of rotation of the distal-most joint of the adapter (e.g. $R_9$ in FIGS. 11 to 13) is disposed parallel to a central axis of the proximal tip of the BPP (120), or disposed parallel to a central axis of the proximal tip of the connector (110). The parallel relationship is maintained in bent and straight instrument configuration. The angle is fixed in bent and straight instrument configurations.

Figure 20:
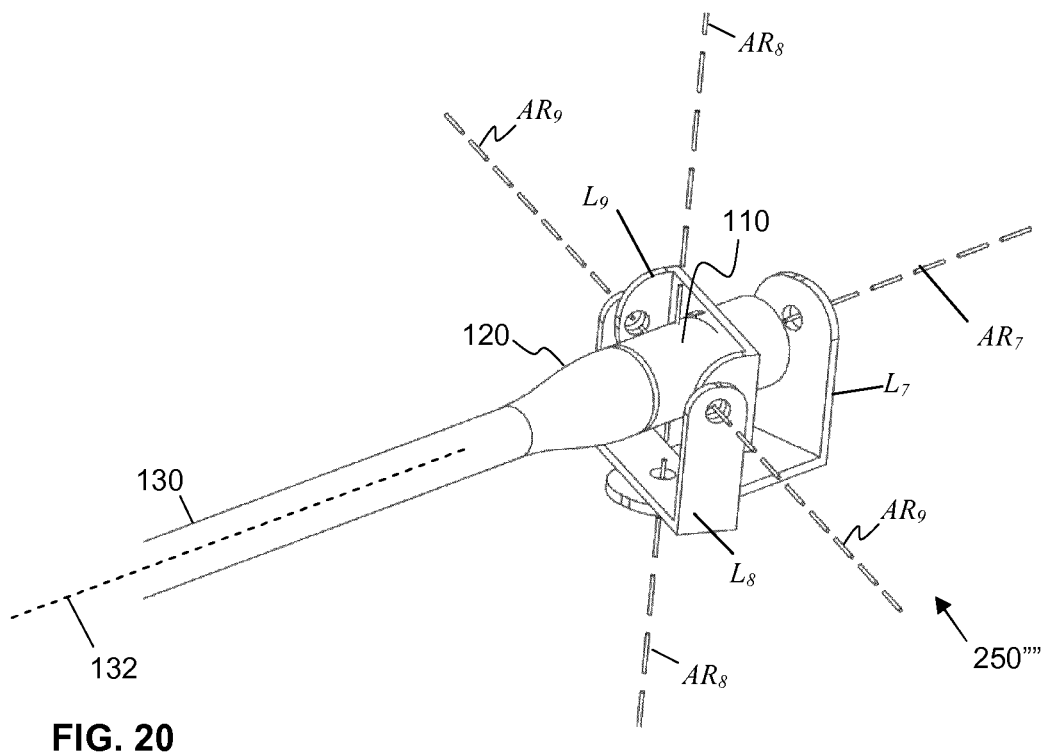
FIGS. 20 and 21 are similar to FIGS. 14 and 15, except the axis of rotation of the distal-most joint of the adapter (e.g. $AR_9$) is disposed non-perpendicular to a central axis (112) of the connector (110).

The adapter may be configured such that the axis of rotation of the distal-most joint of the adapter (e.g. $AR_9$ in FIGS. 14 to 18, 20 to 25, 41, 42) is disposed non-parallel to a central axis of the proximal tip of the BPP (120), or disposed non-parallel to a central axis (112) of the connector (110). The non-parallel relationship is maintained in bent and straight instrument configuration. The angle is fixed in bent and straight instrument configurations. There may be a difference of 10 to 170 deg, preferably 55 to 125 deg, or 70 to 110 deg. Exemplarily, in FIGS. 14 to 18, 21, 22, 23, 24 and 25 $AR_9$ is fixed at 90 deg with respect to the central axis of the proximal tip of the BPP (120), or fixed at 90 deg to a central axis (112) of the connector (110). In FIG. 20 $AR_9$ is fixed at 65 deg with respect to the central axis of the proximal tip of the BPP (120), or fixed at 65 deg to a central axis (112) of the connector (110).

Preferably, the adapter is configured such that the axis of rotation of the distal-most joint of the adapter (e.g. $AR_9$ in FIGS. 14 to 18, 22 to 23, 41, 42) is disposed parallel to a plane (e.g. Pc in FIGS. 14 to 17) perpendicular to a central axis of the proximal tip of the BPP (120) or to a plane perpendicular to the central axis (112) of the connector (110). Preferably, the adapter is configured such that the axis of rotation of the distal-most joint of the adapter (e.g. $AR_9$ in FIGS. 14 to 18, 22 to 23, 41, 42) is disposed perpendicular to a central axis of the proximal tip of the BPP (120) or to the central axis (112) of the connector (110). The aforementioned plane-parallel or perpendicular relationships are maintained in bent and straight instrument configuration. The angle is fixed in bent and straight instrument configurations. Exemplarily, in FIGS. 14 to 19, $AR_9$ is fixed at 0 deg with respect to such a plane.

The adapter may be configured such that a plane formed by the axes of rotation (e.g. $AR_8$ and $AR_9$ in FIGS. 14 to 18, 20 to 25, 41, 42) of the two distal-most joints of the adapter is disposed at an angle different from 0° (preferably is disposed at 90°) to a central axis of the proximal tip of the BPP (120) or to a central axis (112) of the connector (110). The angular relationship is maintained in bent and straight instrument configuration. The angle is fixed in bent and straight instrument configurations. Exemplarily, in FIGS. 14 to 18, 21, 22, 23, 24, 25, 41, 42 the angle is fixed at 90 deg. In FIG. 20 the angle is fixed at 65 deg.

The adapter may be configured such:
the last three axes intersect (e.g. $AR_7$, $AR_8$ and $AR_9$ in FIGS. 14 to 18, 20 to 25, 41, 42) at BPP (120) of the steerable instrument (100), in particular at the zone of motion (122), more precisely at the BPP-CZOM, and
the axis of rotation the distal-most joint of the adapter (e.g. $AR_9$ in FIGS. 14 to 18, 20 to 25, 41, 42) is disposed non-parallel to a central axis of the proximal tip of the BPP (120), or disposed non-parallel to a central axis (112) of the connector (110).

The angle is fixed in bent and straight instrument configurations. Exemplarily, in FIGS. 14 to 18, 21, 22, 23, 24, 25, 41, 42, the axes are fixed non-parallel (at 90 deg). In FIG. 20 the axes are fixed non-parallel (at 65 deg).

The adapter may be configured such:
the last three axes intersect (e.g. $AR_7$, $AR_8$ and $AR_9$ in FIGS. 14 to 18, 20 to 25, 41, 42) at BPP (120) of the steerable instrument (100), in particular at the zone of motion (122), more precisely at the BPP-CZOM, and
a plane formed by the axes of rotation (e.g. $AR_8$ and $AR_9$ in FIGS. 14 to 18, 20 to 25, 41, 42) of the two distal-most joints of the adapter is disposed at an angle different from 0° (preferably is disposed at 90°) to a central axis of the proximal tip of the BPP (120) or to a central axis (112) of the connector (110).

The angle is fixed in bent and straight instrument configurations. Exemplarily, in FIGS. 14 to 18, 21, 22, 23, 24, 25, 41, 42, the angle is fixed at 90 deg. In FIG. 20 the angle is fixed at 65 deg.

In the above configurations, the direction of the shaft (130) central axis (132) is fixed relative to the direction of the axis of rotation of the of the last distal joint (e.g. $AR_7$ in FIGS. 14 to 18, 20 to 25, 41, 42) of the robotic arm, when the instrument is in bent or straight configuration. The axis of rotation of the last joint (e.g. $AR_7$ in FIGS. 14 to 18, 22, 23) of the robotic arm may be co-axial with the shaft central axis (132). The axis of rotation of the last joint (e.g. $AR_7$ in FIGS. 20, 21, 24, 25) of the robotic arm may be inclined with the shaft central axis (132). This allows the proximal-most link (e.g. $L_7$ in FIGS. 14 to 14 to 18, 20 to 25, 41, 42) of the proximal most joint (e.g. $AR_8$ in FIGS. 14 to 14 to 18, 20 to 25, 41, 42) of the adapter (which is the same as the distal-most link of the last joint (e.g. $AR_{7(RA)}$ in FIGS. 18, 22 to 24) of the robotic arm) to be disposed or attached in fixed positional and rotational relation to the instrument shaft (130). It allows direct directional control of the instrument shaft (130) meaning the shaft does not need to be pivotable around the fulcrum zone (134) on the shaft (130).

The fixed positional and rotational relation to the instrument shaft (130) with the axis of rotation of the last joint (e.g. $AR_7$) of the robotic arm may be achieved by control of the robotic arm (200) and adapter (250) with knowledge of the length of the steerable instrument (100) and position of the freely-swivelling trocar in the subject. This is shown in FIGS. 11, 12, 14, 15, 18, 20, 21, 27-30, 41, 42 not having a supporting arm (252).

The fixed positional and rotational relation to the instrument shaft (130) with the proximal-most link (e.g. L7 in FIGS. 16, 17, 22 to 25) of the proximal most joint (e.g. $AR_8$ in FIGS. 16, 17, 22 to 25) of the adapter may be achieved using the instrument guide (266) described elsewhere herein. Accordingly, the proximal-most link ($L_7$) of the proximal most joint (e.g. $AR_8$ in FIGS. 16, 17, 22 to 25) of the adapter (250) may be provided with a distally extending arm or supporting arm (252) and instrument guide (266) (also known as coupling herein) for the instrument shaft (130) in order to retain the instrument shaft (130) in fixed positional and rotational relation with the proximal-most link ($L_7$) of the proximal most joint (e.g. $AR_8$ in FIGS. 16, 17, 22 to 25) of the adaptor (which is the same as the distal-most link of the last joint (e.g. FIGS. 14 to 18 and $L_{7(RA)}$ FIGS. 18, 20 to 24) of the robotic arm).

The distally extending arm (252) and instrument guide (266) are preferably rigid. The instrument guide instrument guide is configured to receive the shaft of the steerable instrument or a trocar.

The supporting arm (252) may be adjustable; for instance, to adjust orientation of the instrument guide (266) and/or instrument guide body with respect to the anchoring robotic arm linkage. The adjustable supporting arm (252) may be repeatably lockable to a rigid state. The adjustable supporting arm (252) may be configured to adjust an orientation of the instrument guide (266) and/or instrument guide body with respect to the proximal-most link ($L_7$) of the proximal most joint (e.g. $AR_8$ in FIGS. 16 and 17) of the adaptor. Once the orientation has been set, the adjustable supporting arm is configured to lock the orientation. The orientation may be repeatably lockable. The adjustable supporting arm (252) may comprise two or more rigid linkages (252-a, 252-b FIGS. 22 to 25) mutually connected by lockable joint (253), that offers 1 or 2 degrees of freedom (DOF) of movement.

The instrument guide (266) may be attached via the supporting arm (252) in fixed relation to the proximal-most link ($L_7$) of the proximal most joint (e.g. $AR_8$ in FIGS. 16, 17, 22 to 25) of the adapter (250).

As mentioned elsewhere herein, multiple robotic arms may be provided. The may each be disposed with a steerable instrument that is inserted through the same opening in a working space. According to one aspect, the pose of the robotic arms may be such that each arm avoids collision. This require that the controller compares the pose and pose trajectory of each arm so that their respective movements can proceed without collision. The pose of one robotic arm may change while keep the pose of the instrument constant in order to accommodate a movement by the other robotic arm. This is particularly applicable when the robotic arms have more than 6 DOFs. It could be anticipated that a first robotic arm would have to move a redundant joint to give space to the second arm. Such a system of multiple robotic arms may be configured to work and move in a harmonized way. FIGS. 35 and 36 show example of two side-by-side robotic arms that with the presence of an adapter avoid clashing.

Provided herein is a method of controlling movements of the steerable instrument using the robotic arm. The inventors have found that by virtue of a single connector, the direction of the shaft can be controlled, and separately the bending direction of the BDP. Further, axial (A-A') displacement of the shaft is controllable. Moreover, the distal tip is controllably rotatable while the BDP is in a bent position using the same single connector; rotation of the distal tip can be achieved while maintaining a constant direction of the shaft. Existing robotically controlled instruments, for instance, laparoscopic instrument supplied for use with the da Vinci surgical systems are supplied with 4 separate rotary dials that interface with a complementary fitting on a robotic arm (see FIGS. 1A to 1E). A system of wires and pulleys within the disposable laparoscopic instrument transfers forces from the dials towards the end effector (gripper). The complexity of the mechanism is self-evident from prior art FIGS. 1D and 1E; the proximal-end housing and effector end contain a large number of components held under tension by the wires to transmit rotational forces through a rotatable shaft and across revolute joints to the distal wrist and end effector which also contains a complex arrangement. A known disadvantage is the high cost of the instrument because of the multitude of components that have high tolerances and reliability and are able to withstand forces during use, as well as the assembly time.

For some procedures, a continuous rotation of the shaft or of the end effector is desirable, for instance, if the instrument is used for a remote drilling, abrasive action, tightening a thread, winding a cord, and the like. The pulley and wire system has a limit on the number of revolution of the shaft currently to 1.5 rotations.

The position and orientation of the robotic arm effector end fitting determines the full pose of the instrument, also known as "instrument full pose" or "instrument pose" herein. The instrument full pose refers to the direction of the shaft around the fulcrum zone, the bending direction of the BDP that is distinct from the direction of the shaft, and the revolute angle of the distal end. The instrument full pose effectively determines the position and direction of the instrument distal end and the revolute angle of the instrument distal end e.g. of an end effector.

With the presently described steerable tool and system, a single connector is used to define the instrument full pose, and the distal tip is infinitely rotatable under robotic control.

The position and orientation of the robotic arm effector end fitting required to achieve a certain full pose of the instrument may be determined using a (mathematical) model of the steerable instrument and one or more (preferably all) parameters relating to: bendable proximal part length, bendable proximal part maximum diameter, bending curvature of the bendable proximal part, position of the BPP-ZOM, position of the BPP-CZOM, distance of BPP to connector, shaft length, shaft diameter, position of the fulcrum zone, bending movement amplification factor, dimension of the fulcrum zone, bendable distal part length, bendable distal part maximum diameter, bending curvature of the bendable distal part, position of the BDP-ZOM, position of the BDP-CZOM distance of BDP to distal tip. For a simplified model, the following parameters of the steerable instrument may be used: shaft length, distance of BPP to connector, distance of BDP to distal tip, position of the fulcrum zone, diameters of the BPP and BDP or the amplification factor; the following optional parameters may be added: the BPP length, the BDP length, the bending curvature of the BPP, and the bending curvature of the BDP.

A relation between the instrument pose and pose of the robotic arm may be determined from one or more mathematical models. An example is provided as follows:

For a Simplified Model:

$$\vec{P}_e = \vec{f}^*(\vec{P}_{R,b}, \vec{\Psi}_R, l_{BPP}, A_{B,s}, l_S, \vec{P}_{FC}, l_{BDP})$$

$$\vec{R}_e = \vec{g}^*(\vec{P}_{R,b}, \vec{\Psi}_R, l_{BPP}, A_{B,s}, l_S, \vec{P}_{FC}, l_{BDP})$$

For a Detailed Model:

$$\vec{P}_{BDP,ZOM} = \vec{g}(\vec{\Psi}_E) =$$

$$\vec{P}_e = \vec{f}(\vec{P}_{R,b}, \vec{\Psi}_R, l_{BPP}, d_{BPP,Max}, \vec{P}_{BPP,ZOM}, l_{BPP}, l_S, \vec{P}_{FC}, A_B, l_{BDP}, d_{BDP,Max}, \vec{P}_{BDP,ZOM})$$

$$\vec{R}_e = (\vec{P}_{R,b}, \vec{\Psi}_R, l_{BPP}, d_{BPP,Max}, \vec{P}_{BPP,ZOM}, l_{BPP}, l_S, \vec{P}_{FC}, A_B, l_{BDP}, d_{BDP,Max}, \vec{P}_{BDP,ZOM})$$

Definitions

| | |
|---|---|
| $\vec{P}_e = (x, y, z)$ | position of end effector |
| $\vec{R}_e = (\Theta_x, \Theta_y, \Theta_z)$ | orientation of end effector |
| $l_{BPP}$ | bendable proximal part length |
| $d_{BPP,Max}$ | bendable proximal part maximum diameter |
| $\vec{P}_{BPP,ZOM} = (x, y, z)$ | position of the BPP-ZOM relative to shaft |
| $\vec{P}_{BP,CZOM} = (x, y, z)$ | position of the BPP-CZOM relative to shaft |
| $l_{Bpp}$ | distance of BPP to connector |
| $l_S$ | shaft length |
| $l_{BDP}$ | shaft diameter |
| $\vec{P}_{FC} = (x, y, z)$ | position of the fulcrum zone |
| $A_B$ | bending movement amplification factor |
| $l_{FC}$ | dimension of the fulcrum zone |
| $l_{BDP}$ | bendable distal part length |
| $d_{BDP,Max}$ | bendable distal part maximum diameter |
| $r_{BDP}$ | bending curvature of the bendable distal part |
| $\vec{P}_{BDP,ZOM} = (x, y, z)$ | position of the BDP-ZOM |
| $\vec{P}_{BDP,CZOM} = (x, y, z)$ | position of the BDP-CZOM |
| $l_{BDP,e}$ | distance of BDP to distal tip |
| $\Theta_{ri}$ | position of robot's i'th revolute joint |
| $d_{rj} = (x,y,z)$ | position of robot's j'th prismatic joint |
| $\vec{P}_{R,b} = (x, y, z)$ | position of robot base |
| $\Psi_R = \Theta_{r1}, \Theta_{r2}, \ldots, \Theta_{rn}, d_{r1}, d_{r2}, \ldots, d_{rm})$ | robot joints position |
| $\Psi_S = (\Theta_{s1}, \Theta_{s2}, \Theta_{s3})$ | pose of Shaft of Steerable Instrument |
| $\Psi_E = (\Theta_{e1}, \Theta_{e2}, \Theta_{e3})$ | pose of end effector of Steerable Instrument |
| $d_{BPP,s}$ | bendable proximal part simplified single diameter |
| $d_{BDP,s}$ | bendable distal part simplified single diameter |
| $A_{B,s} = \dfrac{d_{BPP,s}}{d_{BDP,s}}$ | simplified bending movement amplification factor |

Control of the robotic arm effector end fitting can be derived following the Denavit-Hartenberg convention. In this convention, coordinate frames are attached to the robotic arm joints between two links such that one transformation is associated with the joint, [Z], and the second is associated with the link [X]. The coordinate transformations along a robotic arm consisting of n links form the kinematics equations of the robot, $$[T]=[Z_1][X_1][Z_2][X_2] \ldots [X_{n-1}][Z_n]$$

where [T] is the transformation locating the end-link.

In order to determine the coordinate transformations [Z] and [X], the joints connecting the links are modelled as either revolute or prismatic joints, each of which have a unique line S in space that forms the joint axis and define the relative movement of the two links. A typical robotic arm, is characterised by a sequence of six lines Si, one for each joint in the robotic arm. For each sequence of lines Si and Si+1, there is a common normal line Ai,i+1. The system of six joint axes Si and five common normal lines Ai,i+1 form the kinematic skeleton of the typical six degree of freedom robotic. Denavit and Hartenberg introduced the convention that Z coordinate axes are assigned to the joint axes Si and X coordinate axes are assigned to the common normals Ai, i+1.

A control unit may be provided configured to output (electronic, light, RF) control signals to the robotic arm. The control unit typically comprises a circuit (e.g. processor and memory) configured to run a set of executable instructions. The output may be electronic signals, light signals, wireless signals, and the like.

The control signals may effect movements of steerable instrument that include
  rotation of the shaft around the fulcrum zone),
  rotation of the shaft axially (A-A'),
  displacement of the shaft axially (A-A'),
  bending of the bendable distal part,
  rotation of the end effector when the bendable distal part is in a bent position.

The axial position of the shaft may change during a procedure. The control unit may be configured to determine the position of the fulcrum zone in response to a change in an axial position of the shaft, i.e. position of fulcrum zone along the shaft may be dynamically adjustable.

The above-mentioned movements of the steerable instrument shaft and bendable distal part combined to determine the position and orientation of the steerable instrument end effector.

A manual input unit may be provided to receive manual input (e.g. movement information) for control of the steerable instrument.

The control unit may be further configured to:
  receive a sensor signal from the manual input unit,
  output a control signal for the robotic arm to control movement thereof responsive to the signal from the manual input unit.

The manual input unit may sense movements of one hand, allow corresponding control of one robotic arm. The manual input unit may sense movements of both hands, allow corresponding control of two robotic arms. The manual input unit may sense movements of each hand in more than 2 DOF (e.g. 3, 4, 5, 6, 7 DOF), preferably 6 or more DOF. Most preferred is that movement is sensed in 3 DOF of rotation, 3 DOF of translation, and 1 DOF is sensed for actuation of the end effector. Any additional redundant DOFs could reduce singularity of the robotic arm. The manual input unit provide a force feedback on 0 DOF, or on 3 position DOF or on all 6 DOF.

The manual input unit may be any that outputs a signal corresponding to a manually actuated mechanical movement. The manual input unit may comprise one or more of the following:
  A mechanical joystick. The mechanical joystick may have more than 2 DOF (e.g. 3, 4, 5, 6, 7 DOF, preferably 6 or more DOF. Most preferred is that it has 3DOF rotation, 3DOF position, and 1 for actuation of the end effector. There may be a force feedback on 0 DOF, or on 3 position DOF or on all 6 DOF. The joy stick may align itself with the position and orientation of the end effector.
  A wireless vElectromagnetical 6DOF sensor (Ascension)
  A wireless 6DOF comprising one or more gyroscopes and/or one or more accelerometers. Preferably it comprises a 3 rotation axis accelerometer, and a 3 linear axis accelerometer. Examples include games controllers (e.g. Nintendo WII, Sony playstation MOVE etc), smartphones.
  Image recognition system. In such system: 2 camera's capture movements of the surgeon's hands, potentially disposed with a reference object or marking for the camera to optically lock onto.
  One or more foot pedals. One or more foot pedals be configured to toggle control of one or more additional robotic arms. For instance, a first foot peddle may toggle control by manual input device unit sensing movement of the right hand between the right-hand instrument installed on a second robotic arm and the third instrument installed on a third robotic arm. The third robotic arm may be used to retract tissue. For instance, a second foot peddle may toggle control by manual input device unit sensing movement of the right hand between the right-hand instrument installed on a second robotic arm and a fourth instrument installed on a fourth robotic arm. The fourth robotic arm may be used to hold e.g. endoscope in a fixed position.

The manual input unit may comprise a "finger clutch". Activation of the finger clutch allows repositioning of the input device without influence on the end effector. It allows the repositioning position the operator's hand within a centre of a volume of movement when the instrument movement has reached an edge of the volume of movement. The finger clutch may be disposed as a switch in the proximity of the hands, or as a foot pedal.

The control unit may be further configured to transform manual movement sensed by the manual input unit to a corresponding movement of the steerable instrument. The corresponding movement of the instrument may be scaled (up or down) compared with the manual movement of the user. The corresponding movement of the instrument may be dampened compared with the manual movement of the user.

In a particular aspect, rotational motions detected by the manual input unit are scaled up in the corresponding movement of the steerable instrument. In a particular aspect, rotational motions detected by the manual input unit are scaled up. In a particular aspect, only rotational motions detected by the manual input unit are scaled up, displacement motions are not scaled up in the corresponding movement of the steerable instrument. In a particular aspect, only rotational motions detected by the manual input unit corresponding to a bending of the bending movements of the distal tip or end effector are scaled up, displacement motions are not scaled up in the corresponding movement of the steerable instrument. In a particular aspect, bending movements of the distal tip or end effector are scaled up compared with the manual input. For instance, if manual input unit detects a 60 deg bending of the distal tip or end effector, the corresponding angular motion of the distal tip or end effector may be scaled up to 90 deg. If manual input unit detects a 30 deg bending of the distal tip or end effector, the corresponding bending of the distal tip or end effector may be scaled up to 45 deg. If manual input unit detects a 0 deg bending of the distal tip or end effector, the corresponding bending of the distal tip or end effector remains at 0 deg. Because of the upscaling of the bending of the distal tip or end effector, there is less strain to the surgeon's wrist. The control unit may be further configured to transforms sensor signals received from the manual input unit into control signals for the robotic arm using a (mathematical) model of the steerable instrument as described earlier.

The model may treat the bendable distal part as a joint with a single point through which two or more axes of rotation intersect (the BDP-CZOM mentioned earlier). The model may treat the bendable proximal part as a joint with a single point through which two or more axes of rotation intersect (the BPP-CZOM mentioned earlier).

The control unit may be further configured to maintain the instrument shaft in fixed slidable relation with a trocar inserted into an expandable bodily cavity responsive to changes in a position of a trocar (that moves in concert with changes in position of a wall of the bodily cavity) (implemented by, e.g., 2D or 3D camera+pattern recognition or reflective markers). The controller unit may be configured to filter out motion of an artefact of respiration.

The control unit may be further configured to maintain the axial position of the fulcrum zone in fixed relation with the trocar.

A contactless measurement unit may be provided to receive contactless data (e.g. dimensional measurement data, visual information, spectroscopic information, distance information of features within the operating volume) for control of the steerable instrument. The contactless measurement unit facilitates automatic procedures using information obtained from the contactless measurement unit. The contactless measurement unit may comprise an image sensor. The contactless measurement unit may comprise a camera, e.g. 2D or 3D camera. The contactless measurement unit may comprise a spectroscopy instrument. The contactless measurement unit may comprise a distance sensor, e.g. IR sensor. The contactless measurement unit is insertable into the operating volume. It is envisaged for use in a surgical environment where the operating volume is a surgical space within the subject, and the contactless measurement unit detects features within the operating volume such as tissue structures, tissue types and the like; it may be provided at the end of a laparoscopic instrument such as an endoscope The control unit may automatically control the robotic arm to perform the desired operation, using signals received from the contactless measurement unit.

The control unit may be configured to control the robotic arm such that the steerable instrument performs repetitive motions. The robotic arm may learn one action, and be able to repeat it under guidance of the contactless measurement unit. For instance, making 10 sutures in a row or cutting in a straight line, circle or certain pattern The control unit may be further configured to determine from force sensors disposed in one or more (preferably all of the) joints of the robotic arm a force event, where force sensors detect an external forced applied to the steerable instrument. The external force may be a linear force, preferably a force applied along an axial (A-A') direction of the shaft. The external force event may be above a certain force threshold value. The threshold value may depend on the end effector used. When the end effector is a scissor tool the threshold value would be lower than when introducing a blunt fenestrated clamp. The threshold value may depend on the structure being worked on. The threshold value may be user-defined for instance by selection from a pull-down menu or the like; the user (e.g. surgeon) may select the threshold according to the surgery type. A neurosurgeon would use a threshold different from that of an orthopaedic surgeon.

The force event may be triggered when a steerable instrument is not within a field of view (FOV) of the operator of the steerable instrument. It is applicable in a surgical setting where the surgeon has a good view of a small volume of an operating space through an endoscope e.g. of a small vessel during prostatectomy, but the view behind the endoscope is not visible; he has no view on the space between the trocar and the target anatomy. There is a risk that an instrument can cause damage to structures out of view, particularly during insertion of an instrument into the operating space, or where manoeuvres are performed by an assistant. An inserted instruments might cause damage to bowels, arteries or other anatomical structures. Sometimes without knowledge of by the surgeon as the surgeon does not "feel" when the motor driven instrument perforates a tissue.

By triggering a force event above a certain force threshold and when the steerable instrument is outside of the FOV of the operator, it still allows the steerable instrument to apply force to structures when the tip of end effector is in the FOV of the operator. The detection of a force event may results in a stopping or reversal of robotic arm movement of the steerable instrument, and/or an audible or visual alarm. The FOV of the operator may be at a radius of 4-5 cm from the target operational e.g. from a target anatomy.

Further provided herein is a system comprising the steerable instrument as described herein, and the robotic arm. The system may further comprise the control unit as described herein. The system may further comprise the manual input unit as described herein. The system may further comprise the contactless measurement unit as described herein. The system may comprising one or more additional robotic arms.

Further provided herein is a method of controlling a robotic arm as described herein to move an attached steerable instrument as described herein, which method effects movements of steerable instrument that include:

rotation of the shaft around the fulcrum zone,
rotation of the shaft axially (A-A'),
displacement of the shaft axially,
bending of the bendable distal part, and
rotation of the end effector when the bendable distal part is in a bent position.

According to the method movements of steerable instrument may be responsive to a manual input unit.

Movements of the steerable instrument responsive to a manual input unit may be determined using a (mathematical) model of the steerable instrument described earlier Further provided is a computing device or system configured for performing the method described herein.

Further provided is a computer program or computer program product having instructions which when executed by a computing device or system cause the computing device or system to perform the method described herein.

Further provided is a computer readable medium having stored thereon a computer program as described herein.

Further provided is a computer readable medium having stored thereon instructions which when executed by a computing device or system cause the computing device or system to perform the method as described herein.

Further provided is a data stream which is representative of a computer program or computer program product as described herein.

FIGS. 1A to E show different views of a robotic steerable instrument (800) of the prior art that is for use with a da Vinci surgical robotic system (Intuitive Surgical Inc.). The prior art instrument (800) comprises a shaft (830) having a proximal (20) and distal (40) end, a coupling body (810) at the proximal end (20) attachable in fixed relation to an end effector of the robotic system, and an end effector (840) at the distal end (40) of the shaft (830). The coupling body (810) is disposed with 4 rotary dials (a, b, c, d) to separately control revolute movement of the shaft (830) around axis (A-A') using dial "a", rotation of a gripper (c1/c2) about a $1^{st}$ revolute joint (axis B-B') using dial "b", and a separate rotation of the gripper arms (c1/c2) about a $2^{nd}$ revolute joint (axis C-C') using dials "c" and "d". In order to effect movement of the gripper arms (c1/c2) at least 4 dials must be actuated, and the shaft (830) is in revolute connection with the robotic arm via the coupling body (810) so that the pose of the shaft is in fixed relation with the pose of the end effector of the da Vinci surgical robotic system. The complexity of the coupling body is depicted in FIGS. 1D and 1E; without the cover each of the 4 rotary dials (a, b, c1, c3) is shown attached to a separate spindle (a-2, b-2, c1-2, c2-2) around which a control cord (a-4, b-4, c1-4, c2-4) is wound, and the cord pulls the relevant component to rotate it. A plurality of pulleys (b-6, c1-6, c2-6) is used to steer each cord. Equally, the complexity of the end effector (140) (FIG. 1B) is revealed also having a plurality of pulleys.

FIGS. 2A and 2B are illustrations of a robotic controllable steerable instrument (100) as described herein. It has a proximal end (20) and a distal (40) end and comprises a shaft (130), a bendable proximal part, BPP (120) and a bendable distal part, BDP (140). A connector (110) configured for dismountable attachment to the robotic arm (200) is attached in fixed rotational relation to the proximal terminal end (20) of the BPP (120). An end effector (150) is attached in fixed rotational relation to the distal terminal end (40) of the BDP (140). The shaft (130) pivots around a fulcrum zone (134).

In FIG. 2A, the BPP (120) and a BDP (140) are straight; an axis of rotation (152) of the end effector (150), a central longitudinal axis (132) of the shaft (130), and an axis of rotation (112) of the connector (110) are mutually coaxial. In FIG. 2B, the BDP (140) is bent responsive to bending of the BPP (120), and the end effector (150) is rotatable around its axis of rotation (152) when the BDP (140) is in a bent position (relative to the shaft) by a complementary rotation of the connector (110) around its axis of rotation (112). Axes of rotation (112) of the BPP (120) at different directions intersect at a zone of motion (122) along the BPP (120). In this figure, the BDP (140) bends along a curve, and not around a revolute joint; axes of rotation (112) of the BDP (140) at different directions intersect at a zone of motion (142) along the BDP (140).

FIG. 3A depicts the robot arm (200) having a base end (232) and an effector end (262), at the base end (232) the first joint is attached to a base support (234) and at the effector end (262) the last joint is attached to a fitting (260) for dismountable attachment to the steerable instrument (100). The robotic arm (200) has n joints which are kinematic pairs offering 1- or 2-DOF of movement. The kinematic pairs are preferably revolute and/or prismatic joints each offering only 1-DOF of movement.

FIGS. 3B to 3I depict schematically different configurations of a robotic arm (200) attached to a steerable instrument (100). A cylinder (220a-i) represents a revolute joint, a cuboid (220f) represents a prismatic joint, and the lines connecting the cylinders represents linkages (230a-i) of the robotic arm. The variations between the figures are in the direction of the axis of rotation or displacement of the joints, in the number of joints, and the presence or absence of a trocar (264) or of an instrument guide (266).

In FIG. 3B, the robotic arm has 7 revolute joints (220a-g) connected in tandem by 6 intervening linkages (230a-f). Each linkage is configured to maintain an orthogonal relation between the axis of rotation of the attached base end (232) joint compared with the axis of rotation of the attached effector end (262) joint. The last joint (220g) is connected to the fitting (260) for dismountable attachment to the steerable instrument (100).

FIG. 3C, the robotic arm has 7 revolute joints (220a-g) connected in tandem by 6 intervening linkages (230a-f). Each of linkages 230a-e is configured to maintain an orthogonal relation between the axis of rotation of the attached base end joint compared with the axis of rotation of the attached effector end joint. With linkages (230e-f) and the direction of the fitting (260), the axis of rotation of joints (220e-g) can be configured to intersect without collision at the BPP-CZOM (FIG. 1B, 122) of the BPP (FIG. 1B, 120). The last joint (220g) is connected to the fitting (260) for dismountable attachment to the steerable instrument (100).

Figure 16:
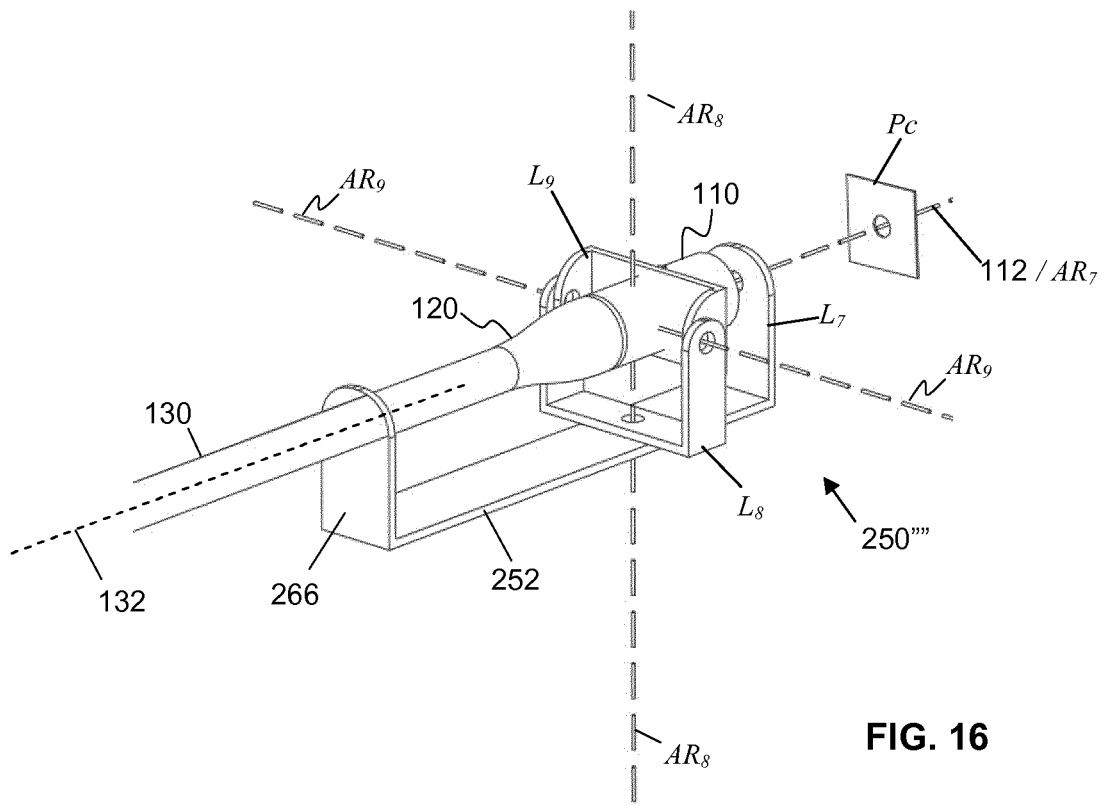

FIG. 3D, the robotic arm has 9 revolute joints (220a-g) connected in tandem by 8 intervening linkages (230a-h). Each of linkages 230a-g is configured to maintain an orthogonal relation between the axis of rotation of the attached base end joint compared with the axis of rotation of the attached effector end joint. With linkages (230g-h) and the direction of the fitting (260), the axis of rotation of joints (220g-i) can be configured to intersect without collision at the BPP-CZOM (FIG. 1B, 122) of the BPP (FIG. 16, 120). The last joint (220i) is connected to the fitting (260) for dismountable attachment to the steerable instrument (100).

FIG. 3E, the robotic arm has 8 revolute joints (220a-h) connected in tandem by 7 intervening linkages (230a-g). Each of linkages 230a-g is configured to maintain an orthogonal relation between the axis of rotation of the attached base end joint compared with the axis of rotation of the attached effector end joint. With linkage (230g) and the direction of the fitting (260), the axis of rotation of joints (220g-h) can be configured to intersect without collision at the BPP-CZOM (FIG. 1B, 122) of the BPP (FIG. 1B, 120). The last joint (220h) is connected to the fitting (260) for dismountable attachment to the steerable instrument (100).

FIG. 3F, the robotic arm has 8 revolute joints (220a-e, g-i) and 1 prismatic joint (220f) connected in tandem by 8 intervening linkages (230a-h). Each of linkages 230a-d,g,h is configured to maintain an orthogonal relation between the axis of rotation of the attached base end joint compared with the axis of rotation of the attached effector end joint. The prismatic joint (220f) changes the distance between revolute joints 220e,g. The last joint (220i) is connected to the fitting (260) for dismountable attachment to the steerable instrument (100).

FIG. 3G, the robotic arm has 9 revolute joints (220a-i) connected in tandem by 8 intervening linkages (230a-h). Each of linkages 230a-g is configured to maintain an orthogonal relation between the axis of rotation of the attached base end joint compared with the axis of rotation of the attached effector end joint. With linkages (230g-h) and the direction of the fitting (260), the axis of rotation of joints (220g-i) can be configured to intersect without collision at the BPP-CZOM (FIG. 1B, 122) of the BPP (FIG. 1B, 120). The last joint (220i) is connected to the fitting (260) for dismountable attachment to the steerable instrument (100). Further provided is a prismatic joint (220g'). One end of the prismatic joint (220f) is attached to linkage 230f so providing 3 revolute joints (220g-i) after the prismatic joint (220h') at the effector end. The other end of the prismatic joint is attached via a supporting (rigid) arm (230g') to a clamp for a trocar (264) into which the steerable instrument (100) is slidably inserted.

FIG. 3H, the robotic arm has 6 revolute joints (220a-f), one prismatic joint (220g) and 3 revolute joints (220h-j) connected in tandem by 8 intervening linkages (230a-i). Each of linkages 230a-g is configured to maintain an orthogonal relation between the axis of rotation of the attached base end joint compared with the axis of rotation of the attached effector end joint. With linkages (230g-h) and the direction of the fitting (260), the axis of rotation of joints (220*h-j*) can be configured to intersect without collision at the BPP-CZOM (FIG. 1B, 122) of the BPP (FIG. 1B, 120). The last three revolute joints (220*h-j*) are attached to the remaining revolute joints via a prismatic joint 220*g*; activation of the prismatic joint (220*g*) leads to displacement of the steerable instrument (100) in axial (A-A') direction. The last joint (220*j*) is connected to the fitting (260) for dismountable attachment to the steerable instrument (100). Further provided is a supporting (rigid) arm (230*f'*) to connect a trocar (264) to one of the linkages (230*f*). The supporting (rigid) arm (230*f'*) is provided in fixed (rotational and positional) relation to the linkage (230*f*) and trocar (264). One end of the supporting (rigid) arm (230*f*) is attached to linkage 230*f* so providing 3 revolute joints (220*h-j*) after the supporting (rigid) arm (230*f'*) at the effector end. The other end of the supporting (rigid) arm (230*f'*) is attached to a clamp for a trocar (264) into which the steerable instrument (100) is slidably inserted.

FIG. 3I, the robotic arm has 9 revolute joints (220*a-i*) connected in tandem by 8 intervening linkages (230*a-h*). Each of linkages 230*a-f* is configured to maintain an orthogonal relation between the axis of rotation of the attached base end joint compared with the axis of rotation of the attached effector end joint. With linkages (230*g-h*) and the direction of the fitting (260), the axis of rotation of joints (220*g-i*) can be configured to intersect without collision at the BPP-CZOM (FIG. 1B, 122) of the BPP (FIG. 1B, 120). The last joint (220*j*) is connected to the fitting (260) for dismountable attachment to the steerable instrument (100). Further provided is a supporting (rigid) arm (230*f'*) to connect an instrument guide (266) to one of the linkages (230*f*). The supporting (rigid) arm (230*f'*) is provided in fixed (rotational and positional) relation to the linkage (230*f*) and instrument guide (266). One end of the supporting (rigid) arm (230*f*) is attached to linkage 230*f* so providing 3 revolute joints (220*g-i*) after the supporting (rigid) arm (230*f'*) at the effector end. The other end of the supporting (rigid) arm (230*f'*) is attached to instrument guide (266) into which the steerable instrument (100) is slidably inserted. There is additionally a trocar (264).

FIG. 3J, the robotic arm has 9 revolute joints (220*a-i*) connected in tandem by 8 intervening linkages (230*a-h*). Each of linkages 230*a-f* is configured to maintain an orthogonal relation between the axis of rotation of the attached base end joint compared with the axis of rotation of the attached effector end joint. With linkages (230*g-h*) and the direction of the fitting (260), the axis of rotation of joints (220*g-i*) can be configured to intersect without collision at the BPP-CZOM (FIG. 1B, 122) of the BPP (FIG. 1B, 120). The last joint (220*j*) is connected to the fitting (260) for dismountable attachment to the steerable instrument (100) connector. Further provided is a supporting (rigid) arm (230*g"*) to connect the instrument shaft to one of the linkages (230*f*). The supporting (rigid) arm (230*g"*) is provided in fixed (rotational and positional) relation to the linkage (230*g*) and a coupling to the instrument shaft. One end of the supporting (rigid) arm (230*g"*) is attached to linkage 230*g* so providing 2 revolute joints (220*h-i*) after the supporting (rigid) arm (230*g"*) at the effector end. The other end of the supporting (rigid) arm (230*g"*) is attached to a coupling for the instrument shaft that puts the shaft and linkage (230*g*) in fixed position and rotational alignment.

FIG. 3K, the robotic arm has 6 revolute joints (220*a-f*) connected in tandem by 7 intervening linkages (230*a-g*). Each of linkages 230*a-f* is configured to maintain an orthogonal relation between the axis of rotation of the attached base end joint compared with the axis of rotation of the attached effector end joint. The robotic arm last joint (220*g*) is connected to an adapter (250) comprising three prismatic joints (P-a, -b, -c) arranged in parallel, so forming a multipod mechanism. The three prismatic joints (P-a, -b, -c) are attached at a distal end common footplate (274) and at a proximal end to a common waist plate (272). The common footplate (274) is connected to the fitting (260) for dismountable attachment to the steerable instrument (100) connector.

FIG. 3L, shows the robotic arm of FIG. 3K, provided with a supporting (rigid) arm (252) connected at a distal end to an instrument guide (266) and at the other end to a proximal end of the multipod adapter (250) i.e. to the distal end of joint 220*g*. The supporting (rigid) arm (252) is non-adjustable. The instrument guide (266) is effectively in fixed positional and rotational relation with the common waist plate (272) of the adapter (250).

FIG. 3M, shows the robotic arm of FIG. 3L, provided with a supporting arm (252) that is adjustable, having two linkages (-a, -b) joined by a ball-and-socket joint (253). The supporting arm (252) is adjustable, allowing the direction of the instrument guide (266) to be set and locked relation with the common waist plate (272).

FIG. 3N, is similar to the robotic arm of FIG. 3L, except the supporting arm (252) connected at a distal end to a trocar (264), or to an instrument guide (266) holding the trocar (264).

FIG. 3O, shows the robotic arm of FIG. 3N, provided with a supporting arm (252) that is adjustable, having two linkages (-a, -b) joined by a ball-and-socket joint (253). The supporting arm (252) is adjustable, allowing the direction of the trocar (264), or instrument guide (266) holding the trocar (264) to be set and locked relation with the common waist plate (272).

FIG. 3P, shows the robotic arm of FIG. 3N, provided with a supporting arm (252) that is adjustable, having five linkages (252-*a* to -*e*) joined by revolute joints (253-*a* to -*d*). The joints are actuated or driven e.g. motorised.

FIG. 3Q, shows the robotic arm of FIG. 3N, provided with a supporting arm (252) that is adjustable, having five linkages (252-*a* to -*d*) joined by 2 revolute joints (253-*a* and -b), and one prismatic joint (P-a). The joints are actuated or driven e.g. motorised.

FIG. 3R, shows the robotic arm of FIG. 3N, provided with a supporting arm (252) that is adjustable, having seven linkages (252-*a* to -*g*) joined by 7 revolute joints (253-*a* to -*g*). The joints are actuated or driven e.g. motorised. The supporting arm (252) at its proximal end is attached is disposed in relation to a base of the robotic arm; the supporting arm may be a second robotic arm.

Figure 4A:
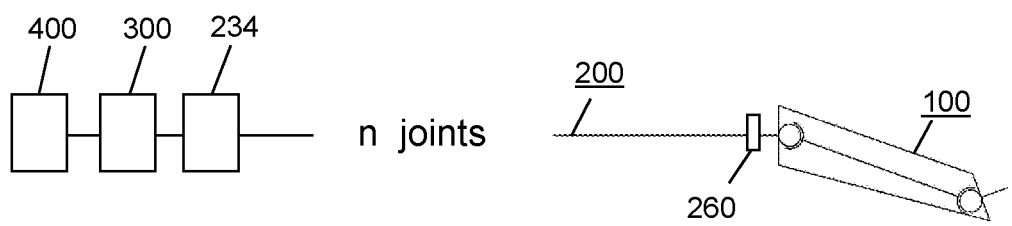
FIG. 4A is a schematic illustration of the robotic arm connected to a control unit and manual input unit.

FIG. 4A is a schematic illustration of the robotic arm (200) where the first joint is attached to a base support (234) and the last joint is attached to a fitting (260) for dismountable attachment to the steerable instrument (100). The robotic arm (200) is controlled by signals generated by a control unit (300), and the control unit (300) receives signal from a manual input unit (400) to manually control movement of the steerable instrument (100). The manual input is provided by manual input of the operator, e.g. hands, feet.

Figure 4B:
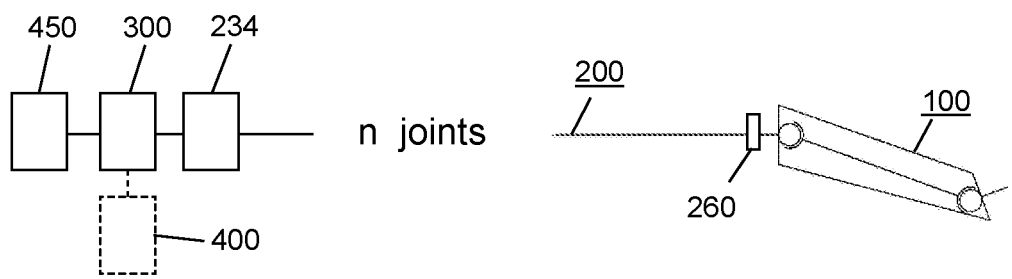
FIG. 4B is a schematic illustration of the robotic arm connected to a control unit, a contactless measurement unit and optionally to a manual input unit.

FIG. 4B is a schematic illustration of the robotic arm (200) where the first joint is attached to a base support (234) and the last joint is attached to a fitting (260) for dismountable attachment to the steerable instrument (100). The control unit (300) is attached to a contactless measurement unit (450) that dimensionally measures the operating volume. The robotic arm (200) is controlled by signals generated by the control unit (300), and the control unit (300) receives signal from contactless measurement unit (450). Using a machine learning protocol, the control unit automatically controls the robotic arm (200) to perform the desired operation, using signals received from the contactless measurement unit (450). A possibility to over-ride the automatic operation is provided by the manual input unit (400) connected to the control unit (300).

Figure 5:
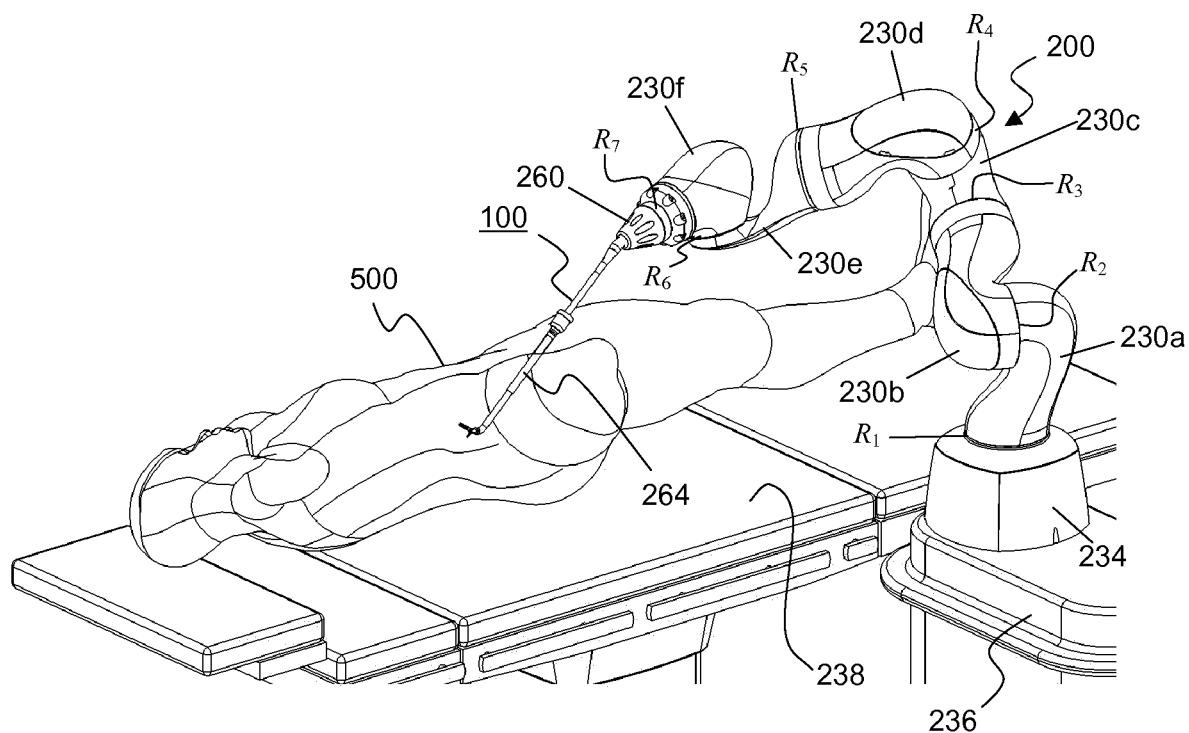
FIG. 5 depicts an exemplary robotic arm attached at one end to a base mounted on a trolley moveable in relation to an operating table on which a subject is placed, and attached at the other end to the steerable instrument.

FIG. 5 depicts an exemplary robotic arm (200) attached to a base (234) mounted on a trolley (236) moveable in relation to an operating table (238) on which a subject (500) is placed. The robotic arm (200) comprises 7 revolute joints ($R_1$-$R_7$) connected by intervening linkages (230a-f), akin to the arrangement of 7 revolute joints (220a-g) and intervening linkages (230a-f) of FIG. 2B. The steerable instrument (100) is attached to the fitting (260) in connection with the last revolute joint ($R_7$) and passes through a trocar (264) inserted into the subject abdominal cavity through the skin.

Figure 6:
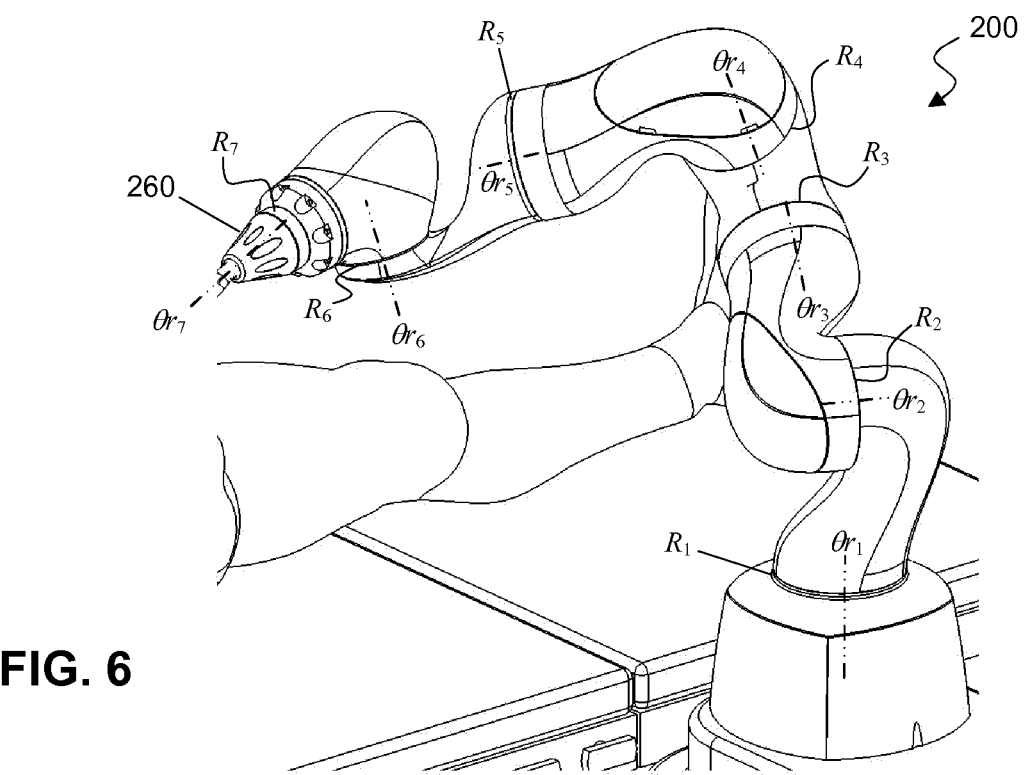
FIG. 6 is a detailed view of the robotic arm of FIG. 5.

FIG. 6 is a detailed view of the robotic arm (200) of FIG. 5, with the revolute joints indicated ($R_1$-$R_7$) and the corresponding revolute axes of rotation ($\theta_{r1-7}$).

Figure 7:
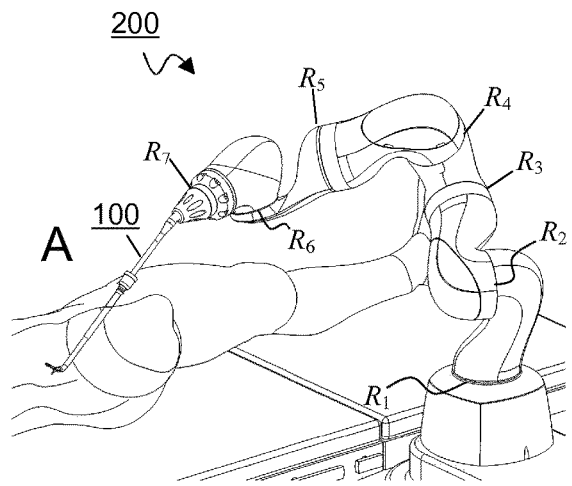
FIG. 7 illustrates different poses (A, B, C) of the robotic arm to achieve different rotations (A', B', C') of the end effector.
Figure 7:
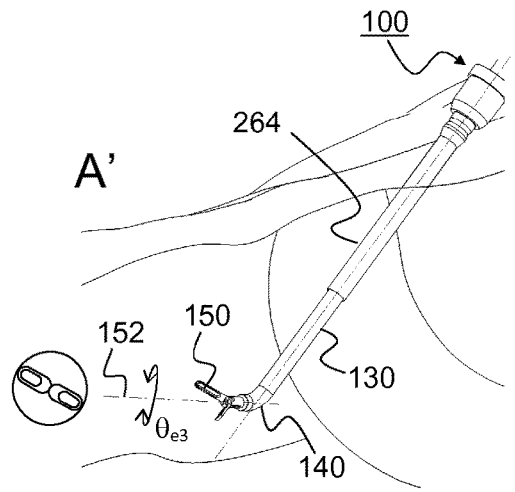
Figure 7:
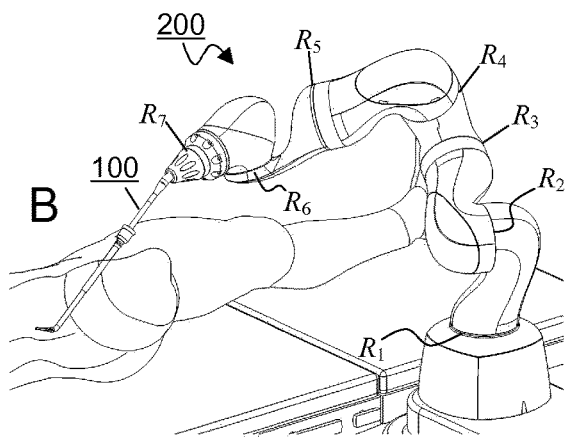
Figure 7:
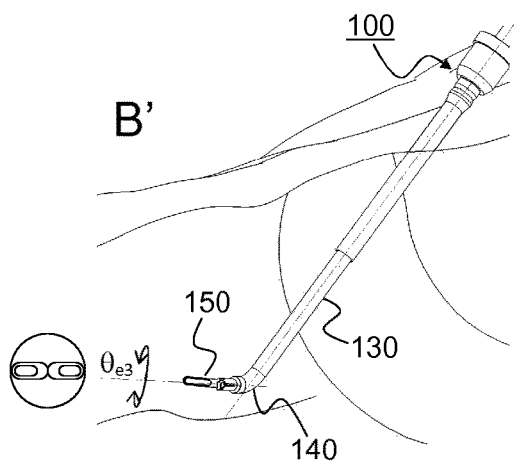
Figure 7:
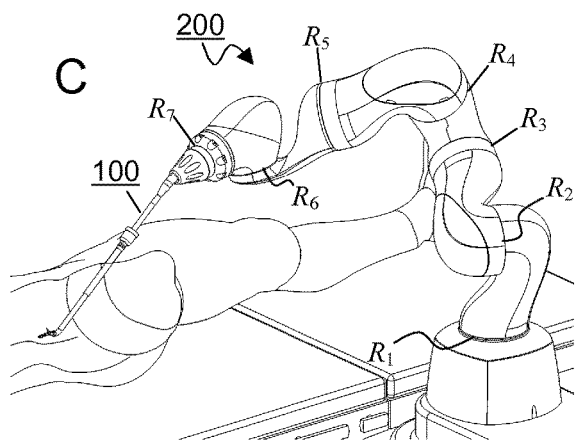
Figure 7:
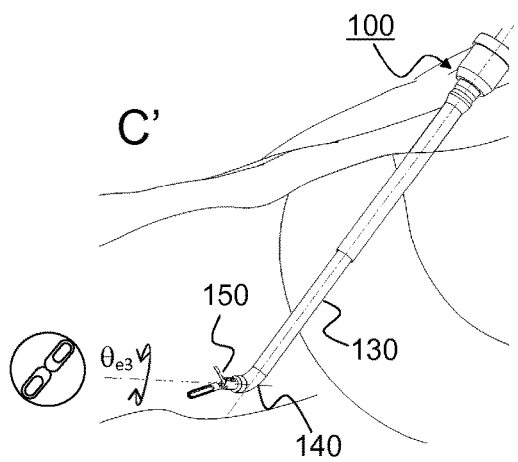

FIG. 7 illustrates different poses (A, B, C) of the robotic arm (200) to achieve a rotation of the end effector (150) when the BDP (140) is in a bent position (A', B', C') while maintaining the same shaft direction (130) and direction of the rotational axis (152) of the end effector (150, $\theta_{e3}$). Rotation of the end effector (150) is achieved by rotation of revolute joint ($R_7$) transmitted to the steerable instrument (100) via the connector. Assuming arbitrary frames of reference for angles that define the direction of the shaft ($\theta_{s1}$, $\theta_{s2}$, $\theta_{s3}$—see FIG. 9), direction of the end effector ($\theta_{e1}$, $\theta_{e2}$, $\theta_{e3}$—see FIGS. 7, 8), and joint angles ($R_1$-$\theta_{r1}$, $R_2$-$\theta_{r2}$, $R_3$-$\theta_{r3}$, $R_4$-$\theta_{r4}$, $R_5$-$\theta_{r5}$, $R_6$-$\theta_{r6}$, $R_7$-$\theta_{r7}$—see FIG. 6), angles of the robotic arm (200) joints that define pose of the steerable instrument (100) in FIG. 7 are set out in Table 1. The same frames of reference have been used in FIGS. 8 and 9.

TABLE 1

Robotic arm joint angles corresponding instrument poses of FIG. 7

| | Robotic arm joint angles | | | | | | | | Steerable Instrument | | | | | |
| | | | | | | | | | Shaft | | | End effector | | |
| FIG. 7 | $\theta_{r1}$ | $\theta_{r2}$ | $\theta_{r3}$ | $\theta_{r4}$ | $\theta_{r5}$ | $\theta_{r6}$ | $\theta_{r7}$ | FIG. 7 | $\theta_{s1}$ | $\theta_{s2}$ | $\theta_{s3}$ | $\theta_{e1}$ | $\theta_{e2}$ | $\theta_{e3}$ |
|---|---|---|---|---|---|---|---|---|---|---|---|---|---|---|
| A | 51.07° | 38.00° | 52.76° | 84.36° | 8.72° | 78.96° | −19.51° | A' | 50.4° | 50.42° | 7.73° | 60.00° | 12.34° | 0.00° |
| B | 51.07° | 38.00° | 52.76° | 84.36° | 8.72° | 78.96° | 24.94° | B' | 50.4° | 50.42° | 7.73° | 60.00° | 12.34° | 45.00° |
| C | 51.07° | 38.00° | 52.76° | 84.36° | 8.72° | 78.96° | 69.88° | C' | 50.4° | 50.42° | 7.73° | 60.00° | 12.34° | 90.00° |

Figure 8:
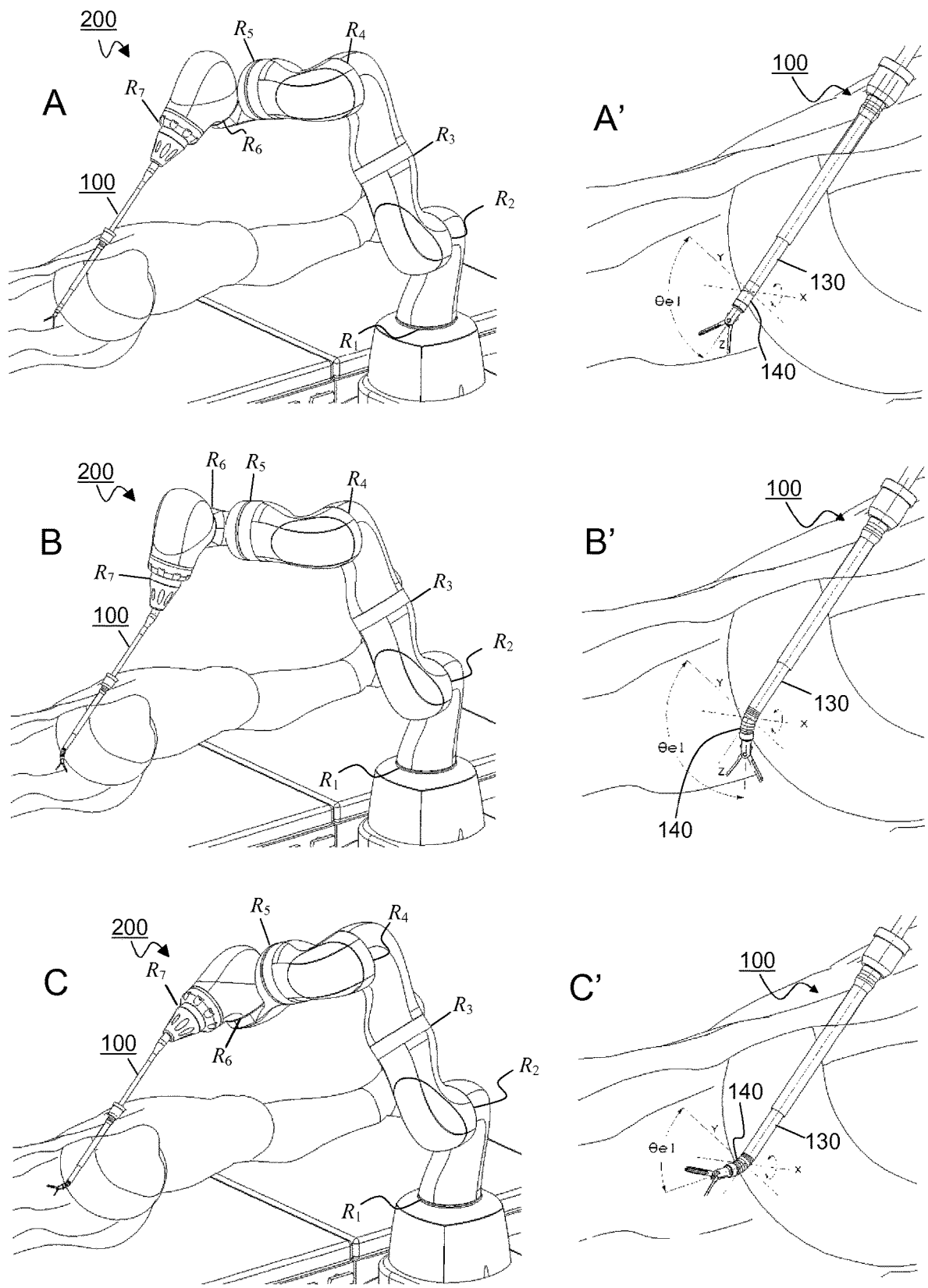
FIG. 8 illustrates different poses (A, B, C) of the robotic arm to bend the BDP in different directions (A', B', C').

FIG. 8 illustrates different poses (A, B, C) of the robotic arm (200) to bend the BDP (140, $\theta_{e1}$, $\theta_{e2}$) in different directions (A', B', C') while maintaining the same shaft (130) direction and revolute angle of the end effector. Bending of the BDP (140) is achieved by rotation of revolute joints ($R_1$ to $R_7$) that is transmitted to the steerable instrument (100) via the connector. Assuming an arbitrary frame of reference for angles that define the direction of the shaft ($\theta_{s1}$, $\theta_{s2}$, $\theta_{s3}$—see FIG. 9), direction of the end effector ($\theta_{e1}$, $\theta_{e2}$, $\theta_{e3}$—see FIGS. 7, 8), and joint angles ($R_1$-$\theta_{r1}$, $R_2$-$\theta_{r2}$, $R_3$-$\theta_{r3}$, $R_4$-$\theta_{r4}$, $R_5$-$\theta_{r5}$, $R_6$-$\theta_{r6}$, $R_7$-$\theta_{r7}$—see FIG. 6), angles of the robotic arm (200) joints that define pose of the steerable instrument (100) in FIG. 8 are indicated in Table 2. The same frames of reference have been used in FIGS. 7 and 8.

TABLE 2

Robotic arm joint angles corresponding instrument poses of FIG. 8

| | Robotic arm joint angles | | | | | | | | Steerable Instrument | | | | | |
| | | | | | | | | | Shaft | | | End effector | | |
| FIG. 8 | $\theta_{r1}$ | $\theta_{r2}$ | $\theta_{r3}$ | $\theta_{r4}$ | $\theta_{r5}$ | $\theta_{r6}$ | $\theta_{r7}$ | FIG. 8 | $\theta_{s1}$ | $\theta_{s2}$ | $\theta_{s3}$ | $\theta_{e1}$ | $\theta_{e2}$ | $\theta_{e3}$ |
|---|---|---|---|---|---|---|---|---|---|---|---|---|---|---|
| A | 70.07 | 40.59 | 80.38 | 62.43 | 36.37 | 78.00 | 15.04 | A' | 48.02 | 44.60 | 17.09 | 90.00 | 90.00 | 0.00 |
| B | 69.06 | 46.94 | 87.61 | 44.67 | 63.79 | 91.94 | 30.27 | B' | 48.02 | 44.60 | 17.09 | 135.00 | 90.00 | 0.00 |
| C | 71.04 | 39.13 | 77.68 | 75.60 | 8.49 | 74.34 | 3.87 | C' | 48.02 | 44.60 | 17.09 | 45.00 | 90.00 | 0.00 |

Figure 9:
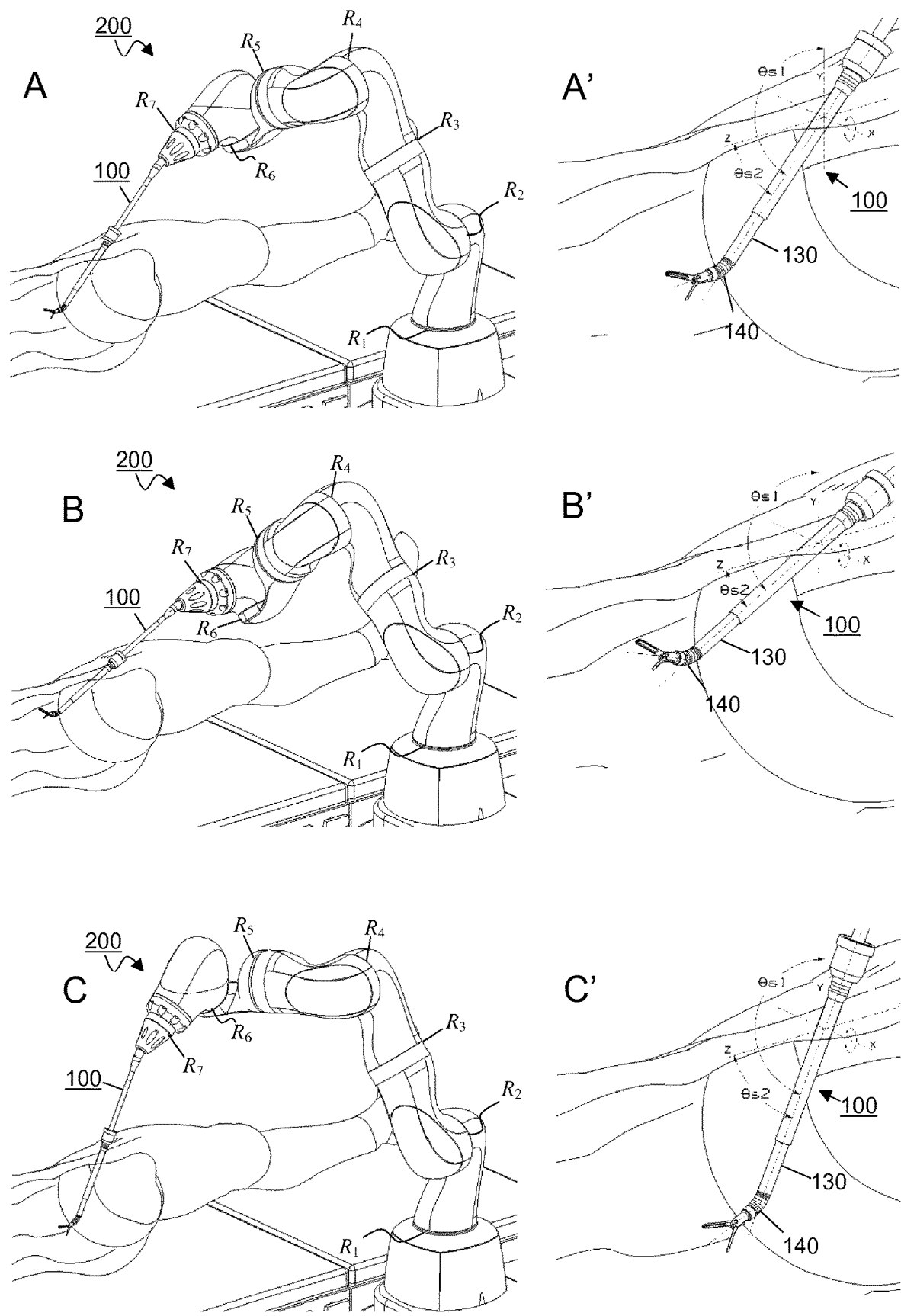
FIG. 9 illustrates different poses (A, B, C) of the robotic arm that effects different directions (A', B', C') of the shaft.

FIG. 9 illustrates different poses (A, B, C) of the robotic arm (200) that effects different directions of the shaft (130, $\theta_{s1}$, $\theta_{s2}$) (A', B', C') while maintaining the same direction of the end effector (150) and revolute angle of the end effector. A shaft direction is achieved by rotation of revolute joints ($R_1$ to $R_7$) that is transmitted to the steerable instrument (100) via the connector. Assuming an arbitrary frame of reference for angles that define the direction of the shaft ($\theta_{s1}$, $\theta_{s2}$, $\theta_{s3}$—see FIG. 9), direction of the end effector ($\theta_{e1}$, $\theta_{e2}$, $\theta_{e3}$—see FIGS. 7, 8), and joint angles ($R_1$-$\theta_{r1}$, $R_2$-$\theta_{r2}$, $R_3$-$\theta_{r3}$, $R_4$-$\theta_{r4}$, $R_5$-$\theta_{r5}$, $R_6$-$\theta_{r6}$, $R_7$-$\theta_{r7}$—see FIG. 6), angles of the robotic arm (200) joints that define pose of the steerable instrument (100) in FIG. 9 are indicated in Table 3. The same frames of reference have been used in FIGS. 7 and 8.

FIGS. 14 to 17 illustrate a configuration of the robotic arm (200) wherein the axes of rotation of the last three revolute joints (with axes of rotation $AR_7$, $AR_8$, $AR_9$) intersect. They intersect in the BPP (120) of the steerable instrument (200), in particular at the zone of motion (122), more precisely at the BPP-CZOM. Rotation of the three joints (with axes of rotation $AR_7$, $AR_8$, $AR_9$) controls bending of the BPP and BDP, and rotation of the end effector (150). The last two joints (with axes of rotation $AR_8$, $AR_9$) are provided by an adapter (250) that connects to an end effector of an existing robotic arm (200') at joint with axis of rotation $AR_7$, providing control over two additional revolute joints (with axes of rotation $AR_8$, $AR_9$). The robotic arm has effectively 9 revolute joints. Linkage $L_7$ attaches on one side (proximal) to an existing robotic arm (providing rotation around $AR_7$)

TABLE 3

Robotic arm joint angles corresponding instrument poses of FIG. 9

| | Robotic arm joint angles | | | | | | | | Steerable Instrument | | | | | |
| | | | | | | | | | Shaft | | | End effector | | |
| FIG. 9 | $\theta_{r1}$ | $\theta_{r2}$ | $\theta_{r3}$ | $\theta_{r4}$ | $\theta_{r5}$ | $\theta_{r6}$ | $\theta_{r7}$ | FIG. 9 | $\theta_{s1}$ | $\theta_{s2}$ | $\theta_{s3}$ | $\theta_{e1}$ | $\theta_{e2}$ | $\theta_{e3}$ |
|---|---|---|---|---|---|---|---|---|---|---|---|---|---|---|
| A | 66.70° | 39.89° | 76.07° | 81.44° | 2.53° | 71.12° | 10.82° | A' | 42.99° | 42.22° | 8.85° | 42.00° | 5.00° | 30.00° |
| B | 69.89° | 49.77° | 73.99° | 81.46° | 12.29° | 86.97° | 0.17° | B' | 28.30° | 26.78° | 9.04° | 42.00° | 5.00° | 30.00° |
| C | 64.42° | 35.25° | 85.68° | 71.01° | 35.39° | 58.34° | 39.58° | C' | 62.94° | 62.76° | 10.07° | 42.00° | 5.00° | 30.00° |

Figure 10:
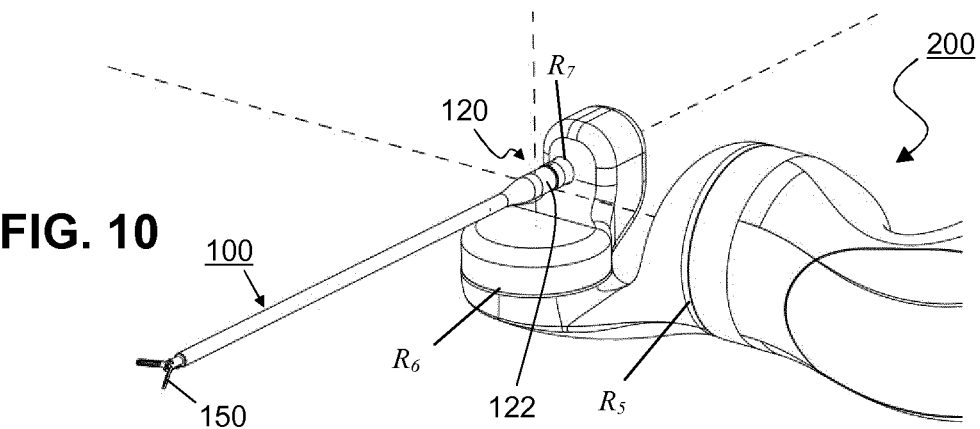
FIG. 10 illustrates a configuration of the robotic arm wherein the axes of rotation of the last three revolute joints ($R_5$, $R_6$, $R_7$) intersect.

FIG. 10 illustrates a configuration of the robotic arm (200) wherein the axes of rotation of the last three revolute joints ($R_5$, $R_6$, $R_7$) intersect. They intersect in the BPP (120) of the steerable instrument (200), in particular at the zone of motion (122), more precisely at the BPP-CZOM. Rotation of the three joints ($R_5$, $R_6$, $R_7$) controls bending of the BPP and BDP, and rotation of the end effector (150). The last three joints ($R_5$, $R_6$, $R_7$) may be configured by adapting an existing robotic arm (200).

Figure 11:
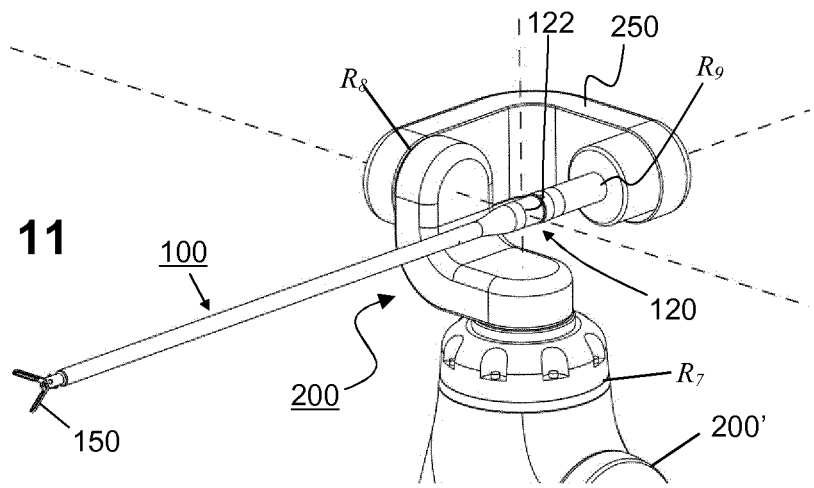
FIG. 11 illustrates a configuration of the robotic arm wherein the last two joints ($R_8$, $R_9$) are provided by an adapter.

FIG. 11 illustrates a configuration of the robotic arm (200) wherein the axes of rotation of the last three revolute joints ($R_7$, $R_8$, $R_9$) intersect. They intersect in the BPP (120) of the steerable instrument (200), in particular at the zone of motion (122), more precisely at the BPP-CZOM. Rotation of the three joints ($R_7$, $R_8$, $R_9$) controls bending of the BPP and BDP, and rotation of the end effector (150). The last two joints ($R_8$, $R_9$) are provided by an adapter (250) that connects to an end effector of an existing robotic arm (200') at $R_7$, providing control over two additional revolute joints ($R_8$, $R_9$). The robotic arm has effectively 9 revolute joints.

Figure 12:
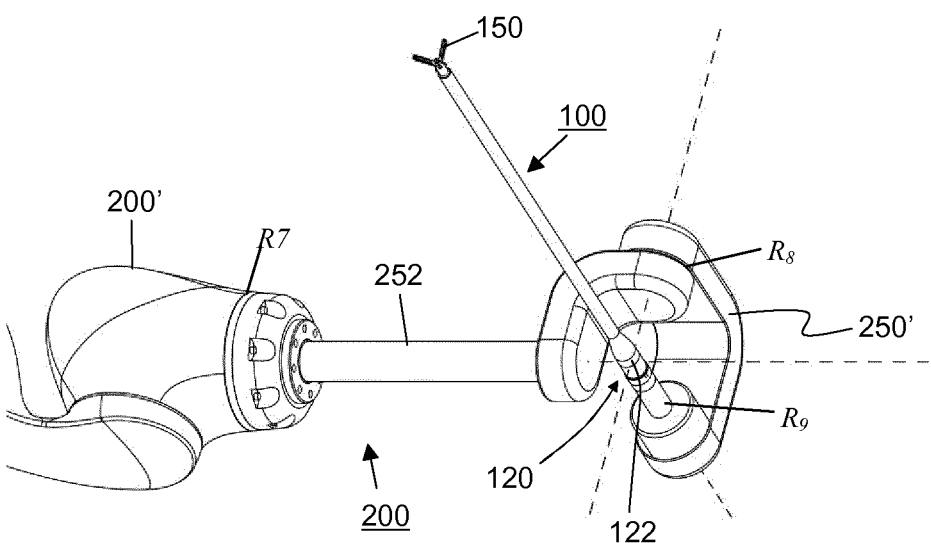
FIG. 12 illustrates a configuration of the robotic arm similar to FIG. 11; a link connecting $R_7$ and $R_8$ is extended to avoid collision of the steerable instrument with the existing robotic arm.

FIG. 12 shows a configuration similar to FIG. 11. The last two joints ($R_8$, $R_9$) are provided by an adapter (250') that connects to an end effector of an existing robotic arm (200') at $R_7$, providing control over two additional revolute joints ($R_8$, $R_9$), whereby a link connecting $R_7$ and $R_8$ is extended to avoid collision of the steerable instrument (100) with the existing robotic arm (200') and/or with another robotic arm.

Figure 13:
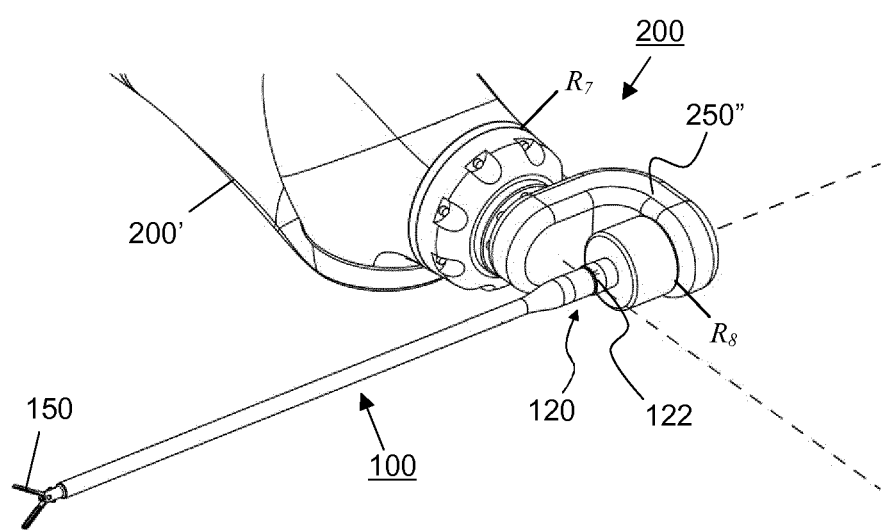
FIG. 13 illustrates a configuration of the robotic arm wherein last joint ($R_7$) is provided by an adapter.

FIG. 13 illustrates a configuration of the robotic arm (200) wherein the axes of rotation of the last two revolute joints ($R_7$, $R_8$) intersect. They intersect in the BPP (120) of the steerable instrument (100), in particular at the zone of motion (122), more precisely at the BPP-CZOM. Rotation of the two joints ($R_7$, $R_8$) controls bending of the BPP and BDP, and rotation of the end effector (150). The last joint ($R_7$) is provided by an adapter (250") that connects to an end effector of an existing robotic arm (200') at $R_7$, providing control over one additional revolute joints ($R_8$). The robotic arm has effectively 8 revolute joints.

and on the other side (distal) to joint with axis of rotation $AR_8$. Linkage $L_8$ attaches on one side (proximal) to joint with axis of rotation $AR_8$ and on the other side (distal) to joint with axes of rotation $AR_9$. Linkage $L_9$ attaches on one side (proximal) to joint with axes of rotation $AR_9$ and on the other side (distal) to a fitting for the connector (110). The adapter is configured such that the axis of rotation of the distal-most joint (with axes of rotation $AR_9$) of the adapter is disposed perpendicular to a central axis of the proximal tip of the connector (110). It is further shown that the axis of rotation of the distal-most joint (with axes of rotation $AR_9$) of the adapter is disposed parallel to a plane (Pc) perpendicular to central axis (112) of the connector (110). The parallel or perpendicular relationship is maintained in bent (FIGS. 15 and 17) and straight instrument (FIGS. 14 and 16).configurations. It can be seen that the central axis of the shaft (132) and the rotational axis ($R_7$) are parallel or coaxial.

Figure 17:
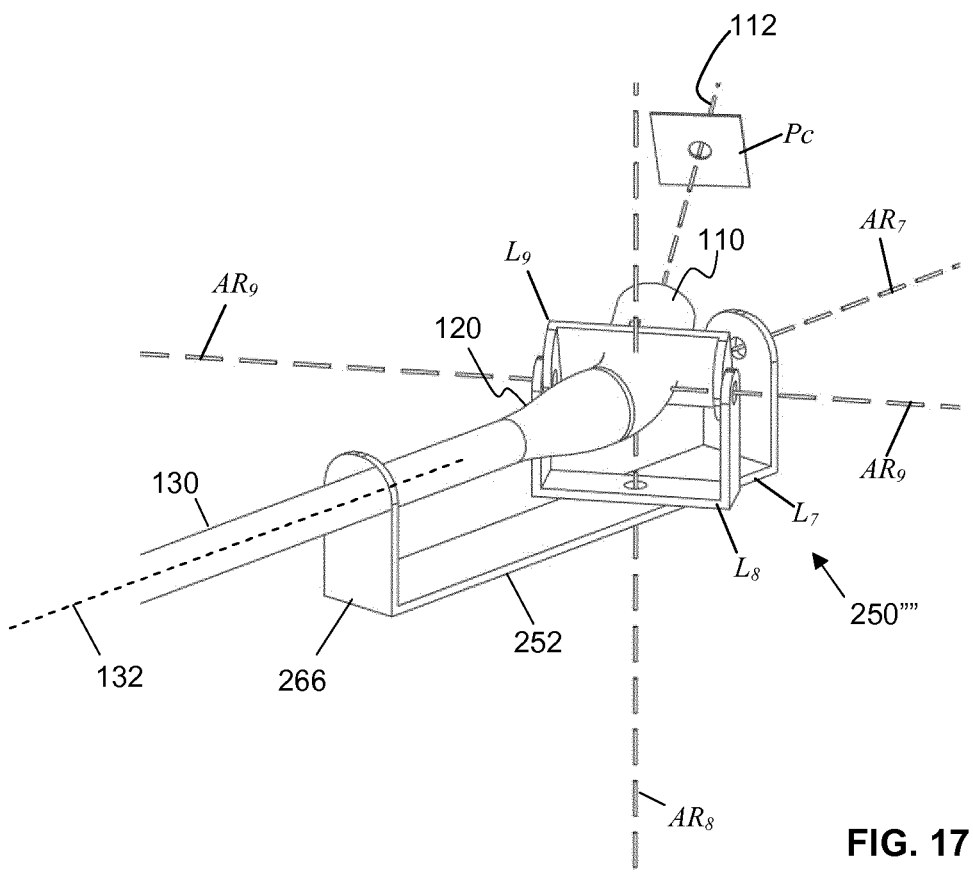

FIGS. 16 and 17 additionally depict the proximal-most link ($L_7$) of the proximal most joint (La) of the adapter provided with a distally extending arm (252) and coupling (254) for the instrument shaft (130) in order to retain the instrument shaft (130) in fixed positional and rotational relation with the proximal-most link ($L_7$) of the proximal most joint ($R_8$) of the adaptor (250"").

Figure 18:
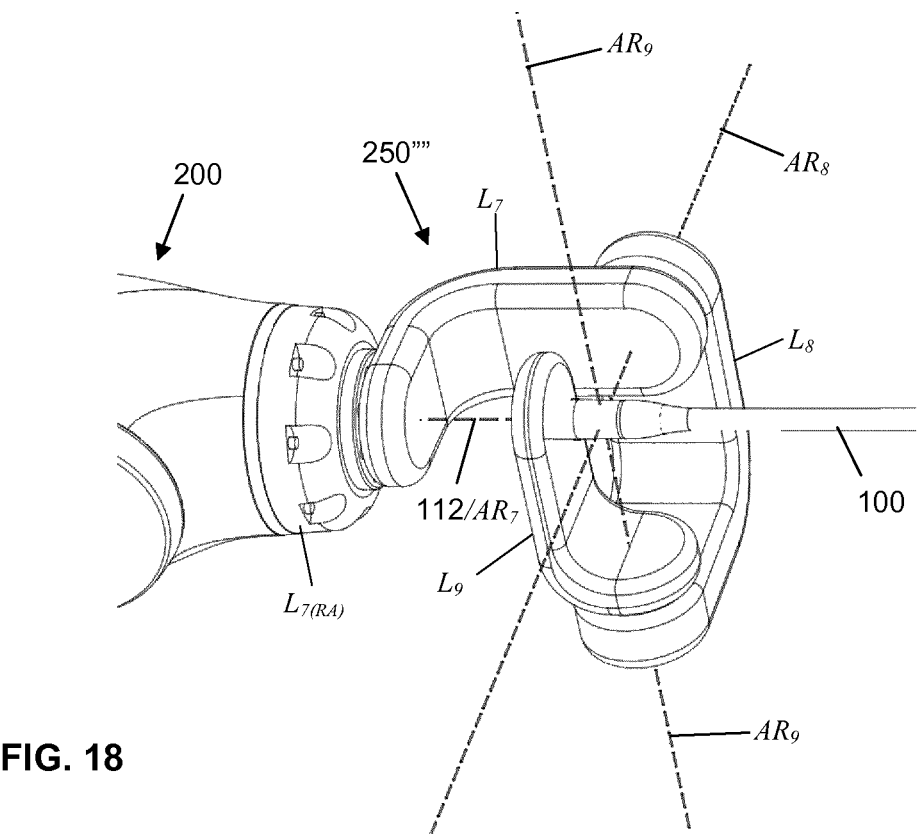
FIGS. 18 and 19 are an isometric views of alternative configurations of an adapter according to FIG. 14 or 15.

FIG. 18 is an isometric view of an implementation of an adapter according to FIG. 14 or 15.

Figure 19:
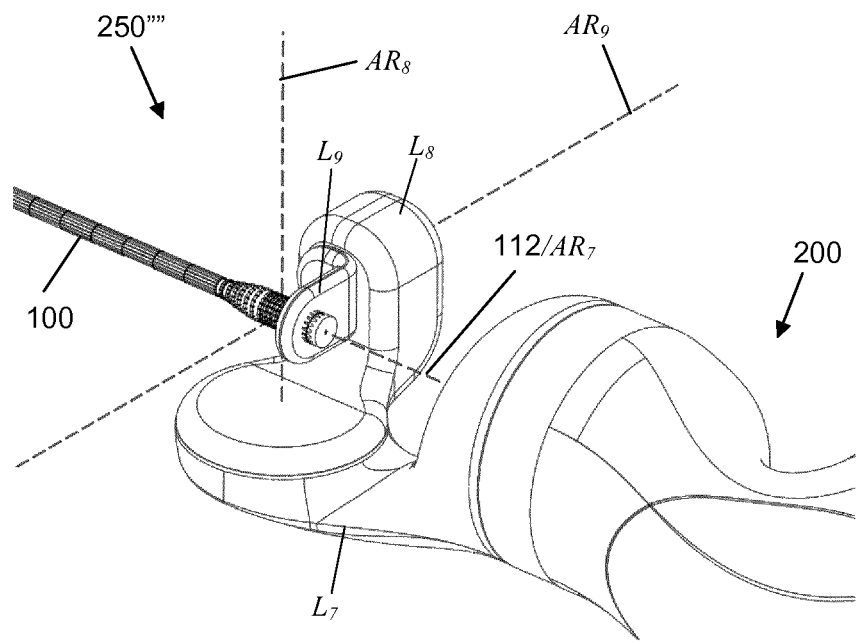

FIG. 19 is isometric view of another implementation of an adapter according to FIG. 14 or 15.

Figure 21:
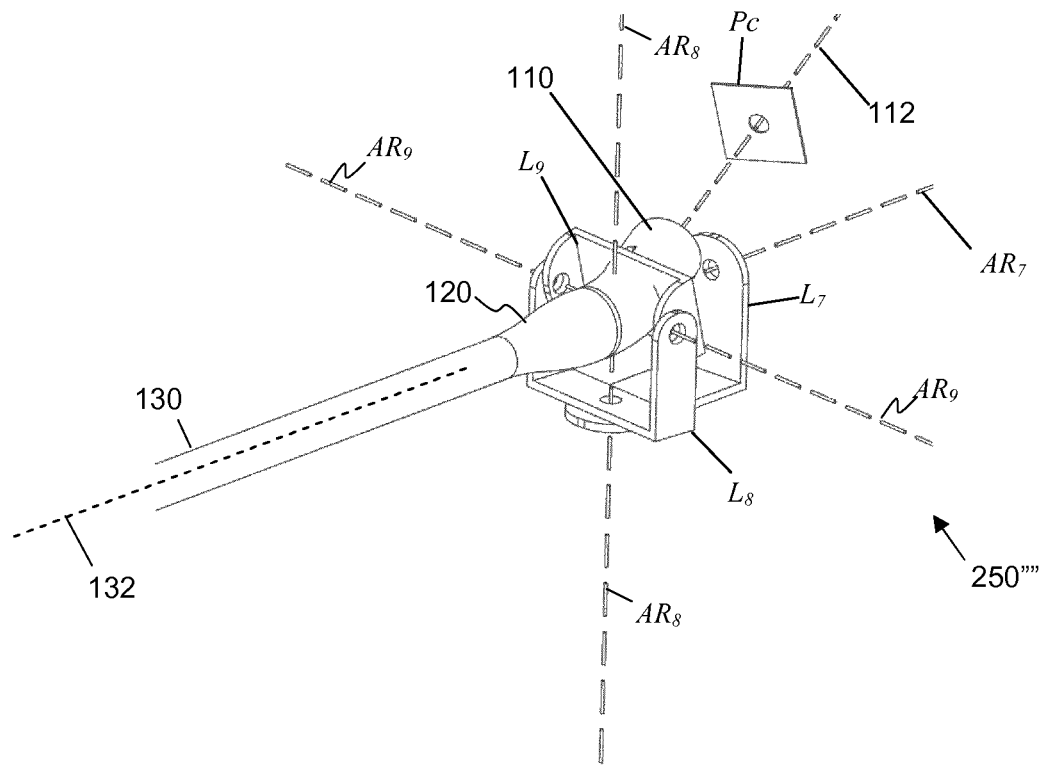

FIGS. 20 and 21 are similar to FIGS. 14 and 15, except the axis of rotation of the distal-most joint of the adapter (e.g. $AR_9$) is disposed non-perpendicular to a central axis (112) of the connector (110). In this case there is an angle of 20 deg from a perpendicular alignment. The axis of rotation of the distal-most joint of the adapter (e.g. $AR_9$) is disposed inclined at an angle of 20 deg to the plane (Pc) perpendicular to the central axis (112) of the connector (110).

Figure 22:
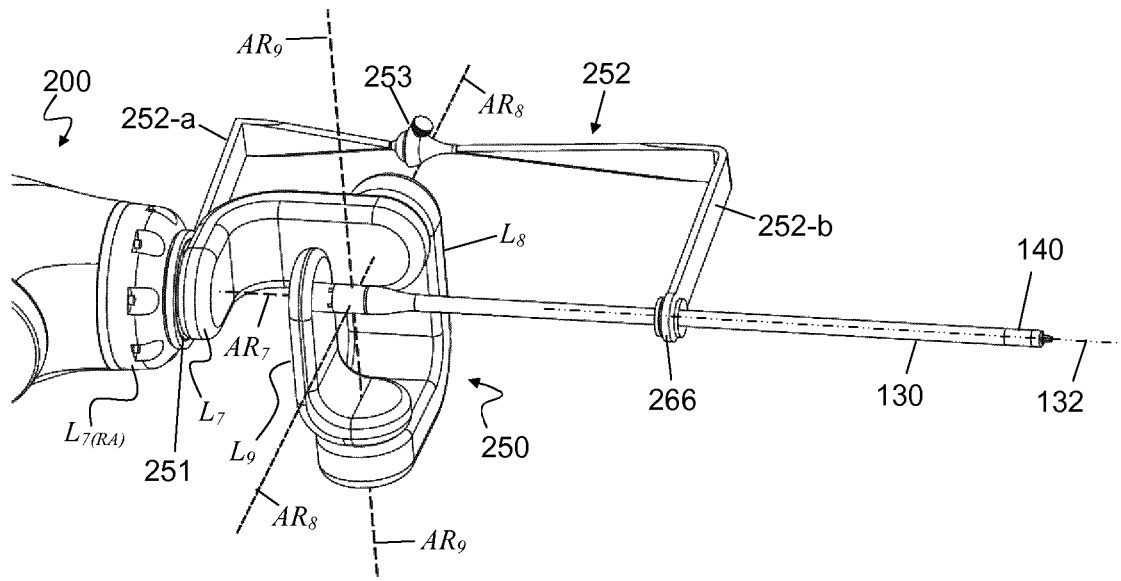
FIGS. 22 to 25 show different actuation positions of the adaptor (250) shown in FIG. 18, wherein the adaptor (250) is further provided with an adjustable supporting arm.
Figure 23:
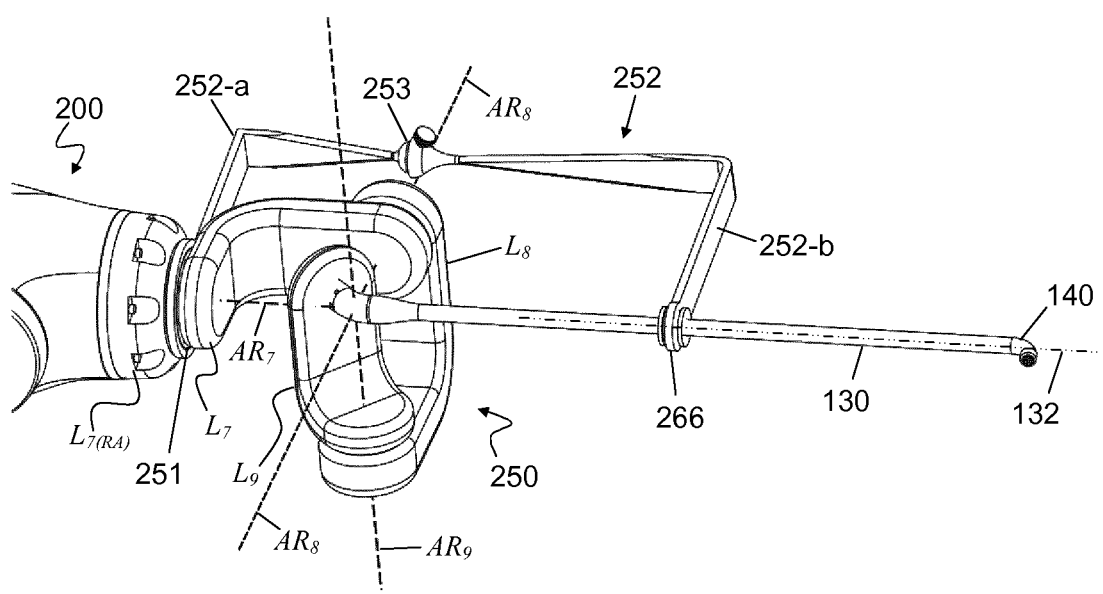
Figure 24:
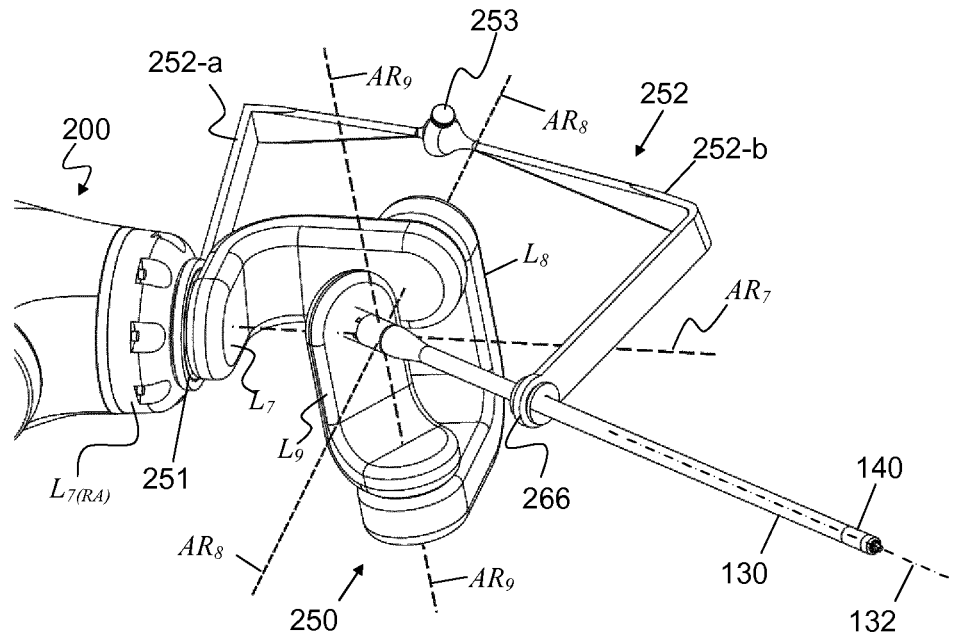
Figure 25:
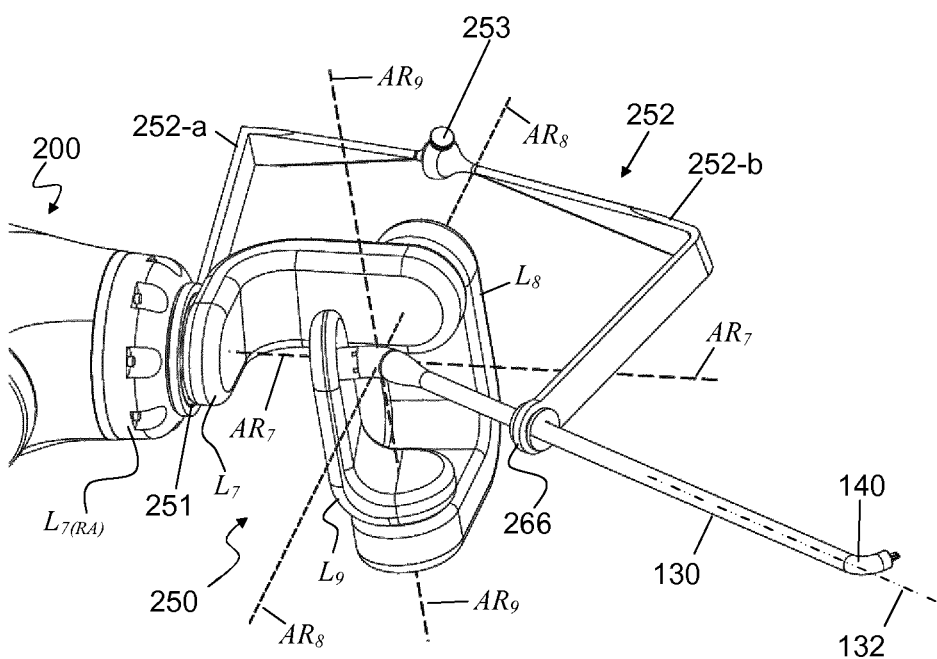

FIGS. 22 to 25 show different actuation positions of the adaptor (250) shown in FIG. 18, wherein the adaptor (250) is further provided with an adjustable supporting arm (252) having two rigid linkages (252-a and -b) joined by a ball-and-socket joint (253). whose position is repeatably lockable. Disposed at a distal end of the adjustable supporting arm (252-a, -b) is an instrument guide (266) dismountably attached in fixed relation to the instrument shaft (130) and at the proximal end with an attachment (251) to the $1^{st}$ (proximal most) linkage ($L_7$) of the adapter (250). The instrument guide (266) is effectively in fixed positional and rotational relation with the $1^{st}$ (proximal most) linkage ($L_7$) of the adapter (250). In FIGS. 22 and 23 the adjustable supporting arm (252) is set such that the instrument shaft (130) central axis (132) is co-axial with the axis of rotation ($AR_7$) of the last link ($L_{7(RA)}$) of the robotic arm (200) when the distal bendable part (140) is both straight (FIG. 22) and bent (FIG. 23). In FIGS. 24 and 25 the adjustable 252 arm (252) is set such that the instrument shaft (130) central axis (132) is inclined with the axis of rotation ($AR_7$) of the last link ($L_{7(RA)}$) of the robotic arm (200) when the distal bendable part (140) is both straight (FIG. 22) and bent (FIG. 23).

FIG. 26 depicts an adapter (250) comprising three prismatic joints ($P_{8a}$, $P_{8b}$, $P_{8c}$) attached at a proximal end to a common waist plate (272) and at a distal end to a common footplate (274) by revolute joints. Each prismatic joint has a proximal link ($L_{8a}$, $L_{8b}$, $L_{8c}$) and a distal link ($L_{9a}$, $L_{9b}$, $L_{9c}$)—the distal link ($L_{9a}$, $L_{9b}$, $L_{9c}$) slides into the proximal link ($L_{8a}$, $L_{8b}$, $L_{8c}$). The waist plate (272) is in fixed positional and rotational relation with the last linkage ($L_{7(RA)}$) of the robotic arm (200). The footplate (274) is in fixed positional and rotational relation with the connector of the instrument (100). Controlled movement of the three prismatic joints ($P_{8a}$, $P_{8b}$, $P_{8c}$) causes tilting of the footplate (274), which in turn actuates the proximal bendable part (120) of the instrument (100).

Figure 29:
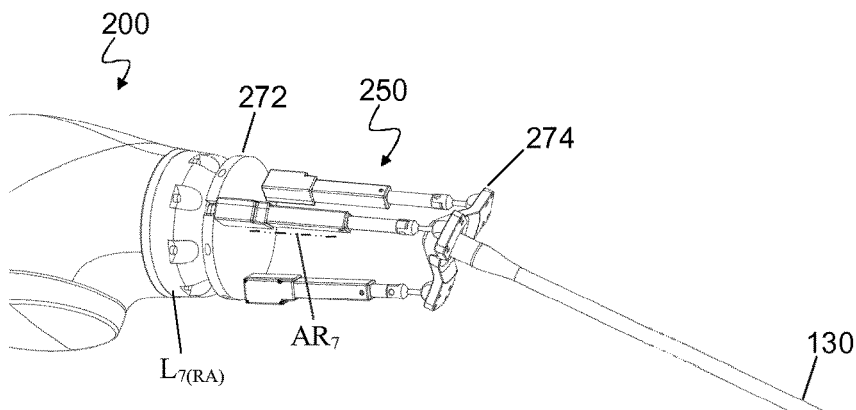
Figure 30:
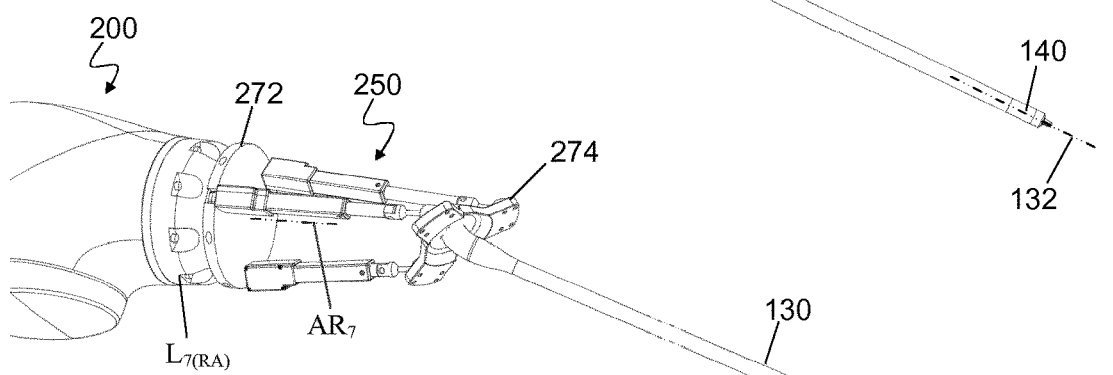
Figure 31:
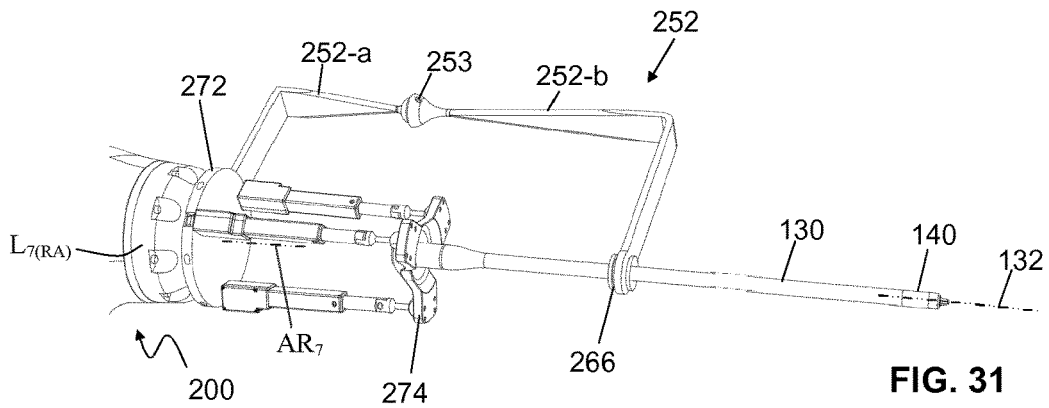
FIGS. 31 to 34 show different actuation positions of the adaptor (250) shown in FIG. 26, wherein the adaptor (250) is further provided with an adjustable supporting arm (252-a, -b).
Figure 32:
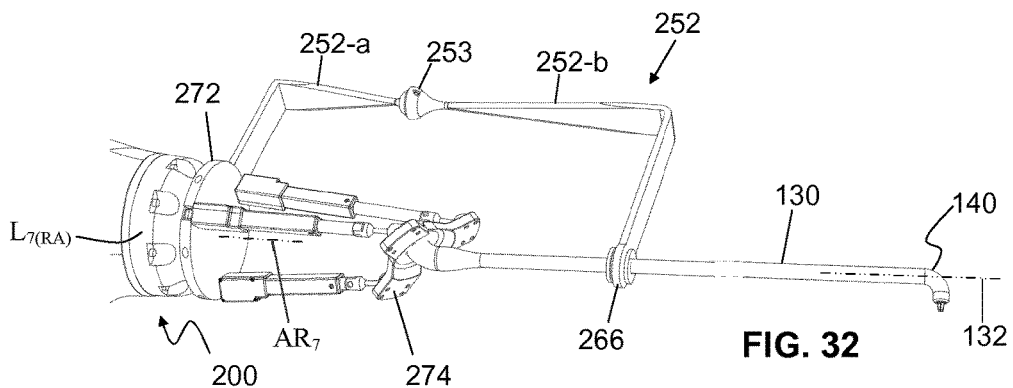
Figure 33:
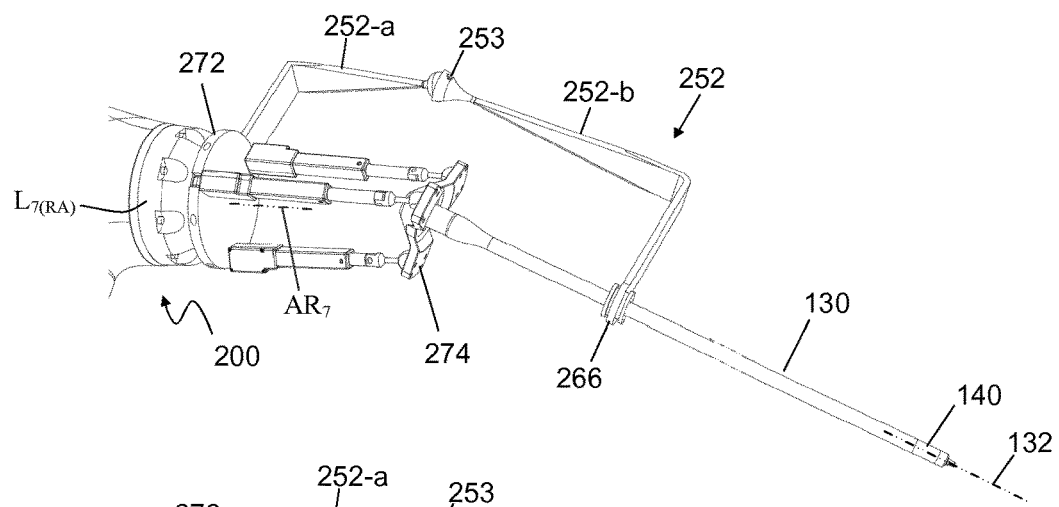
Figure 34:
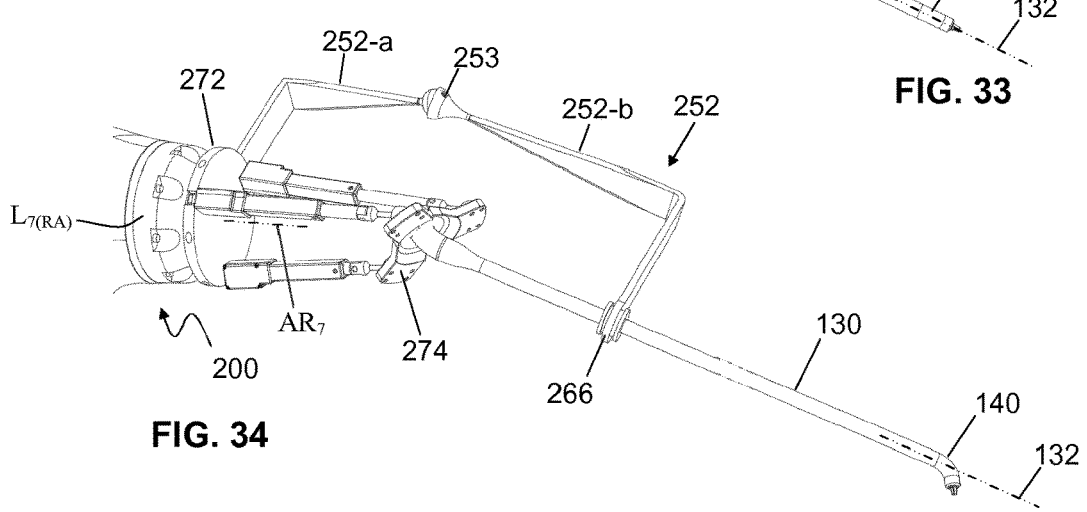

FIGS. 27 to 30 show different actuation positions of the adaptor (250) shown in FIG. 26. The shaft (130) of the instrument is typically supported by a trocar in the body of the patient. In FIGS. 27 and 28 the robotic arm (200) is set such that the instrument shaft (130) central axis (132) is co-axial with the axis of rotation of the last link ($L_{7(RA)}$) of the robotic arm (200) when the distal bendable part (140) is both straight (FIG. 27) and bent (FIG. 28). In FIGS. 29 and 30 the robotic arm (200) is set such that the instrument shaft (130) central axis (132) is inclined with the axis of rotation of the last link ($L_{7(RA)}$) of the robotic arm (200) when the distal bendable part (140) is both straight (FIG. 29) and bent (FIG. 30).

FIGS. 31 to 34 show different actuation positions of the adaptor (250) shown in FIG. 26, wherein the adaptor (250) is further provided with an adjustable supporting arm (252) having two rigid linkages (252-a and -b) joined by a ball-and-socket joint (253).whose position is repeatably lockable. Disposed at a distal end of the adjustable supporting arm (252) is an instrument guide (266) dismountably attached in fixed relation to the instrument shaft (130) and at the proximal end with an attachment (251) to the $1^{st}$ (proximal most) linkage ($L_7$) of the adapter (250). The instrument guide (266) is effectively in fixed positional and rotational relation with the $1^{st}$ (proximal most) linkage ($L_7$) of the adapter (250). In FIGS. 27 and 28 the adjustable supporting arm (252) is set such that the instrument shaft (130) central axis (132) is co-axial with the axis of rotation of the last link ($L_{7(RA)}$) of the robotic arm (200) when the distal bendable part (140) is both straight (FIG. 27) and bent (FIG. 28). In FIGS. 29 and 30 the adjustable supporting arm (252) is set such that the instrument shaft (130) central axis (132) is inclined with the axis of rotation of the last link ($L_{7(RA)}$) of the robotic arm (200) when the distal bendable part (140) is both straight (FIG. 29) and bent (FIG. 30). FIGS. 35 and 36 each show two robotic arms (200, 200') in close proximity each provided with an adapter (250, 250'); the distal bendable part (140, 140') is in a straight (FIG. 35) or bent (FIG. 36) configuration depending on the orientation of the adapter footplate (274, 274'). Actuation of the adapters (250, 250') rather than movement of the robotic arm (200) linkages, avoiding clashing movement of the links of the robotic arms (200, 200').

FIGS. 37 to 40 show different views of an adapter (250a) comprising a pair of plates (255, 256) separated by 4 links (257) each link (257) attached the plate by a revolute joint either side of the link. Each link is evenly arranged around the periphery of the plates. Tilting of the proximal plate (256) actuates tilting of the distal plate (255). The distal plate is in attached in fixed (rotational and positional) relation to the instrument connector (110). The proximal plate (256) may be actuated by two or more servo motors.

FIGS. 41 and 42 show an implementation of an adapter (250b) according to FIGS. 14 and 15 together with a drive system for each joint. The drive system comprises a motor (259a, 259b) wherein a housing of the motor is attached in fixed relation to a link ($L_8$, $L_9$). Attached non-rotatably to an adjacent link ($L_7$, $L_8$) is a pulley (258b) (e.g. non-geared or geared), a centre of rotation of the pulley (258b) is coaxial with an axis of rotation ($AR_8$, $AR_9$) of the joint. Torque supplied by the motor (259a, 259b) is transmitted by the pulley (258b) by a belt (258a, 258b). When the motor (259a, 259b) supplies torque, the motor (259a, 259b) rotates about the axis of the second (fixed) pulley cause movement around the axis of rotation of the joint ($AR_8$, $AR_9$). In FIG. 41 the steerable instrument is in a straight configuration, in FIG. 42 it is bent by the application of torque by motor 259a that rotates itself on link $L_8$ relative to link $L_7$ around $AR_8$.

Figure 43A:
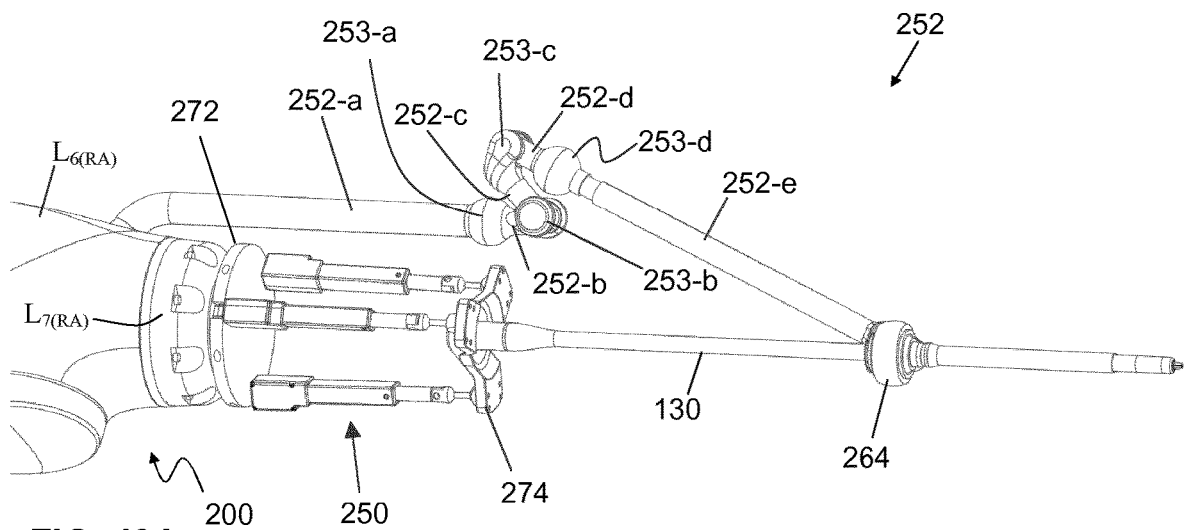
Figure 43B:
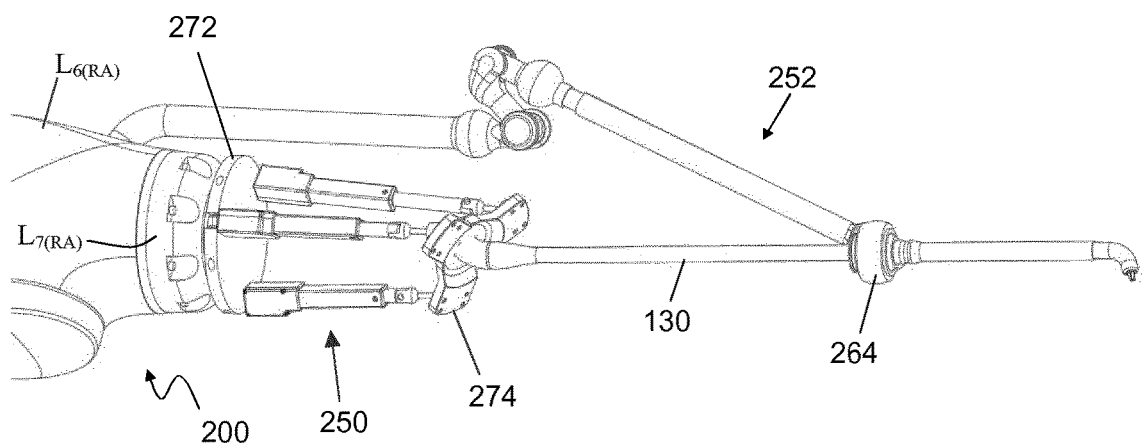
Figure 43C:
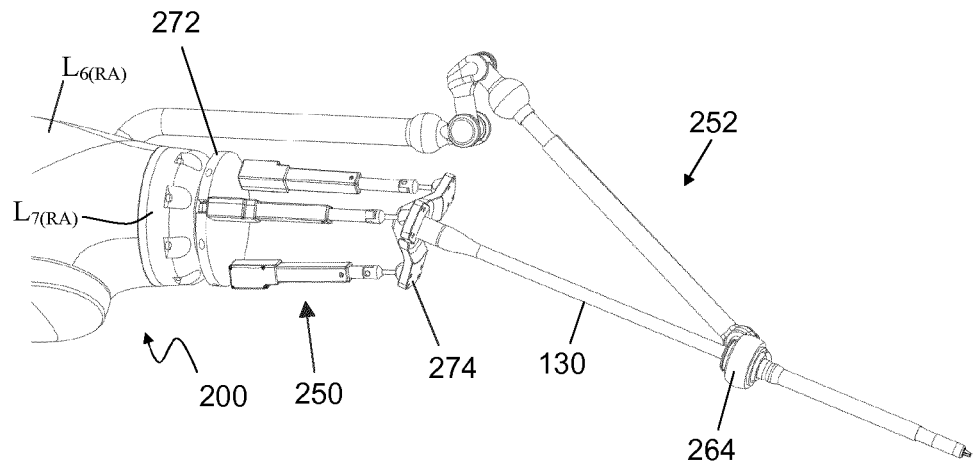
Figure 43D:
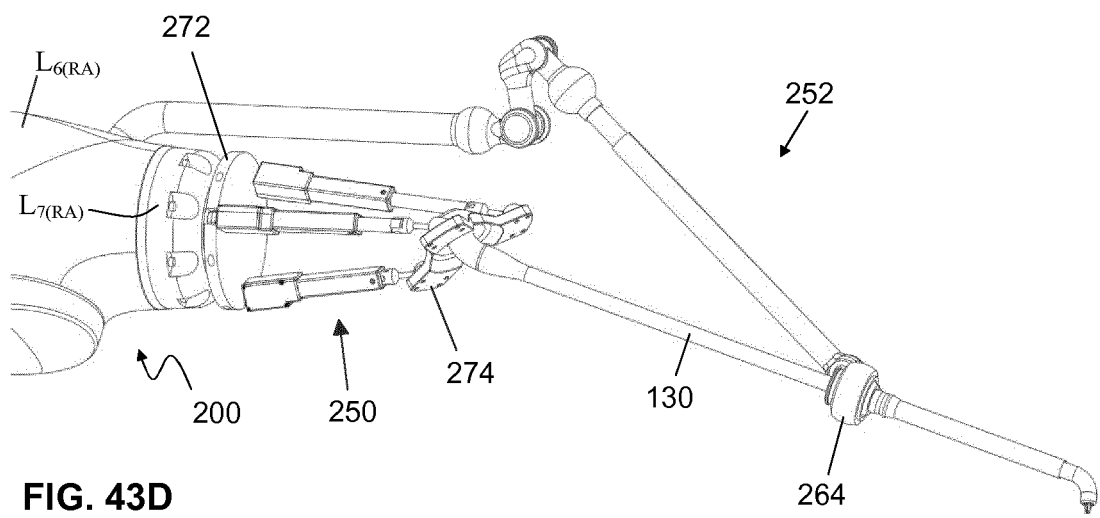

FIGS. 43A to D show different actuation positions of the adaptor (250) that is a tripod shown in FIG. 26, wherein a linkage ($L_{6(RA)}$) of the robotic arm (200) is attached to proximal end of a motorised adjustable supporting arm (252) having five rigid linkages (252-a to -e) joined by four revolute joints (252-a to -e) allow for continuous adjustment of the position and direction of the trocar (264) to which the instrument shaft (130) is dismountably attached. The five rigid linkages (252-a to -e) and four revolute joints (252-a to -e) are labelled in FIG. 43A. The trocar (264) is in adjustable positional and rotational relation with the linkage ($L_6$(RA)) of the robotic arm (2000). In FIGS. 43A and 43B the adjustable supporting arm (252) is set such that the instrument shaft (130) central axis (132) is co-axial with the axis of rotation of the last link ($L_{7(RA)}$) of the robotic arm (200) when the distal bendable part (140) is both straight (FIG. 43A) and bent (FIG. 43B). In FIGS. 43C and 43D the adjustable supporting arm (252) is set such that the instrument shaft (130) central axis (132) is inclined with the axis of rotation of the last link ($L_{7(RA)}$) of the robotic arm (200) when the distal bendable part (140) is both straight (FIG. 43C) and bent (FIG. 43D).

The invention claimed is:

1. A steerable instrument (100) controllable by a robotic arm (200), having a proximal end (20) and a distal (40) end comprising:
   a shaft (130), a bendable proximal part (120) configured to bend along a curve and a bendable distal part (140) configured to bend along a curve, a connector (110) having an axis of rotation (112) configured for dismountable attachment to the robotic arm (200), attached in fixed rotational relation along a longitudinal axis to the bendable proximal part (120), an end effector (150) having an axis of rotation (150) attached in fixed rotational relation along a longitudinal axis to the bendable distal part (140), the steerable instrument (100) configured such that:

the bendable distal part (140) bends responsive to bending of the bendable proximal part (120), and the end effector (150) is rotatable around its axis of rotation (150) when the bendable distal part (140) is in a bent position by a complementary rotation of the connector (110) around its axis of rotation (112), wherein the rotation of the connector (110) around its axis of rotation (112) rotates the bendable proximal part (120) in a bent position that is transmitted via an axial (A-A') rotation of the shaft (130) to the bendable distal part (140) in the bent position causing rotation of the end effector (150) around its axis of rotation (152) while the bendable distal part (140) is in the bent position, the shaft (130) is pivotable around a fulcrum zone (134) on the shaft (130) and changes direction pivoted around the fulcrum zone (134) responsive to a complementary movement of the connector (110), thereby providing control of the shaft (130) direction, bending of the bendable distal part (140), and rotation of the end effector (150) through robotic movement of the connector (110).

2. The steerable instrument (100) according to claim 1, wherein the connector (110) is configured to engage with a complementary fitting (260) of the robotic arm, such that the connector (110) is maintained in fixed rotational and positional relation with the fitting (260) and thus rotational and positional movements of the fitting (260) are directly transmitted to the connector (110) and to the bendable proximal part (120).

3. The steerable instrument (100) according to claim 1, wherein steerable instrument (100) is further configured such that the direction of the end effector (150) is changeable while the shaft is in a fixed rotational position by a complementary movement of the connector (110).

4. The steerable instrument (100) according to claim 1, wherein connector (110) comprises a rigid member for dismountable attachment to a complementary fitting on the robotic arm (200).

5. The steerable instrument according to claim 1, further comprising a motion amplifier region wherein consecutive plane sections therein gradually increase in size in the distal (40) to the proximal (20) direction, optionally disposed at least partially within the bendable proximal part (120), configured such that bending of the bendable distal part (140) responsive to bending of the bendable proximal part (120) is motion amplified.

6. The steerable instrument (100) according to claim 1, wherein the robotic arm (200) comprises a base end (232), an effector end (262) and a plurality of intervening linkages (230a-h) connected by joints (220a-i), wherein the arrangement of links and joints provides at least 6 degrees of freedom of movement to the effector end (260), wherein the effector end (262) is attached to a fitting (260) for dismountable attachment to the connector (110).

7. A system comprising a steerable instrument (100) according to claim 1, and a robotic arm (200) that comprises a base end (232), an effector end (262) and a plurality of intervening linkages (230a-h) connected by joints (220a-i), wherein the arrangement of links and joints provides at least 6 degrees of freedom of movement to the effector end (260), wherein the effector end (262) is attached to a fitting (260) for dismountable attachment to the connector (110).

8. The system according to claim 7, wherein the last two joints (FIG. 13—$R_7$, $R_8$) or three joints (FIG. 10—$R_5$, $R_6$, $R_7$; FIG. 11 $R_7$, $R_8$, $R_9$; FIG. 12 $R_7$, $R_8$, $R_9$) from the effector end (262) of the robotic arm (200) are arranged such that their axes of rotation intersect, and pass through a zone of motion (122) of the bendable proximal part (120) or through a geometric centre of the zone of motion (122), wherein the zone of motion (122) of the bendable proximal part (120) is a zone coinciding with a central axis (A-A') of the shaft where a central axis (152) of the connector (110), for different connector (110) directions, intersects.

9. The system according to claim 7, wherein robotic arm (200) comprises an adjustable or non-adjustable supporting arm (230f, 252) attachable at a first end to one of the robotic arm (200) linkages (230f) and attachable at a second end to:

a trocar (264) or a clamp for a trocar (264) and/or an instrument guide (266) configured to support a shaft (130) of the steerable instrument (100) or a trocar, wherein the supporting arm (230f, 252) maintains the trocar (264) or an instrument guide (266) in non-adjustable or adjustable relation to the linkage, and the direction of the linkage controls the direction of the trocar (264) or an instrument guide (266).

10. The system according to claim 7, wherein robotic arm (200) comprises a dismountable adapter (250) configured for attachment to an effector end of the existing robotic arm and which adds two or three or more last joints and associated linkages of the robot arm and a new an effector end (262) for attachment to the steerable instrument (100), optionally wherein the adapter (250) comprises an adjustable or non-adjustable supporting arm (230f, 252) attachable at a proximal end to a first link of the adapter (250) and attachable at a distal end to:

a trocar (264) or a clamp for a trocar (264) and/or an instrument guide (266) configured to support a shaft (130) of the steerable instrument (100) or a trocar (264), wherein the supporting arm (230f, 252) maintains the trocar (264) or an instrument guide (266) in non-adjustable or adjustable relation to the adapter (250) linkage, and the direction of the linkage controls the direction of the trocar (264) or an instrument guide (266).

11. The system according to claim 7, further comprising a control unit (300) configured to output control signals to the robotic arm (200) to effect movements of steerable instrument (100) that include:

rotation of the shaft (130) around the fulcrum zone (134), rotation of the shaft (130) axially (A-A'), displacement of the shaft (130) axially (A-A'), bending of the bendable distal part (140), and rotation of the end effector (150) when the bendable distal part (140) is in a bent position.

12. The system according to claim 11, where in the control unit (300) is configured to determine the position of the fulcrum zone (134) in response to a change in an axial position of the shaft (130), and wherein the output control signals to the robotic arm (200) account for a new position of the fulcrum zone (134) to effect a directional movement of the steerable instrument around a new position of the fulcrum zone (134).

13. The system according to claim 11, further comprising a manual input unit (400), wherein the control unit (300) is further configured to:
- receive a sensor signal from the manual input unit (400),
- output a control signal for the robotic arm (200) to control movement thereof responsive to the signal from the manual input unit (400).

14. The system according to claim 13, wherein the control unit (300) is further configured to:
- transform manual movement sensed by the manual input unit (400) to a corresponding movement of the instrument (200),
- optionally to scale a corresponding movement of the steerable instrument (200) compared with a manual movement sensed by the manual input unit (400),
- optionally to scale up bending of the bendable distal part (140) of the steerable instrument (200) compared with a corresponding manual movement sensed by the manual input unit (400), and
- optionally to dampen a corresponding movement of the instrument compared with the manual movement sensed by the manual input unit (400).

15. The system according to claim 11, wherein the control unit (300) generates control signals for moving the robotic arm (200) using a model of the steerable instrument (100) that treats bendable proximal part (120) as a joint that moves around a zone of motion (122) that is a zone coinciding with a central axis (A-A') of the shaft where a central axis (112) of the connector (110) intersects at a different connector (110) directions, and optionally that treats the bendable distal part (140) as a joint that moves around a zone of motion (142) that is a zone coinciding with a central axis (A-A') of the shaft where a central axis (152) of the end effector (150) intersects at a different end effector (150) directions.

16. A method of controlling a robotic arm (200) in a system according to claim 7 to move an attached steerable instrument (100), which method effects movements of steerable instrument (100) that include:
- rotation of the shaft (130) around the fulcrum zone (134),
- rotation of the shaft (130) axially (A-A'),
- displacement of the shaft (130) axially (A-A'),
- bending of the bendable distal part (140), and
- rotation of the end effector (150) when the bendable distal part (140) is in a bent position.

* * * * *